US010927154B2

(12) United States Patent
Olwill et al.

(10) Patent No.: US 10,927,154 B2
(45) Date of Patent: Feb. 23, 2021

(54) MULTI-SPECIFIC POLYPEPTIDE USEFUL FOR LOCALIZED TUMOR IMMUNOMODULATION

(71) Applicant: Pieris Pharmaceuticals GmbH, Freising-Weihenstephan (DE)

(72) Inventors: Shane Olwill, Freising-Weihenstephan (DE); Alexander Wiedenmann, Herbrechtingen (DE); Andrea Allersdorfer, Wolnzach (DE); Rachida Bel Aiba, Munich (DE); Gabriele Matschiner, Munich (DE); Bradley Lunde, Munich (DE)

(73) Assignee: Pieris Pharmaceuticals GmbH, Hallbergmoos (DE)

( * ) Notice: Subject to any disclaimer, the term of this patent is extended or adjusted under 35 U.S.C. 154(b) by 0 days.

(21) Appl. No.: 15/111,153

(22) PCT Filed: Jan. 12, 2015

(86) PCT No.: PCT/EP2015/050378
§ 371 (c)(1),
(2) Date: Jul. 12, 2016

(87) PCT Pub. No.: WO2015/104406
PCT Pub. Date: Jul. 16, 2015

(65) Prior Publication Data
US 2016/0362460 A1 Dec. 15, 2016

(30) Foreign Application Priority Data

Jan. 13, 2014 (EP) .................... 14150951
May 30, 2014 (EP) .................... 14170531
Oct. 23, 2014 (EP) .................... 14190124

(51) Int. Cl.
*C07K 16/32* (2006.01)
*C07K 14/47* (2006.01)
*C07K 16/28* (2006.01)

(52) U.S. Cl.
CPC .......... *C07K 14/47* (2013.01); *C07K 16/2818* (2013.01); *C07K 16/2863* (2013.01); *C07K 16/32* (2013.01); *C07K 2317/52* (2013.01); *C07K 2317/732* (2013.01); *C07K 2317/76* (2013.01); *C07K 2317/92* (2013.01); *C07K 2317/94* (2013.01); *C07K 2318/20* (2013.01);
(Continued)

(58) Field of Classification Search
CPC ............... C07K 16/32; C07K 16/2863; C07K 2317/32; C07K 2317/76; C07K 2319/33
USPC ................. 424/133.1, 134.1, 178.1
See application file for complete search history.

(56) References Cited

U.S. PATENT DOCUMENTS 5,728,553 A 3/1998 Goodey et al.
5,849,576 A 12/1998 Skerra et al.
(Continued)

FOREIGN PATENT DOCUMENTS

DE 4417598 A1 12/1995
DE 19641876 A1 4/1998
(Continued)

OTHER PUBLICATIONS

Lipocalin | definition of lipocalin by Medical dictionary (pp. 1-3; Dec. 18, 2017).*
Rothe et al. (BioDrugs (2018) 32:233-243).*
Schonfeld et al. (PNAS 106(20): 8198-8203).*
Olsson et al.; "CTLA-4 Ligation Suppresses CD28-induced NF-κB and AP-1 Activity in Mouse T Cell Blasts"; *J. Mol. Biol.*, 274(20) : 14400-14405 (May 1999).
(Continued)

*Primary Examiner* — Lynn A Bristol
(74) *Attorney, Agent, or Firm* — Choate, Hall & Stewart LLP; Dana M. Daukss

(57) ABSTRACT

The disclosure provides a multi-specific polypeptide with a first moiety specific for a tumor-associated antigen on tumor cell surface and a second moiety specific for an immune checkpoint protein, which multi-specific polypeptide can be useful for biasing a T-cell-mediated response to a tumor micro-environment. For example, the polypeptide may contain: a) a first binding domain, for example, a full-length antibody or an antigen-binding domain of an antibody, specifically recognizing a tumor-associated antigen on tumor cell surface, and b) a second binding domain, such as a lipocalin mutein, capable of stimulating T-cell proliferation e.g., by inhibiting a protein receptor that down-regulates the immune system. The first binding domain may be genetically linked (i.e., peptide bond at its N- or C-terminus) to the second binding domain. The multispecific polypeptide also may contain a third or yet additional specific binding moieties, any of which can specifically bind a distinct immune checkpoint protein. The polypeptide may contain an Fc region of an antibody or of an antigen-binding domain thereof and simultaneously engage (1) a T cell receptor complex of a T cell, (2) a tumor-associated antigen on tumor cell surface, while (3) preserving the Fc function of the Fc region to Fc receptor-positive cell. The polypeptide is useful for the induction of an anti-tumor immunity in humans and/or animals. The disclosure also provides thermal-stable lipocalin muteins specific for CTLA-4. The disclosure further relates to a process for the production of the polypeptide or muteins as well nucleic acids encoding for the polypeptide or muteins, to vectors comprising the same and to host cells comprising the vector. In another aspect, the disclosure provides for a pharmaceutical composition comprising the polypeptide or muteins and medical uses of the polypeptide or muteins.

Figure 1:
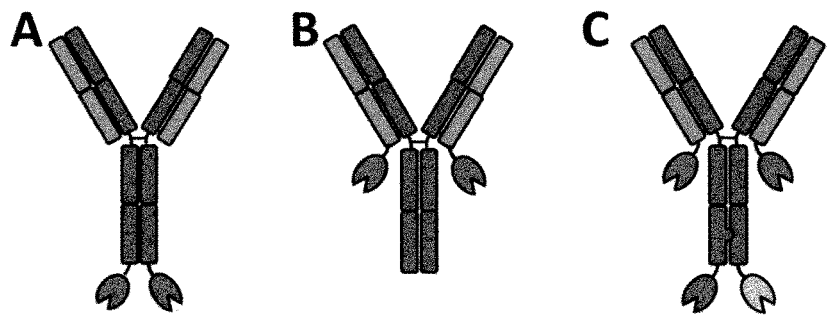

6 Claims, 8 Drawing Sheets
Specification includes a Sequence Listing.

(52) U.S. Cl.
CPC ...... *C07K 2319/00* (2013.01); *C07K 2319/30* (2013.01)

(56) References Cited

U.S. PATENT DOCUMENTS

| | | | |
|---|---|---|---|
| 6,099,517 | A | 8/2000 | Daugherty |
| 6,103,493 | A | 8/2000 | Skerra et al. |
| 6,123,936 | A | 9/2000 | Platz et al. |
| 6,177,074 | B1 | 1/2001 | Glue et al. |
| 6,337,316 | B1 | 1/2002 | El Tayar et al. |
| 6,403,564 | B1 | 6/2002 | Ganguly et al. |
| 6,500,930 | B2 | 12/2002 | Adamson |
| 6,620,413 | B1 | 9/2003 | De Sauvage et al. |
| 6,682,736 | B1 | 1/2004 | Hanson et al. |
| 6,696,245 | B2 | 2/2004 | Winter et al. |
| 6,719,972 | B1 | 4/2004 | Gribben et al. |
| 7,118,915 | B2 | 10/2006 | Vogt et al. |
| 7,250,297 | B1 | 7/2007 | Beste et al. |
| 7,252,998 | B2 | 8/2007 | Skerra et al. |
| 7,892,827 | B2 * | 2/2011 | Matschiner ............ C07K 14/47 435/325 |
| 9,221,885 | B2 * | 12/2015 | Matschiner ............ C07K 14/47 |
| 2002/0086014 | A1 | 7/2002 | Korman et al. |
| 2003/0069395 | A1 | 4/2003 | Sato et al. |
| 2006/0058510 | A1 | 3/2006 | Skerra et al. |
| 2006/0088908 | A1 | 4/2006 | Skerra et al. |
| 2009/0042785 | A1 | 2/2009 | Matschiner et al. |
| 2014/0051645 | A1 | 2/2014 | Matschiner et al. |
| 2018/0021418 | A1 * | 1/2018 | Hinner ............... C07K 14/7051 424/93.21 |

FOREIGN PATENT DOCUMENTS

| | | |
|---|---|---|
| DE | 19742706 A1 | 4/1999 |
| DE | 19926068 C1 | 1/2001 |
| EP | 0 330 451 A2 | 8/1989 |
| EP | 0 361 991 A2 | 4/1990 |
| WO | WO-95/33770 A1 | 12/1995 |
| WO | WO-96/23879 A1 | 8/1996 |
| WO | WO-98/16873 A1 | 4/1998 |
| WO | WO 98/33914 A1 | 8/1998 |
| WO | WO-99/16873 A1 | 4/1999 |
| WO | WO-99/064016 A1 | 12/1999 |
| WO | WO-00/37504 A2 | 6/2000 |
| WO | WO-00/075308 A1 | 12/2000 |
| WO | WO-01/14424 A2 | 3/2001 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO 2006/056464 A2 | 6/2006 |
| WO | WO-2007/038619 A2 | 4/2007 |
| WO | WO 2009/068649 A2 | 6/2009 |
| WO | WO 2009/114110 A1 | 9/2009 |
| WO | WO 2010/097394 A1 | 9/2010 |
| WO | WO 2010/136492 A2 | 12/2010 |
| WO | WO 2011/015634 A2 | 2/2011 |
| WO | WO 2012/072806 A1 | 6/2012 |
| WO | WO 2013/164694 A1 | 11/2013 |

OTHER PUBLICATIONS

Junttila et al.; "Superior In vivo Efficacy of Afucosylated Trastuzumab in the Treatment of HER2-Amplified Breast Cancer"; *Cancer Res.*, 70(11): 4481-4489 (Jun. 2010)(Published online May 2010).
Biburger et al.; "A Novel Bispecific Tetravalent Antibody Fusion Protein to Target Costimulatory Activity for T-cell Activation to Tumor Cells Overexpressing ErbB2/HER2"; *J. Mol. Biol.*, 346: 1299-1311 (Mar. 2005).
Altschul et al.; "Basic Local Alignment Search Tool"; *J. Mol. Biol.*, 215:403-410 (1990).
Altschul et al.; "Gapped BLAST and PSI-BLAST: a new generation of protein database search programs"; *Nucleic Acids Res.*, 25(17):3389-3402 (1997).
Smith et al.; "Identification of Common Molecular Subsequences"; *J. Mol. Biol.*, 147:195-197 (1981).
PCT International Search Report issued in application No. PCT/EP2015/050378 dated Jul. 3, 2015.
Altuvia et al., Ranking potential binding peptides to MHC molecules by a computational threading approach, J. Mol. Biol., 1995, 249:244-250.
Amstutz, P. et al., In vitro display technologies: novel developments and applications, Curr. Opin. Biotechnol., 2001, 12:400-405.
Attia et al., "Autoimmunity Correlates with Tumor Regression in Patients with Metastatic Melanoma Treated with Anti-Cycotoxic T-Lymphocyte Antigen-4," Journal of Clinical Oncology, Sep. 1, 2005, 23(25):6043-6053.
Bachmann, Barbara J., Linkage Map of *Escherichia coli* K-12. Edition 8, Microbial. Rev., Jun. 1990, 54(2):130-197.
Balzano et al,. , "CTLA-4 and CD28: Similar Proteins, Neighbouring Genes," Int. J. Cancer, 1992, Suppl. 7:28-32.
Beck, et al., Nucleotide Sequence and Genome Organisation of Filamentous Bacteriophages f1 and fd, Gene, vol. 16, pp. 35-58, 1981.
Beste, G. et al., Small antibody-like proteins with prescribed ligand specificities derived from the lipocalin fold, Proc. Natl. Acad. Sci. USA, Mar. 1999, 96:1898-1903.
Binder, U. et al., High-throughput Sorting of an Anticalin Library via EspP-mediated Functional Display on the *Escherichia coli* Cell Surface, J. Mol. Biol., 2010; 400: 783-802.
Bittker, J. et al., Nucleic acid evolution and minimization by nonhomologous random recombination, Nat. Biotechnol., Oct. 2002, 20:1024-1029.
Bork, Peer, Powers and Pitfalls in Sequence Analysis: The 70% Hurdle, Genome Research, 2000, vol. 10, pp. 398-400.
Bos et al., OctoDEX.TM.—Controlled Release of Pharmaceutical Proteins from Hydrogels, Business Briefing: Pharmatech, 2003:1-6.
Bruckdorfer, T., et al., From Production of Peptides in Milligram Amounts for Research to Multi-Tons Quantities for Drugs of the Future, Curr. Pharm. Biotechnol., 2004, 5:29-43.
Brumano et al., "Thermodynamics of Unfolding of β-Trypsin at pH 2.8," Arch. Biochem. Biophys., Oct. 1, 2000, 382(1):57-62.
Bullock, W. et al., XL1-Blue: A High Efficiency Plasmid Transforming recA *Escherichia coli* Strain with Beta-Galactosidase Selection, Biotechniques, 1987, 5(4):376-378.
Bundgaard, J.R. et al., Molecular Cloning and Expression of a cDNA Encode NGAL: A Lipocalin Expressed in Human Neutrophils, Biochemical and Biophysical Research Communications, Aug. 15, 1994, pp. 1468-1475, vol. 202, No. 3, XP002036694.
Chambers et al., "CTLA-4-Mediated Inhibition in Regulation of T Cell Responses: Mechanisms and Manipulation in Tumor Immunotherapy," Annu. Rev. Immunol., 2001, 19:565-594.
Chambers et al., "Thymocyte development is normal in CTLA-4-deficient mice," Proc. Natl. Acad. Sci. USA., Aug. 1997, 94(17):9296-9301.
Chan et al., The primary structure of rat α 2μ globulin-related protein, Nucleic Acids Research, vol. 16, No. 23, pp. 11368, 1988.
Chikuma et al., "CTLA-4: Acting at the Synapse," Mol. Interv., Jul. 2002, 2(4):205-208.
Cohen et al., "Stability of yeast iso-1-ferricytochrome c as a function of pH and temperature," Protein Sci., 1994, 3(8):1253-1260.
Coles, et al., The Solution Structure and Dynamics of Human Neutrophil Gelatinase-associated Lipocalin, J. Mol. Biol., vol. 289, pp. 139-157, 1999.
Dennis, M. et al., Albumin Binding as a General Strategy for Improving the Pharmacokinetics of Proteins, J. Biol. Chem., Sep. 20, 2002, 277(38):35035-35043.
Doerks et al., Protein annotation: detective work for function prediction, Trends in Genetics, 1998, vol. 14, pp. 248-250.
Egen et al., "CTLA-4: new insights into its biological function and use in tumor immunotherapy," Nat. Immunol., Jul. 2002, 3(7):611-618.

(56) References Cited

OTHER PUBLICATIONS

Fitzgerald, Kevin, In Vitro Display Technologies—New Tools for Drug Discovery, Reviews, vol. 5, No. 6, pp. 253-258, Jun. 2000.
Fling, S. and Gregerson, D., Peptide and Protein Molecular Weight Determination by Electrophoresis Using a High-Molarity Tris Buffer System without Urea, Anal. Biochem., 1986, 155:83-88.
Flower, Darren R., The lipocalin protein family: structure and function, Biochem. J., 1996, 318:1-14.
Fuerteges, F. and Abuchowski, A., The Clinical Efficacy of Poly(Ethylene Glycol)-Modified Proteins,: J. Control. Release, 1990, 11:139-148.
Gaillard, P. et al., Diphtheria toxin receptor-targeted brain drug delivery, International Congress Series., 2005, 1277:185-198.
Gaillard, P. et al., Targeted delivery across the blood-brain barrier, Expert Opin Drug Deliv., 2005, 2(2):299-309.
Goetz, D. et al., Ligand Preference Inferred from the Structure of Neutrophil Gelatinase Associated Lipocalin, Biochemistry, 2000, 39:1935-1941.
Hengen, Paul N., Methods and Reagents, Trends Biochem. Sci., vol. 21, pp. 75-76, 1996.
Hodi et al., "Biologic activity of cytotoxic T lymphocyte-associated antigen 4 antibody blockade in previously vaccinated metastatic melanoma and ovarian carcinoma patients," Proc. Natl. Acad. Sci. USA, Apr. 15, 2003, 100(8):4712-4717.
Hoess, Ronald H., Phage Display of Peptides and Protein Domains, Structural Biology, vol. 3, pp. 572-279, 1993.
Holliger et al., 'Diabodies': Small bivalent and bispecific antibody fragments, PNAS USA, Jul. 1993, 90:6444-6448.
Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Ill et al., "Design and construction of a hybrid immunoglobulin domain with properties of both heavy and light chain variable regions," Protein Engineering, 1997, 10(8):949-957.
Kaufman et al., Transgenic Analysis of 100-kb Human beta-Globin Cluster-Containing DNA Fragment Propagated as a Bacterial Artificial Chromosome, Blood, 1999, 94:3178-3184.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lute et al., "Human CTLA4 knock-in mice unravel the quantitative link between tumor immunity and autoimmunity induced by anti-CTLA-4 antibodies," Blood, Nov. 1, 2005, 106(9): 3127-3133.
Martin et al., The affinity-selection of a minibody polypeptide inhibitor of human interleukin-6, The EMBO Journal, 1994, 13(22):5303-5309.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
McCoy et al., "Protective Immunity to Nematode Infection is Induced by CTLA-4 Blockade," J. Exp. Med., Jul. 21, 1997, 186(2):183-187.
Meidan et al., Emerging Technologies in Transdermal Therapeutics, American Journal of Therapeutics, 2004, 11:312-316.
Murakami, H. et al., Random insertion and deletion of arbitrary number of bases for codon-based random mutation of DNAs, Nat. Biotechnol., Jan. 2002, 20:76-81.
Murata et al., "Expression of the Costimulatory Molecule BB-1, the Ligands CTLA-4 and CD28, and their mRNA in Inflammatory Myopathies," Am. J. Pathol., Aug. 1999, 155(2):453-460.
Murphy et al., "Blockade of CTLA-4 Enhances Host Resistance to the Intracellular Pathogen, Leishmania donovani," J. Immunol., 1998, 161:4153-4160.
Osborn, B. et al., Pharmacokinetic and Pharmacodynamic Studies of a Human Serum Albumin-Interferon-$\alpha$ Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between $\alpha$1-Acid Glycoprotein and Serum Retinol-Binding Protein and Its Relatives, 1987, The FASEB journal 1.3 (1987): 209-214.
Phan et al., "Cancer regression and autoimmunity induced by cytotoxic T lymphocyte-associated antigen 4 blockade in patients with metastatic melanoma," Proc. Natl. Acad. Sci. USA, Jul. 8, 2003, 100(14):8372-8377.
Pini, A. et al., Phage Display and Colony Filter Screening for High-Throughput Selection of Antibody Libraries, Comb. Chem. High Throughput Screen., 2002, 5:503-510.
Roberts, Richard W., Totally In Vitro Protein Selection Using mRNA-Protein Fusions and Ribosome Display, Current Opinion in Chemical Biology, vol. 3, pp. 268-273, 1999.
Sanderson et al., "Autoimmunity in a Phase I Trial of a Fully Human Anti-Cytotoxic T-Lymphocyte Antigen-4 Monoclonal Antibody with Multiple Melanoma Peptides and Montanide ISA 51 for Patients with Resected Stases III and IV Melanoma," J. Clin.Oncol. Feb. 1, 2005 23(4):741-750.
Schiweck et al., Fermenter production of an artificial fab fragment rationally designed for the antigen cystatin and its optimized crystallization through constant domain shuffling, Proteins: Structure, Function, and Genetics, 1995, 23:561-565.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. and Skerra, A., Tuning ligand affinity, specificity, and folding stability of an engineered lipocalin variant—a so-called 'anticalin'—using a molecular random approach, Biophysical Chemistry 96 (2002) 213-228.
Schlehuber, S. et al., A Novel Type of Receptor Protein, Based on the Lipocalin Scaffold, with Specificity for Digoxigenin, J. Mol. Biol., 2000, 297:1105-1120.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Silverman et al., Multivalent avimer proteins evolved by exon shuffling of a family of human receptor domains, Nature Biotechnology, Dec. 2005, 23(12):1556-1561.
Skerra et al., 'Anticalins': a new class of engineered ligand-binding proteins with antibody-like properties, Reviews in Molecular Biotechnology, 2001, 74:257-275.
Skerra, A. and Schmidt, T., Use of the Strep-Tag and Streptavidin for Detection and Purification of Recombinant Proteins, Methods in Enzymology, 2000, vol. 326, pp. 271-304.
Skerra, Arne, Lipocalins as a scaffold, Biochimica et Biophysica Acta, 2000, 1482:337-350.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.

(56) References Cited

OTHER PUBLICATIONS

Skolnick, J. et al., From genes to protein structure and function: novel applications of computational approaches in the genomic era, Trends in Biotech, 2000, vol. 18, No. 1, pp. 34-39.
Stoesz, S. et al., Overexpression of neu-related lipocalin (NRL) in neu-initiated but not ras or chemically initiated rat mammary carcinomas, Oncogene (1995), 11, pp. 2233-2241.
Tivol et al., "Loss of CTLA-4 Leads to Massive Lymphoproliferation and Fatal Multiorgan Tissue Destruction, Revealing a Critical Negative Regulatory Role of CTLA-4," Immunity, Nov. 1995, 3(5):541-547.
Tokuriki, N. and Tawfik, D., Stability effects of mutations and protein evolvability, Current Opinion in Structural Biology, 2009, vol. 19, pp. 596-604.
Traunecker et al., Bispecific single chain molecules (Janusins) target cytotoxic lymphocytes on HIV infected cells, The EMBO Journal, 1991, 10(12):3655-3659.
Traunecker et al., Janusin: New Molecular Design for Bispecific Reagents, Int. J. Cancer, 1992, Supplement 7, 51-52.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
Vajo, Z. and Duckworth, W., Genetically Engineered Insulin Analogs: Diabetes in the New Millenium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang, A. et al. Rapid analysis of gene expression (RAGE) facilitates universal expression profiling, Nuc. Acids Res. 27: 4609-4618, 1999; p. 4617.
Wang, A. M. et al., Molecular Cloning of the Complementary DNA for Human Tumor Necrosis Factor, Science, vol. 228, pp. 149-154, 1985 (Abstract).
Waterhouse et al., "Lymphoproliferative Disorders with Early Lethality in Mice Deficient in CTLA-4," Science, Nov. 10, 1995, 270(5238):985-988.
Wells, J. et al., Rapid Evolution of Peptide and Protein Binding Properties In Vitro, Current Opinion in Structural Biology, vol. 2, pp. 597-604, 1992.
Wells, James A., Additivity of Mutational Effects in Proteins, Biochemistry, Sep. 18, 1990, 29(37):8509-8517.
Wilson, D. et al., The use of mRNA display to select high-affinity protein-binding peptides, Proc. Natl. Acad. Sci. USA, Mar. 27, 2001, 98(7):3750-3755.
Yanisch-Perron, C. et al., Improved M13 phage cloning vectors and host strains: nucleotide sequences of the M13mp18 and pUC19 vectors, Gene, 1985, 33:103-119.
Zaccolo, M.et al., An Approach to Random Mutagenesis of DNA Using Mixtures of Triphosphate Derivatives of Nucleoside Analogues, J. Mol. Biol., 1996, 255:589-603.

\* cited by examiner

Cell-based assay to assess inhibition of B7.1 binding to CTLA-4 by lipocalin mutein and multi-specific polypeptide on human CTLA-4-transfected CHO cells.

Cell-based assay to assess binding affinity of
Reference molecule 1 and multi-specific polypeptide
to Her2 on T47D cells.

Cell-based assay to assess binding of Reference molecule 1 and multi-specific polypeptides to Her2 on SKBR3 cells.

Cell-based assay to assess binding of Reference molecule 2 and multi-specific polypeptides to EGFR on A431 cells.

Cell-based assay to assess binding to CTLA-4 by lipocalin mutein and multi-specific polypeptide on human CTLA-4-transfected Jurkat cells.

A

B

SEQUENCE LISTING

<160> NUMBER OF SEQ ID NOS: 109

<210> SEQ ID NO 1
<211> LENGTH: 178
<212> TYPE: PRT
<213> ORGANISM: Homo sapiens
<220> FEATURE:
<223> OTHER INFORMATION: Wild type hNGAL (Lcn2)

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Leu Leu Arg Asp Asp Gln His Pro
        35                  40                  45

Met Asp Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
            100                 105                 110

```
Thr Asp Tyr Asn Gln Tyr Ala Val Val Phe Phe Lys His Ala Asp Thr
            115                 120                 125

Asn Tyr Glu Ser Phe Ser Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Gln Asp Gln His Pro
        35                  40                  45

Met Leu Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45
```

```
Met Pro Met Tyr Ala Thr Ile Tyr Glu Leu Lys Gly Asp Lys Ser Tyr
        50                  55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Ser
            115                 120                 125

Asn Tyr Glu Ser Phe Ser Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 5

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Ser Asp Gln His Pro
             35                  40                  45

Met Arg Met Tyr Ala Thr Ile Tyr Glu Leu Lys Gly Asp Lys Ser Tyr
        50                  55                  60

Asn Val Thr Ser Val Ile Ser Ser His Lys Lys Cys Leu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Trp Ser Tyr Leu Val Arg Val Val Ser
                100                 105                 110

Thr Asp Tyr Asn Gln Tyr Ala Val Val Phe Phe Lys His Ala Asp Thr
            115                 120                 125

Asn Tyr Glu Ser Phe Ser Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
```

<223> OTHER INFORMATION: Description of Artificial Sequence: Synthetic
      hNGAL mutein polypeptide

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Ser Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Ser Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Glu Ser Tyr Leu Val Arg Val Val Ser
            100                 105                 110

Thr Asp Tyr Asn Gln Tyr Ala Val Val Phe Phe Lys Tyr Ala Ser Asp
        115                 120                 125

Asn Asp Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Leu Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Arg Ser Tyr Gly Asp Lys Thr Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly

```
145                 150                 155                 160
Leu Pro Glu Asn His Ile Val Phe Pro Val Pro Ile Asp Gln Cys Ile
                165                 170                 175

Asp Gly

<210> SEQ ID NO 8
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Val Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Tyr Ile Trp Arg Asn Asp Arg Tyr Pro
        35                  40                  45

Met Gln Met Tyr Ala Thr Ile Tyr Glu Leu Lys Glu Asp Lys Ser Tyr
50                  55                  60

Asn Val Thr Ser Val Ile Phe Asp Thr Lys Lys Cys Glu Tyr Pro Ile
65                  70                  75                  80
```

```
Ala Thr Phe Val Pro Gly Ser Gln Pro Gly Glu Phe Thr Leu Gly Asn
                85                  90                  95

Ile Lys Ser Tyr Arg Met Asp Thr Ser Tyr Leu Val Arg Val Val Ser
            100                 105                 110

Thr Asn Tyr Asn Gln His Ala Met Val Phe Phe Lys Gln Val Asn His
        115                 120                 125

Asn Thr Glu His Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 11

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Met Val Phe Phe Lys Leu Ala Glu Asp
                115                 120                 125

Asn Ala Glu Phe Phe Ala Val Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
                115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 13
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 13

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu His Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln His Ala Met Val Phe Phe Glu Leu Val Glu Asp
        115                 120                 125

Asn Ala Gly Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 14
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 14

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Glu Leu Val Glu Asp
```

```
            115                 120                 125
Asn Ala Gly Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 15
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Val Val Phe Phe Gln Leu Val Glu Asp
        115                 120                 125

Asn Ala Gly Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Leu Gly Leu Ala Gly Asn Arg Ile Leu Arg Asp Asp Gln His Pro
        35                  40                  45
```

```
Met Asn Met Tyr Ala Thr Ile Tyr Glu Leu Lys Glu Asp Lys Ser Tyr
            50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Met Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 17
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 17

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
            50                  55                  60

Asn Val Thr Ser Val Ile Phe Pro His Lys Lys Cys Glu Tyr Thr Phe
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Thr Val Phe Phe Lys Leu Ala Glu Asp
            115                 120                 125

Asn Ala Glu Phe Phe Ala Val Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 18
<211> LENGTH: 178
<212> TYPE: PRT
<213> ORGANISM: Artificial Sequence
<220> FEATURE:
<223> OTHER INFORMATION: Description of Artificial Sequence: Synthetic
``` hNGAL mutein polypeptide

<400> SEQUENCE: 18

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Leu Ala Gly Asn Arg Ile Leu Arg Asp Asp Gln His Pro
        35                  40                  45
Met Asp Met Tyr Ala Thr Ile Tyr Glu Leu Lys Glu Asp Lys Ser Tyr
    50                  55                  60
Asn Val Thr Ser Val Ile Phe Pro His Lys Lys Cys Glu Tyr Thr Ile
65                  70                  75                  80
Ala Thr Phe Val Pro Gly Ser Gln Pro Gly Glu Phe Thr Leu Gly Asn
                85                  90                  95
Ile Lys Ser Tyr Gly Asp Lys Thr Ser Tyr Leu Val Arg Val Val Ser
            100                 105                 110
Thr Asn Tyr Asn Gln His Ala Thr Val Phe Phe Lys Leu Ala Glu Asp
        115                 120                 125
Asn Ala Glu Phe Phe Ala Ile Thr Ile Tyr Gly Arg Thr Lys Glu Leu
    130                 135                 140
Ala Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 19
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 19

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Leu Ala Gly Asn Arg Ile Leu Arg Asp Asp Arg His Pro
        35                  40                  45
Met Asn Met Tyr Ala Thr Ile Tyr Glu Leu Lys Glu Asp Lys Ser Tyr
    50                  55                  60
Asn Val Thr Ser Val Ile Phe Pro His Lys Lys Cys Glu Tyr Thr Ile
65                  70                  75                  80
Ala Thr Phe Val Pro Gly Ser Gln Pro Gly Glu Phe Thr Leu Gly Asn
                85                  90                  95
Ile Lys Ser Tyr Gly Asp Lys Thr Ser Tyr Leu Val Arg Val Val Ser
            100                 105                 110
Thr Asn Tyr Asn Gln His Ala Thr Val Phe Phe Lys Leu Ala Glu Asp
        115                 120                 125
Asn Ala Glu Phe Phe Ala Ile Thr Ile Tyr Gly Arg Thr Lys Glu Leu
    130                 135                 140
Ala Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
                165                 170                 175

Asp Gly

<210> SEQ ID NO 20
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 20

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asp Val Thr Ser Val Ile Phe Pro His Lys Lys Cys Glu Tyr Thr Thr
65                  70                  75                  80

Ala Thr Phe Val Pro Gly Ser Gln Pro Gly Glu Phe Thr Leu Gly Asn
                85                  90                  95

Ile Lys Ser Tyr Gly Gly Lys Thr Ser Tyr Leu Val Arg Val Val Ser
            100                 105                 110

Thr Asn Tyr Asn Gln His Ala Thr Val Phe Phe Lys Leu Ala Gly Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 21
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 21

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn

```
                85                  90                  95
Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 22
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 22

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Ser Asp
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 23
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 23

Gln Asp Ser Thr Ser Asp Leu Ile Pro Ala Pro Pro Leu Ser Lys Val
1               5                   10                  15
```

-continued

```
Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Ser Asp
             85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 24
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 24

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Leu Ser His Lys Lys Cys Glu Tyr Thr Ile
 65                  70                  75                  80

Ala Thr Phe Val Pro Gly Ser Arg Pro Gly Glu Phe Thr Leu Gly Asn
             85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 25
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 25

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asp Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Ser Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 26
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 26

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Leu Ser His Lys Lys Cys Glu Tyr Thr Val
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125
```

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 27
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Val Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 28
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr

-continued

```
                    50                  55                  60
Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
                115                 120                 125

Asp Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 29
<211> LENGTH: 178
<212> TYPE: PRT
<213> ORGANISM: Artificial Sequence
<220> FEATURE:
<223> OTHER INFORMATION: Description of Artificial Sequence: Synthetic
   hNGAL mutein polypeptide

<400> SEQUENCE: 29

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
         50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln His Ala Met Val Phe Phe Lys Leu Val Glu Asp
                115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 30
<211> LENGTH: 178
<212> TYPE: PRT
<213> ORGANISM: Artificial Sequence
<220> FEATURE:
<223> OTHER INFORMATION: Description of Artificial Sequence: Synthetic
   hNGAL mutein polypeptide -continued

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Tyr Ile Trp Arg Asn Asp Arg Tyr Pro
        35                  40                  45

Met Gln Met Tyr Ala Thr Ile Tyr Glu Leu Lys Glu Asp Lys Ser Tyr
    50                  55                  60

Asn Val Thr Ser Val Ile Phe Asp Thr Lys Lys Cys Glu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Arg Met Asp Thr Ser Tyr Leu Val Arg Val Val Ser
            100                 105                 110

Thr Asn Tyr Asn Gln His Ala Met Val Phe Phe Lys Val Asn His
        115                 120                 125

Asn Thr Glu His Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 31
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 31

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Met Val Phe Phe Lys Leu Ala Glu Asp
        115                 120                 125

Asn Ala Glu Phe Phe Ala Val Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
                165                 170                 175

Asp Gly

<210> SEQ ID NO 32
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 33
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95
```

```
Ile Lys Ser Tyr Gly Asp Lys Thr Ser Tyr Leu Val Arg Val Val Ser
            100                 105                 110

Thr Asn Tyr Asn Gln His Ala Thr Val Phe Lys Leu Ala Glu Asp
            115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 34
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Phe Pro His Lys Lys Cys Glu His Thr Ile
65                  70                  75                  80

Ala Thr Phe Val Pro Gly Ser Gln Pro Gly Glu Phe Thr Leu Gly Asn
            85                  90                  95

Ile Lys Ser Tyr Gly Asp Lys Thr Ser Tyr Leu Val Arg Val Val Ser
            100                 105                 110

Thr Asp Tyr Asn Gln His Ala Met Val Phe Glu Leu Val Glu Asp
            115                 120                 125

Asn Ala Gly Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 35
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 35

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
```

```
            20                  25                  30
Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Glu Leu Val Glu Asp
        115                 120                 125

Asn Ala Gly Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 36
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 36

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Val Val Phe Phe Gln Leu Val Glu Asp
        115                 120                 125

Asn Ala Gly Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 37
```

<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 37

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Leu Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 38
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 38

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Phe Pro His Lys Lys Cys Glu Tyr Thr Phe
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Ala Glu Asp
        115                 120                 125

```
Asn Ala Glu Phe Phe Ala Val Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 39
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asp Met Tyr Ala Thr Ile Tyr Glu Leu Lys Glu Asp Lys Ser Tyr
50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
            115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 40

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Arg His Pro
            35                  40                  45

Met Asn Met Tyr Ala Thr Ile Tyr Glu Leu Lys Glu Asp Lys Ser Tyr
50                  55                  60
```

```
Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 41
<211> LENGTH: 178
<212> TYPE: PRT
<213> ORGANISM: Artificial Sequence
<220> FEATURE:
<223> OTHER INFORMATION: Description of Artificial Sequence: Synthetic
    hNGAL mutein polypeptide

<400> SEQUENCE: 41

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asp Val Thr Ser Val Ile Phe Pro His Lys Lys Cys Glu Tyr Thr Thr
 65                  70                  75                  80

Ala Thr Phe Val Pro Gly Ser Gln Pro Gly Glu Phe Thr Leu Gly Asn
                 85                  90                  95

Ile Lys Ser Tyr Gly Gly Lys Thr Ser Tyr Leu Val Arg Val Val Ser
            100                 105                 110

Thr Asn Tyr Asn Gln His Ala Thr Val Phe Phe Lys Leu Ala Gly Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 42
<211> LENGTH: 178
<212> TYPE: PRT
<213> ORGANISM: Artificial Sequence
<220> FEATURE:
<223> OTHER INFORMATION: Description of Artificial Sequence: Synthetic
    hNGAL mutein polypeptide

```
<400> SEQUENCE: 42

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Leu Ser His Lys Lys Cys Glu Tyr Thr Val
65                  70                  75                  80

Ala Thr Phe Val Pro Gly Ser Gln Pro Gly Glu Phe Thr Leu Gly Asn
            85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 43
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 43

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asp Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
            85                  90                  95

Ile Lys Ser Tyr Gly Asp Lys Thr Ser Tyr Leu Val Arg Val Val Ser
            100                 105                 110

Thr Asp Tyr Ser Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

Asp Gly

<210> SEQ ID NO 44
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 44

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Ser Asp
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 45
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 45

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Val Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95
```

```
Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Leu Ser His Lys Lys Cys Glu Tyr Thr Ile
65                  70                  75                  80

Ala Thr Phe Val Pro Gly Ser Arg Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 47
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 48
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 48

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asp Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 49
<211> LENGTH: 178

```
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 49

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 50
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 50

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
```

```
                130                 135                 140

Ala Cys Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 51
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 51

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Cys Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 52
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 52

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
50                  55                  60
```

```
Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Cys Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 53
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 53

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Cys Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 54
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 54
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
    130                 135                 140

Cys Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 55
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 55

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Cys Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 56
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 56

```
Gln Asp Ser Thr Ser Asp Leu Ile Pro Ala Pro Pro Leu Cys Lys Val
1               5                   10                  15
Pro Leu Gln Gln Asn Phe Gln Asp Asn Gln Phe His Gly Lys Trp Tyr
                20                  25                  30
Val Val Gly Leu Ala Gly Asn Arg Ile Leu Arg Asp Asp Gln His Pro
            35                  40                  45
Met Asn Met Tyr Ala Thr Ile Tyr Glu Leu Lys Glu Asp Lys Ser Tyr
        50                  55                  60
Asn Val Thr Ser Val Ile Ser Ser His Lys Lys Cys Glu Tyr Thr Ile
65                  70                  75                  80
Ala Thr Phe Val Pro Gly Ser Gln Pro Gly Glu Phe Thr Leu Gly Asn
                85                  90                  95
Ile Lys Ser Tyr Gly Asp Lys Thr Ser Tyr Leu Val Arg Val Val Ser
                100                 105                 110
Thr Asp Tyr Asn Gln Tyr Ala Val Val Phe Phe Lys Leu Ala Glu Asp
            115                 120                 125
Asn Ala Glu Phe Phe Ala Ile Thr Ile Tyr Gly Arg Thr Lys Glu Leu
        130                 135                 140
Ala Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 57
<211> LENGTH: 178
<212> TYPE: PRT
<213> ORGANISM: Artificial Sequence
<220> FEATURE:
<223> OTHER INFORMATION: Description of Artificial Sequence: Synthetic hNGAL mutein polypeptide

<400> SEQUENCE: 57

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Leu Ala Gly Asn Arg Ile Leu Arg Asp Asp Gln His Pro
            35                  40                  45
Met Asn Met Tyr Ala Thr Ile Tyr Glu Leu Lys Glu Asp Lys Ser Tyr
        50                  55                  60
Asn Val Thr Ser Val Ile Ser Ser His Lys Lys Cys Glu Tyr Thr Ile
65                  70                  75                  80
Ala Thr Phe Val Pro Gly Ser Gln Pro Gly Glu Phe Thr Leu Gly Asn
                85                  90                  95
Ile Lys Ser Tyr Gly Asp Lys Thr Ser Tyr Leu Val Arg Val Val Ser
```

```
                100              105              110
Thr Asp Tyr Asn Gln Tyr Ala Val Val Phe Phe Lys Leu Ala Glu Asp
            115                  120                  125

Asn Ala Glu Phe Phe Ala Ile Thr Ile Tyr Gly Arg Thr Lys Glu Leu
    130                  135                  140

Ala Ser Glu Leu Lys Glu Asn Phe Ile Arg Phe Ser Lys Cys Leu Gly
145                  150                  155                 160

Leu Pro Glu Asn His Ile Val Phe Pro Val Pro Ile Asp Gln Cys Ile
                165                  170                  175

Asp Gly

<210> SEQ ID NO 58
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 58

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
50                  55                  60

Asn Val Thr Ser Val Ile Ser Ser His Lys Lys Cys Glu Tyr Thr Ile
65                  70                  75                  80

Ala Thr Phe Val Pro Gly Ser Cys Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                  120                  125

Asn Ala Glu Phe Phe Ala Ile Thr Ile Tyr Gly Arg Thr Lys Glu Leu
    130                  135                  140

Ala Ser Glu Leu Lys Glu Asn Phe Ile Arg Phe Ser Lys Ser Leu Gly
145                  150                  155                 160

Leu Pro Glu Asn His Ile Val Phe Pro Val Pro Ile Asp Gln Cys Ile
                165                  170                  175

Asp Gly

<210> SEQ ID NO 59
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 59

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30
```

```
Val Val Gly Leu Ala Gly Asn Arg Ile Leu Arg Asp Asp Gln His Pro
         35                  40                  45

Met Asn Met Tyr Ala Thr Ile Tyr Glu Leu Lys Cys Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
             85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 60
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 60

Gln Asp Ser Thr Ser Asp Leu Ile Pro Ala Pro Pro Leu Ser Lys Val
 1               5                  10                  15

Pro Leu Gln Gln Cys Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
             85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 61
<211> LENGTH: 178
<212> TYPE: PRT
```

-continued

<213> ORGANISM: Artificial Sequence
<220> FEATURE:
<223> OTHER INFORMATION: Description of Artificial Sequence: Synthetic
      hNGAL mutein polypeptide

<400> SEQUENCE: 61

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Leu Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Arg Ser Tyr Gly Asp Lys Thr Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 62
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 62

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Asp Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
            100                 105                 110

Thr Asp Tyr Asn Gln Tyr Ala Val Val Phe Phe Lys His Ala Asp Ser
        115                 120                 125

Asn Tyr Glu Ser Phe Ser Ile Thr Ile Tyr Gly Arg Thr Lys Glu Leu
    130                 135                 140

```
Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 63
<211> LENGTH: 214
<212> TYPE: PRT
<213> ORGANISM: Artificial Sequence
<220> FEATURE:
<223> OTHER INFORMATION: Description of Artificial Sequence: Synthetic
      arm of multi-specific polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 643
<212> TYPE: PRT
<213> ORGANISM: Artificial Sequence
<220> FEATURE:
<223> OTHER INFORMATION: Description of Artificial Sequence: Synthetic
      arm of multi-specific polypeptide

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
                385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys Gly Gly Gly Gly Ser Gly Gly Gly Gly Ser Gly Gly Gly Gly
```

```
              450                 455                 460
Ser Gln Asp Ser Thr Ser Asp Leu Ile Pro Ala Pro Pro Leu Ser Lys
465                 470                 475                 480

Val Pro Leu Gln Gln Asn Phe Gln Asp Asn Gln Phe His Gly Lys Trp
                485                 490                 495

Tyr Val Val Gly Leu Ala Gly Asn Arg Ile Leu Arg Asp Asp Gln His
                500                 505                 510

Pro Met Pro Met Tyr Ala Thr Ile Tyr Glu Leu Lys Gly Asp Lys Ser
                515                 520                 525

Tyr Gln Val Thr Ser Val Ile Ser Ser His Lys Lys Cys Leu Tyr Pro
                530                 535                 540

Ile Ala Thr Phe Val Pro Gly Ser Gln Pro Gly Glu Phe Thr Leu Gly
545                 550                 555                 560

Asn Ile Lys Ser Tyr Gly Asp Lys Trp Ser Tyr Leu Val Arg Val Val
                565                 570                 575

Ser Thr Asp Tyr Asn Gln Tyr Ala Val Val Phe Phe Lys His Ala Asp
                580                 585                 590

Ser Asn Tyr Glu Ser Phe Ser Ile Thr Ile Tyr Gly Arg Thr Lys Glu
                595                 600                 605

Leu Ala Ser Glu Leu Lys Glu Asn Phe Ile Arg Phe Ser Lys Ser Leu
                610                 615                 620

Gly Leu Pro Glu Asn His Ile Val Phe Pro Val Pro Ile Asp Gln Cys
625                 630                 635                 640

Ile Asp Gly

<210> SEQ ID NO 65
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 65

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Arg Ile Leu Arg Asp Asp Gln His Pro
            35                  40                  45

Met Pro Met Tyr Ala Thr Ile Tyr Glu Leu Lys Glu Asp Lys Ser Tyr
50                  55                  60

Gln Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
                100                 105                 110

Thr Asn Tyr Asn Gln His Ala Met Val Phe Phe Lys His Ala Asp Ser
                115                 120                 125

Asn Tyr Glu Ser Phe Ser Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

```
                        165                 170                 175

Asp Gly Ser Ala Trp Ser His Pro Gln Phe Glu Lys
            180                 185

<210> SEQ ID NO 66
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 66

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Leu Asp Gln His Pro
        35                  40                  45

Met Pro Met Tyr Ala Thr Ile Tyr Glu Leu Lys Glu Asp Lys Ser Tyr
    50                  55                  60

Gln Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Arg Ser Tyr Gly Asp Lys Thr Ser Tyr Leu Val Arg Val Val Ser
            100                 105                 110

Thr Asn Tyr Asn Gln His Ala Met Val Phe Phe Lys His Ala Asp Thr
        115                 120                 125

Asn Tyr Glu Ser Phe Ser Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 67
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 67

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Tyr Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Ser Ile
65                  70                  75                  80

Ala Thr Phe Val Pro Gly Ser Gln Ala Gly Glu Phe Thr Leu Gly Asn
```

```
            85                  90                  95
Ile Lys Ser Tyr Gly Asp Lys Glu Ser Tyr Leu Val Arg Val Val Ser
            100                 105                 110

Thr Asp Tyr Asn Gln Tyr Ala Val Val Phe Phe Lys Tyr Ala Gly His
            115                 120                 125

Asn Phe Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 68
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 68

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Arg Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Leu Ser Tyr Leu Val Arg Val Val Ser
            100                 105                 110

Thr Asp Tyr Asn Gln Tyr Ala Val Val Phe Phe Lys Tyr Ala Gly Asp
            115                 120                 125

Asn Phe Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 69
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 69

Gln Asp Ser Thr Ser Asp Leu Ile Pro Ala Pro Pro Leu Ser Lys Val
```

```
              1               5                  10                 15
    Pro Leu Gln Gln Asn Phe Gln Asp Asn Gln Phe His Gly Lys Trp Tyr
                    20                  25                  30

Val Val Gly Leu Ala Gly Asn Arg Ile Leu Arg Asn Asp Gln His Pro
                    35                  40                  45

Met Pro Met Tyr Ala Thr Ile Tyr Glu Leu Lys Gly Asp Lys Ser Tyr
            50                  55                  60

Asn Val Thr Ser Val Ile Ser Ser His Lys Lys Cys Leu Tyr Thr Ile
     65                  70                  75                  80

Ala Thr Phe Val Pro Gly Ser Gln Pro Gly Glu Phe Thr Leu Gly Asn
                    85                  90                  95

Ile Lys Ser Tyr Gly Asp Lys Phe Ser Tyr Leu Val Arg Val Val Ser
                    100                 105                 110

Thr Asp Tyr Asn Gln Tyr Ala Val Val Phe Phe Lys Leu Ala Asp Ser
                    115                 120                 125

Asn Ser Glu Ser Phe Ser Ile Thr Ile Tyr Gly Arg Thr Lys Glu Leu
                    130                 135                 140

Ala Ser Glu Leu Lys Glu Asn Phe Ile Arg Phe Ser Lys Ser Leu Gly
    145                 150                 155                 160

Leu Pro Glu Asn His Ile Val Phe Pro Val Pro Ile Asp Gln Cys Ile
                    165                 170                 175

Asp Gly Ser Ala Trp Ser His Pro Gln Phe Glu Lys
                    180                 185
```

<210> SEQ ID NO 70
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 70

```
    Gln Asp Ser Thr Ser Asp Leu Ile Pro Ala Pro Pro Leu Ser Lys Val
    1               5                   10                  15

Pro Leu Gln Gln Asn Phe Gln Asp Asn Gln Phe His Gly Lys Trp Tyr
                    20                  25                  30

Val Val Gly Leu Ala Gly Asn Arg Ile Leu Arg His Asp Gln Tyr Pro
                    35                  40                  45

Met Asp Met Tyr Ala Thr Ile Tyr Glu Leu Lys Gly Asp Lys Ser Tyr
            50                  55                  60

Asn Val Thr Ser Val Ile Ser Ser His Lys Lys Cys Leu Tyr Pro Ile
     65                  70                  75                  80

Ala Thr Phe Val Pro Gly Ser Gln Pro Gly Glu Phe Thr Leu Gly Asn
                    85                  90                  95

Ile Lys Ser Tyr Gly Asp Lys Thr Ser Tyr Leu Val Arg Val Val Ser
                    100                 105                 110

Thr Asp Tyr Asn Gln Tyr Ala Val Val Phe Phe Lys His Ala Asp Thr
                    115                 120                 125

Asn Phe Glu Ser Phe Ser Ile Thr Ile Tyr Gly Arg Thr Lys Glu Leu
                    130                 135                 140

Ala Ser Glu Leu Lys Glu Asn Phe Ile Arg Phe Ser Lys Ser Leu Gly
    145                 150                 155                 160

Leu Pro Glu Asn His Ile Val Phe Pro Val Pro Ile Asp Gln Cys Ile
                    165                 170                 175
```

Asp Gly Ser Ala Trp Ser His Pro Gln Phe Glu Lys
            180                 185

<210> SEQ ID NO 71
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 71

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Ser Ser His Lys Lys Cys Val Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Gly Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 72
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 72

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Thr Asp Gln His Pro
        35                  40                  45

Met Gln Met Tyr Ala Thr Ile Tyr Glu Leu Lys Gly Asp Lys Ser Tyr
50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

```
Ile Lys Ser Tyr Gly Asp Lys Arg Ser His Leu Val Arg Val Val Ser
            100                 105                 110

Thr Asp Tyr Asn Gln Tyr Ala Val Val Phe Phe Lys Arg Ala Asp Phe
        115                 120                 125

Asn Ala Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 73
<211> LENGTH: 188
<212> TYPE: PRT
<213> ORGANISM: Artificial Sequence
<220> FEATURE:
<223> OTHER INFORMATION: Description of Artificial Sequence: Synthetic
    hNGAL mutein polypeptide

<400> SEQUENCE: 73

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asn Asp Gln His Pro
        35                  40                  45

Met Asp Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Met Ser Tyr Leu Val Arg Val Val Ser
            100                 105                 110

Thr Asp Tyr Asn Gln Tyr Ala Val Val Phe Phe Lys Leu Ala Asp His
        115                 120                 125

Asn Tyr Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 74
<211> LENGTH: 188
<212> TYPE: PRT
<213> ORGANISM: Artificial Sequence
<220> FEATURE:
<223> OTHER INFORMATION: Description of Artificial Sequence: Synthetic
    hNGAL mutein polypeptide

<400> SEQUENCE: 74

```
Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
           100                 105                 110

Thr Asp Tyr Asn Gln Tyr Ala Val Val Phe Phe Lys Leu Ala Glu Asp
           115                 120                 125

Asn Ala Glu Phe Phe Ala Ile Thr Ile Tyr Gly Arg Thr Lys Glu Leu
       130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
               165                 170                 175

Asp Gly Ser Ala Trp Ser His Pro Gln Phe Glu Lys
           180                 185

<210> SEQ ID NO 75
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 75

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Gln Asp Gln His Pro
            35                  40                  45

Met Asn Met Tyr Ala Thr Ile Tyr Glu Leu Lys Gly Asp Lys Ser Tyr
 50                  55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
           100                 105                 110

Thr Asp Tyr Asn Gln Tyr Ala Val Val Phe Phe Lys Leu Ala Asp Gly
           115                 120                 125

Asn Ser Glu Ser Phe Ser Ile Thr Ile Tyr Gly Arg Thr Lys Glu Leu
       130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
               165                 170                 175

Asp Gly Ser Ala Trp Ser His Pro Gln Phe Glu Lys
           180                 185
```

<210> SEQ ID NO 76
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 76

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Arg Asp Gln His Pro
        35                  40                  45

Met Ser Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Arg Ser His Leu Val Arg Val Val Ser
            100                 105                 110

Thr Asp Tyr Asn Gln Tyr Ala Val Val Phe Phe Lys Arg Ala Asp Pro
        115                 120                 125

Asn Tyr Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 77
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 77

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Thr Asp Gln His Pro
        35                  40                  45

Met Ser Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Gly Ser His Leu Val Arg Val Val Ser
            100                 105                 110

```
Thr Asp Tyr Asn Gln Tyr Ala Val Val Phe Phe Lys Lys Ala Gly Leu
        115                 120                 125

Asn Ser Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 78
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 78

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Ser Asp Gln His Pro
        35                  40                  45

Met Arg Met Tyr Ala Thr Ile Tyr Glu Leu Lys Gly Asp Lys Ser Tyr
50                  55                  60

Asn Val Thr Ser Val Ile Ser Ser His Lys Lys Cys Leu Tyr Thr Ile
65                  70                  75                  80

Ala Thr Phe Val Pro Gly Ser Gln Thr Gly Glu Phe Thr Leu Gly Asn
                85                  90                  95

Ile Lys Ser Tyr Gly Asp Lys Glu Ser His Leu Val Arg Val Val Ser
            100                 105                 110

Thr Asp Tyr Asn Gln Tyr Ala Val Val Phe Phe Lys Arg Ala Asn Ser
        115                 120                 125

Asn Ser Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 79
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 79

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Leu Ala Gly Asn Arg Ile Leu Arg His Asp Gln His Pro
            35                  40                  45

Met Pro Met Tyr Ala Thr Ile Tyr Glu Leu Lys Gly Asp Lys Ser Tyr
 50                      55                  60

Asn Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Gly Lys Val Ser Tyr Leu Val Arg Val Val Ser
                100                 105                 110

Thr Asp Tyr Asn Gln Tyr Ala Val Val Phe Phe Lys His Ala Gly Pro
            115                 120                 125

Asn Phe Glu Ser Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 80
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 80

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asn Asp Gln His Pro
            35                  40                  45

Met Asn Met Tyr Ala Thr Ile Tyr Glu Leu Lys Gly Asp Lys Ser Tyr
 50                      55                  60

Asn Val Thr Ser Val Ile Ser Ser His Lys Lys Cys Leu Tyr Thr Ile
 65                  70                  75                  80

Ala Thr Phe Val Pro Gly Ser Gln Ala Gly Glu Phe Thr Leu Gly Asn
                 85                  90                  95

Ile Lys Ser Tyr Gly Asp Lys Ile Ser Tyr Leu Val Arg Val Val Ser
                100                 105                 110

Thr Asp Tyr Asn Gln Tyr Ala Val Val Phe Phe Lys His Ala Asp Gly
            115                 120                 125

Asn Ala Glu Ser Phe Ser Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

-continued

```
<210> SEQ ID NO 81
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 81

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Gln Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asp Tyr Asn Gln Tyr Ala Val Val Phe Phe Lys Tyr Ala Asp Arg
        115                 120                 125

Asn Phe Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 82
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 82

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg His Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asp Tyr Asn Gln Tyr Ala Val Val Phe Phe Lys Leu Ala Asp Gln
```

-continued

```
            115                 120                 125
Asn Ser Glu Ser Phe Ser Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 83
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 83

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Tyr Asp Gln His Pro
        35                  40                  45

Met Pro Met Tyr Ala Thr Ile Tyr Glu Leu Lys Gly Asp Lys Ser Tyr
    50                  55                  60

Asn Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Ile Ser Tyr Leu Val Arg Val Val Ser
            100                 105                 110

Thr Asp Tyr Asn Gln Tyr Ala Val Val Phe Phe Lys Tyr Ala Asp Arg
        115                 120                 125

Asn Phe Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 84
<211> LENGTH: 188
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 84

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Met Asp Gln His Pro
```

```
                35                  40                  45
Met Asp Met Tyr Ala Thr Ile Tyr Glu Leu Lys Gly Asp Lys Ser Tyr
 50                      55                  60

Asn Val Thr Ser Val Ile Ser Ser His Lys Lys Cys Leu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser His Leu Val Arg Val Val Ser
            100                 105                 110

Thr Asp Tyr Asn Gln Tyr Ala Val Val Phe Phe Lys Lys Ala Asn Arg
        115                 120                 125

Asn Ser Glu Ser Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 85
<211> LENGTH: 645
<212> TYPE: DNA
<213> ORGANISM: Artificial Sequence
<220> FEATURE:
<223> OTHER INFORMATION: Description of Artificial Sequence: Synthetic
      DNA sequence of arm of multi-specific polypeptide
      shown in SEQ ID NO: 63

<400> SEQUENCE: 85
gacatccaga tgacacagtc tccctcttcc ctgtccgctt ctgtgggcga tcgagtgaca    60
atcacctgta gggctagtca ggatgtgaat actgctgttg cttggtacca gcagaaacca   120
ggaaaagccc ctaaactgct gatctactct gcctcattcc tgtactctgg ggtgccttct   180
cgattcagtg gttctagatc tggcaccgat ttcacactga ccatttcttc actgcaacct   240
gaggattttg ccacctacta ctgtcagcag cactacacaa cacctcccac atttggccag   300
ggcacaaaag tggagatcaa acggaccgtg gcggcgcctt ctgtgttcat tttcccccca   360
tctgatgaac agctgaaatc tggcactgct tctgtggtct gtctgctgaa caacttctac   420
cctagagagg ccaaagtcca gtggaaagtg gacaatgctc tgcagagtgg gaattcccag   480
gaatctgtca ctgagcagga ctctaaggat agcacatact ccctgtcctc tactctgaca   540
ctgagcaagg ctgattacga gaaacacaaa gtgtacgcct gtgaagtcac acatcagggg   600
ctgtctagtc ctgtgaccaa atccttcaat aggggagagt gctga                   645

<210> SEQ ID NO 86
<211> LENGTH: 1929
<212> TYPE: DNA
<213> ORGANISM: Artificial Sequence
<220> FEATURE:
<223> OTHER INFORMATION: Description of Artificial Sequence: Synthetic
      DNA sequence of arm of multi-specific polypeptide shown in
      SEQ ID NO: 64

<400> SEQUENCE: 86
gaagtccagc tggtcgaatc tggtggtggc ctggtccagc tggtggatc actgagactg     60 tcctgtgctg cttctggttt caacatcaag gacacctaca tccattgggt cagacaggca   120
```

```
cctggcaagg gactggaatg ggtcgcccga atctacccta caaacggcta cactcgctac      180
gccgactccg tcaagggacg ctttaccatc tccgccgaca cctctaaaaa caccgcctac      240
ctgcagatga atagtctgag ggccgaggat actgctgtgt actactgctc acgatgggga      300
ggcgacggct tttacgctat ggattactgg ggacagggaa ctctggtcac tgtgtctagc      360
gctagcacaa agggccctag tgtgtttcct ctggctccct cttccaaatc cacttctggt      420
ggcactgctg ctctgggatg cctggtgaag gattactttc ctgaacctgt gactgtctca      480
tggaactctg gtgctctgac ttctggtgtc cacactttcc ctgctgtgct gcagtctagt      540
ggactgtact ctctgtcatc tgtggtcact gtgccctctt catctctggg aacccagacc      600
tacatttgta atgtgaacca caaaccatcc aacactaaag tggacaaaaa agtggaaccc      660
aaatcctgtg acaaaaccca cacctgccca ccttgtcctg ccctgaact gctgggagga       720 ccttctgtgt ttctgttccc accaaaacca aagatacc tgatgatctc tagaaccct        780 gaggtgacat gtgtggtggt ggatgtgtct catgaggacc ctgaggtcaa attcaactgg      840
tacgtggatg gagtggaagt ccacaatgcc aaaaccaagc ctagagagga acagtacaat      900
tcaacctaca gagtggtcag tgtgctgact gtgctgcatc aggattggct gaatggcaag      960
gaatacaagt gtaaagtctc aaacaaggcc ctgcctgctc caattgagaa aacaatctca     1020
aaggccaagg gacagcctag ggaaccccag gtctacaccc tgccaccttc aagagaggaa     1080
atgaccaaaa accaggtgtc cctgacatgc ctggtcaaag cttctaccc ttctgacatt      1140 gctgtggagt gggagtcaaa tggacagcct gagaacaact acaaaacaac ccccctgtg      1200 ctggattctg atggctcttt ctttctgtac tccaaactga ctgtggacaa gtctagatgg     1260
cagcagggga atgtcttttc ttgctctgtc atgcatgagg ctctgcataa ccactacact     1320
cagaaatccc tgtctctgtc tcctggcaaa ggcggcggag gatccggggg tgggggaagc     1380
ggcggaggag gtagccagga ctctaccagt gatctgatcc cagcaccacc tctgtccaag     1440
gtgcccctgc agcagaactt ccaggacaat cagtttcacg ggaagtggta tgttgtcggc     1500
ctggcaggaa acagaatcct gcgggacgat cagcatccaa tgccgatgta cgccacaatc     1560
tacgagctga agggagataa aagttaccaa gtgacttcag tcatctccag ccacaagaaa     1620
tgcctgtatc ctattgctac tttcgtgccc gggtctcagc ctggcgagtt caccctgggc     1680
aacatcaagt cctacggaga caaatggagc tatcttgtga gggtggtctc taccgattac     1740
aaccagtatg ccgtggtctt ctttaagcac gctgacagta attacgagtc attctccatc     1800
accatctacg gcagaacaaa ggaactggca tccgagctga aaaaacttt catcaggttt     1860 agcaagtctc tggggctgcc agagaatcat attgtgtttc ctgtcccaat cgaccagtgt     1920
attgatggt                                                             1929
```

<210> SEQ ID NO 87
<211> LENGTH: 178
<212> TYPE: PRT
<213> ORGANISM: Artificial Sequence
<220> FEATURE:
<223> OTHER INFORMATION: Description of Artificial Sequence: Synthetic
    hNGAL mutein polypeptide

<400> SEQUENCE: 87

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

```
Val Val Gly Leu Ala Gly Asn Arg Ile Leu Arg Tyr Asp Gln His Pro
         35                  40                  45

Met Pro Met Tyr Ala Thr Ile Tyr Glu Leu Lys Gly Asp Lys Ser Tyr
 50                  55                  60

Gln Val Thr Ser Val Ile Ser Ser His Lys Lys Cys Leu Tyr Ser Ile
 65                  70                  75                  80

Ala Thr Phe Val Pro Gly Ser Gln Ala Gly Glu Phe Thr Leu Gly Asn
                 85                  90                  95

Ile Lys Ser Tyr Gly Asp Lys Glu Ser Tyr Leu Val Arg Val Val Ser
             100                 105                 110

Thr Asp Tyr Asn Gln Tyr Ala Val Val Phe Lys Tyr Ala Gly His
             115                 120                 125

Asn Phe Glu Ser Phe Ser Ile Thr Ile Tyr Gly Arg Thr Lys Glu Leu
 130                 135                 140

Ala Ser Glu Leu Lys Glu Asn Phe Ile Arg Phe Ser Lys Ser Leu Gly
 145                 150                 155                 160

Leu Pro Glu Asn His Ile Val Phe Pro Val Pro Ile Asp Gln Cys Ile
                 165                 170                 175

Asp Gly

<210> SEQ ID NO 88
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 88

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Arg Ile Leu Arg Asp Asp Gln His Pro
         35                  40                  45

Met Arg Met Tyr Ala Thr Ile Tyr Glu Leu Lys Gly Asp Lys Ser Tyr
 50                  55                  60

Gln Val Thr Ser Val Ile Ser Ser His Lys Lys Cys Leu Tyr Pro Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Leu Ser Tyr Leu Val Arg Val Val Ser
             100                 105                 110

Thr Asp Tyr Asn Gln Tyr Ala Val Val Phe Lys Tyr Ala Gly Asp
             115                 120                 125

Asn Phe Glu Ser Phe Ser Ile Thr Ile Tyr Gly Arg Thr Lys Glu Leu
 130                 135                 140

Ala Ser Glu Leu Lys Glu Asn Phe Ile Arg Phe Ser Lys Ser Leu Gly
 145                 150                 155                 160

Leu Pro Glu Asn His Ile Val Phe Pro Val Pro Ile Asp Gln Cys Ile
                 165                 170                 175

Asp Gly

<210> SEQ ID NO 89
<211> LENGTH: 178
<212> TYPE: PRT
```

<213> ORGANISM: Artificial Sequence
<220> FEATURE:
<223> OTHER INFORMATION: Description of Artificial Sequence: Synthetic
     hNGAL mutein polypeptide

<400> SEQUENCE: 89

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Asn Asp Gln His Pro
        35                  40                  45

Met Pro Met Tyr Ala Thr Ile Tyr Glu Leu Lys Gly Asp Lys Ser Tyr
    50                  55                  60

Gln Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Phe Ser Tyr Leu Val Arg Val Val Ser
            100                 105                 110

Thr Asp Tyr Asn Gln Tyr Ala Val Val Phe Phe Lys Leu Ala Asp Ser
        115                 120                 125

Asn Ser Glu Ser Phe Ser Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 90
<211> LENGTH: 178
<212> TYPE: PRT
<213> ORGANISM: Artificial Sequence
<220> FEATURE:
<223> OTHER INFORMATION: Description of Artificial Sequence: Synthetic
     hNGAL mutein polypeptide

<400> SEQUENCE: 90

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Ser Asp Gln His Pro
        35                  40                  45

Met Arg Met Tyr Ala Thr Ile Tyr Glu Leu Lys Gly Asp Lys Ser Tyr
    50                  55                  60

Gln Val Thr Ser Val Ile Ser Ser His Lys Lys Cys Leu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Trp Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Tyr Glu Ser Phe Ser Ile Thr Ile Tyr Gly Arg Thr Lys Glu Leu
130                 135                 140

```
Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 91
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 91

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg His Asp Gln Tyr Pro
        35                  40                  45

Met Asp Met Tyr Ala Thr Ile Tyr Glu Leu Lys Gly Asp Lys Ser Tyr
    50                  55                  60

Gln Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys His Ala Asp Thr
        115                 120                 125

Asn Phe Glu Ser Phe Ser Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 92
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 92

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Thr Asp Gln His Pro
        35                  40                  45

Met Gln Met Tyr Ala Thr Ile Tyr Glu Leu Lys Gly Asp Lys Ser Tyr
    50                  55                  60

Gln Val Thr Ser Val Ile Ser Ser His Lys Lys Cys Leu Tyr Thr Ile
```

```
                65                  70                  75                  80
Ala Thr Phe Val Pro Gly Ser Gln Pro Gly Glu Phe Thr Leu Gly Asn
                        85                  90                  95

Ile Lys Ser Tyr Gly Asp Lys Arg Ser His Leu Val Arg Val Val Ser
                100                 105                 110

Thr Asp Tyr Asn Gln Tyr Ala Val Val Phe Phe Lys Arg Ala Asp Phe
                115                 120                 125

Asn Ala Glu Ser Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 93
<211> LENGTH: 1929
<212> TYPE: DNA
<213> ORGANISM: Artificial Sequence
<220> FEATURE:
<223> OTHER INFORMATION: Description of Artificial Sequence: Synthetic
      DNA sequence for arm of multi-specific polypeptide
      (SEQ ID NO. 97)

<400> SEQUENCE: 93
```

| | | | | | |
|---|---|---|---|---|---|
| gaagtccagc | tggtcgaatc | tggtggtggc | ctggtccagc | ctggtggatc | actgagactg | 60 |
| tcctgtgctg | cttctggttt | caacatcaag | gacacctaca | tccattgggt | cagacaggca | 120 |
| cctggcaagg | gactggaatg | ggtcgcccga | atctacccta | caaacggcta | cactcgctac | 180 |
| gccgactccg | tcaagggacg | ctttaccatc | tccgccgaca | cctctaaaaa | caccgcctac | 240 |
| ctgcagatga | atagtctgag | ggccgaggat | actgctgtgt | actactgctc | acgatgggga | 300 |
| ggcgacggct | tttacgctat | ggattactgg | ggacagggaa | ctctggtcac | tgtgtctagc | 360 |
| gctagcacaa | agggccctag | tgtgtttcct | ctggctccct | cttccaaatc | cacttctggt | 420 |
| ggcactgctg | ctctgggatg | cctggtgaag | gattactttc | ctgaacctgt | gactgtctca | 480 |
| tggaactctg | gtgctctgac | ttctggtgtc | cacacttttc | ctgctgtgct | gcagtctagt | 540 |
| ggactgtact | ctctgtcatc | tgtggtcact | gtgccctctt | catctctggg | aacccagacc | 600 |
| tacatttgta | atgtgaacca | caaccatccc | aacactaaag | tggacaaaaa | agtggaaccc | 660 |
| aaatcctgtg | acaaaaccca | cacctgccca | ccttgtcctg | ccctgaact  | gctgggagga | 720 |
| ccttctgtgt | ttctgttccc | accaaaacca | aaagatacccc | tgatgatctc | tagaacccct | 780 |
| gaggtgacat | gtgtggtggt | ggatgtgtct | catgaggacc | ctgaggtcaa | attcaactgg | 840 |
| tacgtggatg | gagtggaagt | ccacaatgcc | aaaaccaagc | ctagagagga | acagtacaat | 900 |
| tcaacctaca | gagtggtcag | tgtgctgact | gtgctgcatc | aggattggct | gaatggcaag | 960 |
| gaatacaagt | gtaaagtctc | aaacaaggcc | ctgcctgctc | caattgagaa | aacaatctca | 1020 |
| aaggccaagg | gacagcctag | ggaaccccag | gtctacaccc | tgccaccttc | aagagaggaa | 1080 |
| atgaccaaaa | accaggtgtc | cctgacatgc | ctggtcaaag | gcttctaccc | ttctgacatt | 1140 |
| gctgtggagt | gggagtcaaa | tggacagcct | gagaacaact | acaaaacaac | ccccctgtg  | 1200 |
| ctggattctg | atggctcttt | cttcctgtac | tccaaactga | ctgtggacaa | gtctagatgg | 1260 |
| cagcagggga | atgtcttttc | ttgctctgtc | atgcatgagg | ctctgcataa | ccactacact | 1320 |
| cagaaatccc | tgtctctgtc | tcctggcaaa | ggcggcggag | gatccggggg | tggggaagc  | 1380 |

```
ggcggaggag gtagccagga ctccaccagt gaccttatcc cggctccccc cctgtcaaaa   1440
gtaccactac agcaaaattt ccaggacaac cagtttcagg gcaaatggta cgttgttgga   1500
ctggcaggga acagaattct gcgccaggac cagcatccta tgctcatgta tgctaccatt   1560
tatgaactca aggaggacaa atcctaccaa gtgacctctg tgattagtag ccataagaag   1620
tgcctctatc caatcgccac attcgtgccc ggttctcagc ccggcgaatt tacactcggg   1680
aacatcaagt cttatggaga caaagtcagt tatttggttc gagtggtatc tacaaattac   1740
aatcagcacg caatggtctt cttcaaacat gcggatacaa attatgaaag tttctccatc   1800
accctctacg gaaggaccaa agagcttacc agcgagctga aggaaaactt tatacgattt   1860
tccaaatcct taggcctccc tgaaaatcac atcgtgtttc ccgttccgat tgatcagtgt   1920
atcgacggg                                                           1929
```

<210> SEQ ID NO 94
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 94

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Arg Ile Leu Arg Gln Asp Gln His Pro
        35                  40                  45

Met Pro Met Tyr Ala Thr Ile Tyr Glu Leu Lys Glu Asp Lys Ser Tyr
    50                  55                  60

Gln Val Thr Ser Val Ile Ser Ser His Lys Lys Cys Leu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Val Ser Tyr Leu Val Arg Val Val Ser
            100                 105                 110

Thr Asn Tyr Asn Gln His Ala Met Val Phe Phe Lys Tyr Ala Asp Arg
        115                 120                 125

Asn Phe Glu Ser Phe Ser Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 95
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein polypeptide

<400> SEQUENCE: 95

```
Gln Asp Ser Thr Ser Asp Leu Ile Pro Ala Pro Pro Leu Ser Lys Val
```

```
              1               5                  10                 15
         Pro Leu Gln Gln Asn Phe Gln Asp Asn Gln Phe Gln Gly Lys Trp Tyr
                          20                  25                  30

Val Val Gly Leu Ala Gly Asn Arg Ile Leu Arg Gln Asp Gln His Pro
                          35                  40                  45

Met Leu Met Tyr Ala Thr Ile Tyr Glu Leu Lys Glu Asp Lys Ser Tyr
                  50                  55                  60

Gln Val Thr Ser Val Ile Ser Ser His Lys Lys Cys Leu Tyr Pro Ile
         65                  70                  75                  80

Ala Thr Phe Val Pro Gly Ser Gln Pro Gly Glu Phe Thr Leu Gly Asn
                              85                  90                  95

Ile Lys Ser Tyr Gly Asp Lys Val Ser Tyr Leu Val Arg Val Val Ser
                         100                 105                 110

Thr Asn Tyr Asn Gln His Ala Met Val Phe Phe Lys His Ala Asp Thr
                         115                 120                 125

Asn Tyr Glu Ser Phe Ser Ile Thr Leu Tyr Gly Arg Thr Lys Glu Leu
                 130                 135                 140

Thr Ser Glu Leu Lys Glu Asn Phe Ile Arg Phe Ser Lys Ser Leu Gly
         145                 150                 155                 160

Leu Pro Glu Asn His Ile Val Phe Pro Val Pro Ile Asp Gln Cys Ile
                             165                 170                 175

Asp Gly
```

<210> SEQ ID NO 96
<211> LENGTH: 1350
<212> TYPE: DNA
<213> ORGANISM: Artificial Sequence
<220> FEATURE:
<223> OTHER INFORMATION: Description of Artificial Sequence: Synthetic
      DNA sequence for arm of multi-specific polypeptide
      (SEQ ID NO: 98)

<400> SEQUENCE: 96

```
gaagtccagc tggtcgaatc tggtggtggc ctggtccagc ctggtggatc actgagactg      60
tcctgtgctg cttctggttt caacatcaag gacacctaca tccattgggt cagacaggca     120
cctggcaagg gactggaatg ggtcgcccga atctacccta caaacggcta cactcgctac     180
gccgactccg tcaagggacg ctttaccatc tccgccgaca cctctaaaaa caccgcctac     240
ctgcagatga atagtctgag ggccgaggat actgctgtgt actactgctc acgatgggga     300
ggcgacggct tttacgctat ggattactgg ggacagggaa ctctggtcac tgtgtctagc     360
gctagcacaa agggccctag tgtgttcct ctggctccct cttccaaatc cacttctggt     420
ggcactgctg ctctgggatg cctggtgaag gattactttc ctgaacctgt gactgtctca     480
tggaactctg gtgctctgac ttctggtgtc cacactttcc ctgctgtgct gcagtctagt     540
ggactgtact ctctgtcatc tgtggtcact gtgccctctt catctctggg aacccagacc     600
tacatttgta atgtgaacca caaaccatcc aacactaaag tggacaaaaa agtggaaccc     660
aaatcctgtg acaaaaccca cacctgccca ccttgtcctg ccctgaact gctgggagga     720
ccttctgtgt ttctgttccc accaaaacca aagataccc tgatgatctc tagaacccct     780
gaggtgacat gtgtggtggt ggatgtgtct catgaggacc ctgaggtcaa attcaactgg     840
tacgtggatg gagtggaagt ccacaatgcc aaaaccaagc ctagagagga acagtacaat     900
tcaacctaca gagtggtcag tgtgctgact gtgctgcatc aggattggct gaatggcaag     960
gaatacaagt gtaaagtctc aaacaaggcc ctgcctgctc aattgagaa aacaatctca    1020
```

-continued

| | |
|---|---|
| aaggccaagg gacagcctag ggaaccccag gtctacaccc tgccaccttc aagagaggaa | 1080 |
| atgaccaaaa accaggtgtc cctgacatgc ctggtcaaag gcttctaccc ttctgacatt | 1140 |
| gctgtggagt gggagtcaaa tggacagcct gagaacaact acaaaacaac cccccctgtg | 1200 |
| ctggattctg atggctcttt ctttctgtac tccaaactga ctgtggacaa gtctagatgg | 1260 |
| cagcaggga atgtcttttc ttgctctgtc atgcatgagg ctctgcataa ccactacact | 1320 |
| cagaaatccc tgtctctgtc tcctggcaaa | 1350 |

<210> SEQ ID NO 97
<211> LENGTH: 643
<212> TYPE: PRT
<213> ORGANISM: Artificial Sequence
<220> FEATURE:
<223> OTHER INFORMATION: Description of Artificial Sequence: Synthetic
    Arm of multi-specific polypeptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

```
            290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Gly Gly Gly Gly
    450                 455                 460

Ser Gln Asp Ser Thr Ser Asp Leu Ile Pro Ala Pro Pro Leu Ser Lys
465                 470                 475                 480

Val Pro Leu Gln Gln Asn Phe Gln Asp Asn Gln Phe Gln Gly Lys Trp
                485                 490                 495

Tyr Val Val Gly Leu Ala Gly Asn Arg Ile Leu Arg Gln Asp Gln His
            500                 505                 510

Pro Met Leu Met Tyr Ala Thr Ile Tyr Glu Leu Lys Glu Asp Lys Ser
        515                 520                 525

Tyr Gln Val Thr Ser Val Ile Ser Ser His Lys Lys Cys Leu Tyr Pro
    530                 535                 540

Ile Ala Thr Phe Val Pro Gly Ser Gln Pro Gly Glu Phe Thr Leu Gly
545                 550                 555                 560

Asn Ile Lys Ser Tyr Gly Asp Lys Val Ser Tyr Leu Val Arg Val Val
                565                 570                 575

Ser Thr Asn Tyr Asn Gln His Ala Met Val Phe Phe Lys His Ala Asp
            580                 585                 590

Thr Asn Tyr Glu Ser Phe Ser Ile Thr Leu Tyr Gly Arg Thr Lys Glu
        595                 600                 605

Leu Thr Ser Glu Leu Lys Glu Asn Phe Ile Arg Phe Ser Lys Ser Leu
    610                 615                 620

Gly Leu Pro Glu Asn His Ile Val Phe Pro Val Pro Ile Asp Gln Cys
625                 630                 635                 640

Ile Asp Gly

<210> SEQ ID NO 98
<211> LENGTH: 450
<212> TYPE: PRT
<213> ORGANISM: Artificial Sequence
<220> FEATURE:
<223> OTHER INFORMATION: Description of Artificial Sequence: Synthetic
      Arm of multi-specific polypeptide

<400> SEQUENCE: 98

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430
```

-continued

```
Glu Ala Leu His Asn His Tyr Thr Gln Lys Ser Leu Ser Leu Ser Pro
        435                 440                 445

Gly Lys
    450

<210> SEQ ID NO 99
<211> LENGTH: 407
<212> TYPE: PRT
<213> ORGANISM: Artificial Sequence
<220> FEATURE:
<223> OTHER INFORMATION: Description of Artificial Sequence: Synthetic
      Arm of multi-specific polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

Gln Gly Lys Trp Tyr Val Val Gly Leu Ala Gly Asn Arg Ile Leu Arg
            260                 265                 270

Gln Asp Gln His Pro Met Leu Met Tyr Ala Thr Ile Tyr Glu Leu Lys
        275                 280                 285

Glu Asp Lys Ser Tyr Gln Val Thr Ser Val Ile Ser Ser His Lys Lys
    290                 295                 300

Cys Leu Tyr Pro Ile Ala Thr Phe Val Pro Gly Ser Gln Pro Gly Glu
305                 310                 315                 320

Phe Thr Leu Gly Asn Ile Lys Ser Tyr Gly Asp Lys Val Ser Tyr Leu
```

325                 330                 335
Val Arg Val Val Ser Thr Asn Tyr Asn Gln His Ala Met Val Phe Phe
                340                 345                 350

Lys His Ala Asp Thr Asn Tyr Glu Ser Phe Ser Ile Thr Leu Tyr Gly
            355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 100
<211> LENGTH: 420
<212> TYPE: PRT
<213> ORGANISM: Artificial Sequence
<220> FEATURE:
<223> OTHER INFORMATION: Description of Artificial Sequence: Synthetic
      positive control polypeptide

<400> SEQUENCE: 100

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Gln Asp Ser Thr Ser Asp Leu Ile Pro Ala Pro Pro Leu Ser
                245                 250                 255

Lys Val Pro Leu Gln Gln Asn Phe Gln Asp Asn Gln Phe Gln Gly Lys
            260                 265                 270

-continued

```
Trp Tyr Val Val Gly Leu Ala Gly Asn Arg Ile Leu Arg Gln Asp Gln
            275                 280                 285
His Pro Met Leu Met Tyr Ala Thr Ile Tyr Glu Leu Lys Glu Asp Lys
        290                 295                 300
Ser Tyr Gln Val Thr Ser Val Ile Ser Ser His Lys Lys Cys Leu Tyr
305                 310                 315                 320
Pro Ile Ala Thr Phe Val Pro Gly Ser Gln Pro Gly Glu Phe Thr Leu
                325                 330                 335
Gly Asn Ile Lys Ser Tyr Gly Asp Lys Val Ser Tyr Leu Val Arg Val
            340                 345                 350
Val Ser Thr Asn Tyr Asn Gln His Ala Met Val Phe Phe Lys His Ala
        355                 360                 365
Asp Thr Asn Tyr Glu Ser Phe Ser Ile Thr Leu Tyr Gly Arg Thr Lys
    370                 375                 380
Glu Leu Thr Ser Glu Leu Lys Glu Asn Phe Ile Arg Phe Ser Lys Ser
385                 390                 395                 400
Leu Gly Leu Pro Glu Asn His Ile Val Phe Pro Val Pro Ile Asp Gln
                405                 410                 415
Cys Ile Asp Gly
            420

<210> SEQ ID NO 101
<211> LENGTH: 178
<212> TYPE: PRT
<213> ORGANISM: Artificial Sequence
<220> FEATURE:
<223> OTHER INFORMATION: Description of Artificial Sequence: Synthetic
      hNGAL mutein control polypeptide

<400> SEQUENCE: 101

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Ser Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
Asn Arg Glu Tyr Phe Lys Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 102
<211> LENGTH: 1221
```

<212> TYPE: DNA
<213> ORGANISM: Artificial Sequence
<220> FEATURE:
<223> OTHER INFORMATION: Description of Artificial Sequence: Synthetic
      DNA sequence for arm of multi-specific polypeptide
      (SEQ ID NO: 99)

<400> SEQUENCE: 102

```
gacatccaga tgacacagtc tccctcttcc ctgtccgctt ctgtgggcga tcgagtgaca    60
atcacctgta gggctagtca ggatgtgaat actgctgttg cttggtacca gcagaaacca   120
ggaaaagccc ctaaactgct gatctactct gcctcattcc tgtactctgg ggtgccttct   180
cgattcagtg gttctagatc tggcaccgat ttcacactga ccatttcttc actgcaacct   240
gaggattttg ccacctacta ctgtcagcag cactacacaa cacctcccac atttggccag   300
ggcacaaaag tggagatcaa acggaccgtg gcggcgcctt ctgtgttcat tttcccccca   360
tctgatgaac agctgaaatc tggcactgct tctgtggtct gtctgctgaa caacttctac   420
cctagagagc caaagtcca gtggaaagtg acaatgctc tgcagagtgg aattcccag     480
gaatctgtca ctgagcagga ctctaaggat agcacatact ccctgtcctc tactctgaca   540
ctgagcaagg ctgattacga gaaacacaaa gtgtacgcct gtgaagtcac acatcagggg   600
ctgtctagtc ctgtgaccaa atccttcaat aggggagagt gcggcggcgg aggatccggg   660
ggtgggggaa gcggcggagg aggtagccag gactccacca gtgaccttat cccggctccc   720
cccctgtcaa aagtaccact acagcaaaat tccaggaca accagtttca gggcaaatgg   780
tacgttgttg gactggcagg gaacagaatt ctgcgccagg accagcatcc tatgctcatg   840
tatgctacca tttatgaact caaggaggac aaatcctacc aagtgacctc tgtgattagt   900
agccataaga agtgcctcta tccaatcgcc acattcgtgc ccggttctca gcccggcgaa   960
tttacactcg ggaacatcaa gtcttatgga gacaaagtca gttatttggt tcgagtggta  1020
tctacaaatt acaatcagca cgcaatggtc ttcttcaaac atgcgggatac aaattatgaa  1080
agtttctcca tcaccctcta cggaaggacc aaagagctta ccagcgagct gaaggaaaac  1140
tttatacgat tttccaaatc cttaggcctc cctgaaaatc acatcgtgtt tcccgttccg  1200
attgatcagt gtatcgacgg g                                            1221
```

<210> SEQ ID NO 103
<211> LENGTH: 214
<212> TYPE: PRT
<213> ORGANISM: Artificial Sequence
<220> FEATURE:
<223> OTHER INFORMATION: Description of Artificial Sequence: Synthetic
      multispecific polypeptide (reference molecule)

<400> SEQUENCE: 103

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95
```

```
Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 104
<211> LENGTH: 449
<212> TYPE: PRT
<213> ORGANISM: Artificial Sequence
<220> FEATURE:
<223> OTHER INFORMATION: Description of Artificial Sequence: Synthetic multispecific polypeptide (reference molecule)

<400> SEQUENCE: 104

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
            225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

<210> SEQ ID NO 105
<211> LENGTH: 642
<212> TYPE: PRT
<213> ORGANISM: Artificial Sequence
<220> FEATURE:
<223> OTHER INFORMATION: Description of Artificial Sequence: Synthetic
      multispecific polypeptide (reference molecule)

<400> SEQUENCE: 105

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
```

-continued

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gln Asp Ser Thr Ser Asp Leu Ile Pro Ala Pro Pro Leu Ser Lys Val
465                 470                 475                 480

Pro Leu Gln Gln Asn Phe Gln Asp Asn Gln Phe Gln Gly Lys Trp Tyr
                485                 490                 495

Val Val Gly Leu Ala Gly Asn Arg Ile Leu Arg Gln Asp Gln His Pro
            500                 505                 510

Met Leu Met Tyr Ala Thr Ile Tyr Glu Leu Lys Glu Asp Lys Ser Tyr
        515                 520                 525

Gln Val Thr Ser Val Ile Ser Ser His Lys Lys Cys Leu Tyr Pro Ile
    530                 535                 540

Ala Thr Phe Val Pro Gly Ser Gln Pro Gly Glu Phe Thr Leu Gly Asn
545                 550                 555                 560
```

```
Ile Lys Ser Tyr Gly Asp Lys Val Ser Tyr Leu Val Arg Val Ser
            565                 570                 575
Thr Asn Tyr Asn Gln His Ala Met Val Phe Phe Lys His Ala Asp Thr
            580                 585                 590
Asn Tyr Glu Ser Phe Ser Ile Thr Leu Tyr Gly Arg Thr Lys Glu Leu
            595                 600                 605
Thr Ser Glu Leu Lys Glu Asn Phe Ile Arg Phe Ser Lys Ser Leu Gly
    610                 615                 620
Leu Pro Glu Asn His Ile Val Phe Pro Val Pro Ile Asp Gln Cys Ile
625                 630                 635                 640
Asp Gly

<210> SEQ ID NO 106
<211> LENGTH: 651
<212> TYPE: DNA
<213> ORGANISM: Artificial Sequence
<220> FEATURE:
<223> OTHER INFORMATION: Description of Artificial Sequence: Synthetic
      DNA sequence coding for multispecific polypeptide
      of SEQ ID NO: 103

<400> SEQUENCE: 106
gacatcctgc tgacccagtc ccccgtgatc ctgtccgtgt ctcctggcga gcgggtgtcc      60
ttcagctgca gagcctctca gtccatcggc accaacatcc actggtatca gcagcggacc     120
aacggctccc ctcggctgct gattaagtac gcctccgagt ctatctccgg catcccctcc     180
cgcttctccg gctctggctc tggcaccgac ttcaccctgt ccatcaactc cgtggaatcc     240
gaggatatcg ccgactacta ctgccagcag aacaacaact ggcccaccac cttcggcgct     300
ggcaccaagc tggaactgaa gcggactgtc gcggcgcctt ctgtgttcat tttcccccca     360
tctgatgaac agctgaaatc tggcactgct tctgtggtct gtctgctgaa caacttctac     420
cctagagagg ccaaagtcca gtggaaagtg acaatgctc tgcagagtgg gaattcccag      480
gaatctgtca ctgagcagga ctctaaggat agcacatact ccctgtcctc tactctgaca     540
ctgagcaagg ctgattacga gaaacacaaa gtgtacgcct gtgaagtcac acatcagggg     600
ctgtctagtc ctgtgaccaa atccttcaat aggggagagt gctgatagta a              651

<210> SEQ ID NO 107
<211> LENGTH: 1353
<212> TYPE: DNA
<213> ORGANISM: Artificial Sequence
<220> FEATURE:
<223> OTHER INFORMATION: Description of Artificial Sequence: Synthetic
      DNA sequence coding for multispecific polypeptide
      of SEQ ID NO: 104

<400> SEQUENCE: 107
caggtgcagc tgaagcagtc tggccctgga ctggtgcagc cttcccagtc cctgtccatc      60
acctgtaccg tgtccggctt ctccctgacc aactacggcg tgcactgggt gcgacagtct     120
ccaggcaagg gcctggaatg gctgggagtg atttggagcg gcggcaacac cgactacaac     180
acccctttca cctcccggct gagcatcaac aaggacaact ccaagtccca ggtgttcttc     240
aagatgaact ccctgcagtc caacgacacc gccatctact actgcgccag agccctgacc     300
tactatgact acgagttcgc ctactggggc cagggcaccc tcgtgacagt gtctgctgct     360
agcacaaagg gccctagtgt gtttcctctg gctccctctt ccaaatccac ttctggtggc     420
actgctgctc tgggatgcct ggtgaaggat tactttcctg aacctgtgac tgtctcatgg     480
```

```
aactctggtg ctctgacttc tggtgtccac actttccctg ctgtgctgca gtctagtgga    540
ctgtactctc tgtcatctgt ggtcactgtg ccctcttcat ctctgggaac ccagacctac    600
atttgtaatg tgaaccacaa accatccaac actaaagtgg acaaaaaagt ggaacccaaa    660
tcctgtgaca aaaccacac ctgcccacct tgtcctgccc ctgaactgct gggaggacct     720
tctgtgtttc tgttcccacc aaaaccaaaa gatacccctga tgatctctag aacccctgag   780
gtgacatgtg tggtggtgga tgtgtctcat gaggaccctg aggtcaaatt caactggtac    840
gtggatggag tggaagtcca caatgccaaa accaagccta gagaggaaca gtacaattca    900
acctacagag tggtcagtgt gctgactgtg ctgcatcagg attggctgaa tggcaaggaa    960
tacaagtgta aagtctcaaa caaggccctg cctgctccaa ttgagaaaac aatctcaaag   1020
gccaagggac agcctaggga accccaggtc tacaccctgc caccttcaag agaggaaatg   1080
accaaaaacc aggtgtccct gacatgcctg gtcaaaggct tctacccttc tgacattgct   1140
gtggagtggg agtcaaatgg acagcctgag aacaactaca aaacaacccc ccctgtgctg   1200
gattctgatg gctctttctt tctgtactcc aaactgactg tggacaagtc tagatggcag   1260
caggggaatg tcttttcttg ctctgtcatg catgaggctc tgcataacca ctacactcag   1320
aaatccctgt ctctgtctcc tggcaaatga taa                                1353
```

<210> SEQ ID NO 108
<211> LENGTH: 1932
<212> TYPE: DNA
<213> ORGANISM: Artificial Sequence
<220> FEATURE:
<223> OTHER INFORMATION: Description of Artificial Sequence: Synthetic
      DNA sequence coding for multispecific polypeptide
      of SEQ ID NO: 105

<400> SEQUENCE: 108

```
caggtgcagc tgaagcagtc tggccctgga ctggtgcagc cttcccagtc cctgtccatc     60
acctgtaccg tgtccggctt ctccctgacc aactacggcg tgcactgggt gcgacagtct    120
ccaggcaagg gcctggaatg gctgggagtg atttggagcg gcggcaacac cgactacaac    180 accccctttca cctcccggct gagcatcaac aaggacaact ccaagtccca ggtgttcttc    240
aagatgaact ccctgcagtc caacgacacc gccatctact actgcgccag agccctgacc    300
tactatgact acgagttcgc ctactggggc cagggcaccc tcgtgacagt gtctgctgct    360
agcacaaagg gcctagtgt gtttcctctg gctccctctt ccaaatccac ttctggtggc    420
actgctgctc tgggatgcct ggtgaaggat tactttcctg aacctgtgac tgtctcatgg    480
aactctggtg ctctgacttc tggtgtccac actttccctg ctgtgctgca gtctagtgga   540
ctgtactctc tgtcatctgt ggtcactgtg ccctcttcat ctctgggaac ccagacctac   600
atttgtaatg tgaaccacaa accatccaac actaaagtgg acaaaaaagt ggaacccaaa   660
tcctgtgaca aaaccacac ctgcccacct tgtcctgccc ctgaactgct gggaggacct    720
tctgtgtttc tgttcccacc aaaaccaaaa gatacccctga tgatctctag aacccctgag  780
gtgacatgtg tggtggtgga tgtgtctcat gaggaccctg aggtcaaatt caactggtac   840
gtggatggag tggaagtcca caatgccaaa accaagccta gagaggaaca gtacaattca   900
acctacagag tggtcagtgt gctgactgtg ctgcatcagg attggctgaa tggcaaggaa   960
tacaagtgta aagtctcaaa caaggccctg cctgctccaa ttgagaaaac aatctcaaag  1020
gccaagggac agcctaggga accccaggtc tacaccctgc caccttcaag agaggaaatg  1080
```

```
accaaaaacc aggtgtccct gacatgcctg gtcaaaggct tctacccttc tgacattgct    1140
gtggagtggg agtcaaatgg acagcctgag aacaactaca aaacaacccc ccctgtgctg    1200
gattctgatg gctctttctt tctgtactcc aaactgactg tggacaagtc tagatggcag    1260
caggggaatg tcttttcttg ctctgtcatg catgaggctc tgcataacca ctacactcag    1320
aaatccctgt ctctgtctcc tggcaaaggc ggcggaggat ccggggggtgg gggaagcggc    1380 ggaggaggta gccaggactc caccagtgac cttatcccgg ctccccccct gtcaaaagta    1440
ccactacagc aaaatttcca ggacaaccag tttcagggca aatggtacgt tgttggactg    1500
gcagggaaca gaattctgcg ccaggaccag catcctatgc tcatgtatgc taccattttat    1560 gaactcaagg aggacaaatc ctaccaagtg acctctgtga ttagtagcca taagaagtgc    1620
ctctatccaa tcgccacatt cgtgcccggt tctcagcccg gcgaatttac actcgggaac    1680
atcaagtctt atggagacaa agtcagttat ttggttcgag tggtatctac aaattacaat    1740
cagcacgcaa tggtcttctt caaacatgcg gatacaaatt atgaaagttt ctccatcacc    1800 ctctacgaa ggaccaaaga gcttaccagc gagctgaagg aaaactttat acgattttcc    1860
aaatccttag gcctccctga aaatcacatc gtgtttcccg ttccgattga tcagtgtatc    1920
gacgggtgat aa                                                        1932

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 109

His His His His His His
1               5
```

MULTI-SPECIFIC POLYPEPTIDE USEFUL FOR LOCALIZED TUMOR IMMUNOMODULATION

SEQUENCE LISTING

The instant application contains a Sequence Listing which has been submitted electronically in ASCII format and is hereby incorporated by reference in its entirety. Said ASCII copy, created on Oct. 23, 2017, is named 029029-0167-SL-V2.txt and is 203 KB in size.

I. FIELD OF THE INVENTION

The present application provides a multi-specific polypeptide with a first moiety specific for a tumor-associated antigen on tumor cell surface and a second moiety specific for an immune checkpoint protein, which multi-specific polypeptide can be useful for biasing a T-cell-mediated response to a tumor micro-environment. For example, the polypeptide may contain: (a) a first binding domain, for example, a full-length antibody or an antigen-binding domain of an antibody, specifically recognizing a tumor-associated antigen on tumor cell surface, and (b) a second binding domain, such as a lipocalin mutein, capable of stimulating T-cell proliferation e.g., by inhibiting a protein receptor that down-regulates the immune system. The first binding domain may be genetically linked (i.e., peptide bond at its N- or C-terminus) to the second binding domain. The multispecific polypeptide also may contain a third or yet additional specific binding moieties, any of which can specifically bind a distinct immune checkpoint protein. The polypeptide may contain an Fc region of an antibody or of an antigen-binding domain thereof and simultaneously engage (1) a T cell receptor complex of a T cell, (2) a tumor-associated antigen on tumor cell surface, while (3) preserving the Fc function of the Fc region to Fc receptor-positive cell. The polypeptide is useful for the induction of an anti-tumor immunity in humans and/or animals. The present application further relates to a process for the production of the polypeptide as well as nucleic acids encoding for the polypeptide, to vectors comprising the same and to host cells comprising the vector. In another aspect, the present application provides for a pharmaceutical composition comprising the polypeptide and medical uses of the polypeptide. The present application also provides thermal-stable lipocalin muteins specific for CTLA-4.

II. BACKGROUND

As tumor-associated antigens exist on tumor cells, in principle, the immune system can recognize these antigens and attack the malignant cells. Tumors have, however, developed certain strategies enabling them to escape the immune reaction, for example, by insufficient presentation of tumor-associated antigens and/or insufficient activation of the tumor-specific T cells which are generally present.

One of the most effective mechanisms for tumor rejection is mediated by tumor-specific T lymphocytes. Regulation and activation of T lymphocytes depend on signaling by the T cell receptor (TCR) and also by co-signaling receptors that deliver negative or positive signals. The amplitude and quality of the immune response of T cells is controlled by equilibrium between co-stimulatory and inhibitory signals, called immune checkpoints.

Therefore, it would be highly advantageous for a multi-specific polypeptide, simultaneously locating tumor-associated antigens and modulating immune checkpoints, to induce tumor-immune infiltration.

III. DEFINITION

The following list defines terms, phrases, and abbreviations used throughout the instant specification. All terms listed and defined herein are intended to encompass all grammatical forms.

As used herein, "detectable affinity" means the ability to bind to a selected target (e.g. a tumor-associated antigen or an immune checkpoint protein) with an affinity constant of generally at least about $10^{-5}$ M or below. Lower affinities are generally no longer measurable with common methods such as ELISA and therefore of secondary importance.

As used herein, "binding affinity" of a molecule of the disclosure (e.g. a lipocalin mutein, an immunoglobulin or a multi-specific polypeptide) to a selected target (e.g. a tumor-associated antigen or an immune checkpoint protein), can be measured (and thereby $K_D$ values of a molecule-target complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective molecule and its target is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any one of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference in its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Identity is measured by dividing the number of identical residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the pro-peptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin mutein different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "fragment" as used herein in connection with the lipocalin muteins of the disclosure relates to proteins or peptides derived from full-length mature lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin.

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among various lipocalins.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

A "binding domain" of a multi-specific polypeptide disclosed herein is defined as a stretch of amino acids of the polypeptide, which stretch defines a unique functional unit of said polypeptide.

IV. DESCRIPTIONS OF FIGURES

FIG. 1: Diagrammatic representation of exemplifying multi-specific polypeptides of the disclosure. In FIG. 1A, lipocalin muteins are recombinantly fused to the C-terminus of immunoglobulin's light chain via a peptide bond (for example, a Serine Glycine linker). In FIG. 1B, lipocalin muteins are recombinantly fused to the C-terminus of immunoglobulin's heavy chain via a peptide bond (for example, a Serine Glycine linker). In FIG. 1C, lipocalin muteins are recombinantly fused to both the C-terminus of immunoglobulin's Heavy Chain and the C-terminus of immunoglobulin's light chain via a peptide bond (for example, a Serine Glycine linker).

Figure 2:
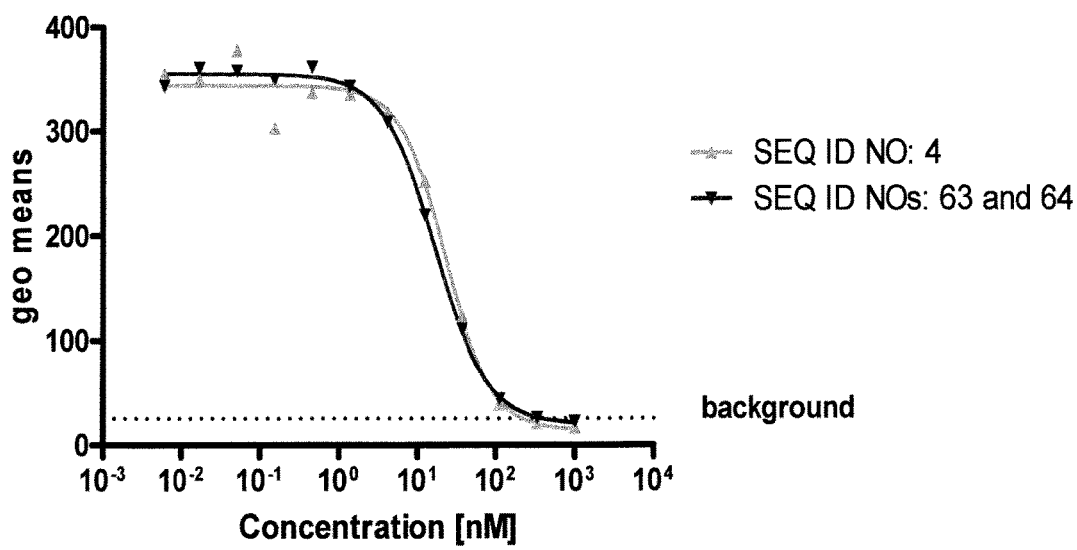

FIG. 2: a dose dependent inhibition of human B7.1 Fc-bio binding to human CTLA-4 transfected cells by a CTLA-4 specific lipocalin mutein (SEQ ID NO: 4) and a multi-specific polypeptide (comprising the amino acids shown in SEQ ID NOs: 63 and 64) that incorporates the lipocalin mutein and Reference Molecule 1 (comprising the amino acids shown in SEQ ID NOs: 63 and 98) can be observed. Both the lipocalin mutein and Reference Molecule 1 showed comparable inhibitory effect on B7.1 CTLA-4 binding at equal concentrations (FIG. 2). IC50 values were calculated using a sigmoidal dose response model with the program Prism (GraphPad). Similar IC50 values were obtained with the lipocalin mutein and the multi-specific polypeptide in this assay (23 nM and 16 nM, respectively). Wild type lipocalin 2 (SEQ ID NO: 1) did not lead to measurable inhibition of B7.1 binding to the CTLA-4 expressing CHO cells (data not shown).

Figure 3:
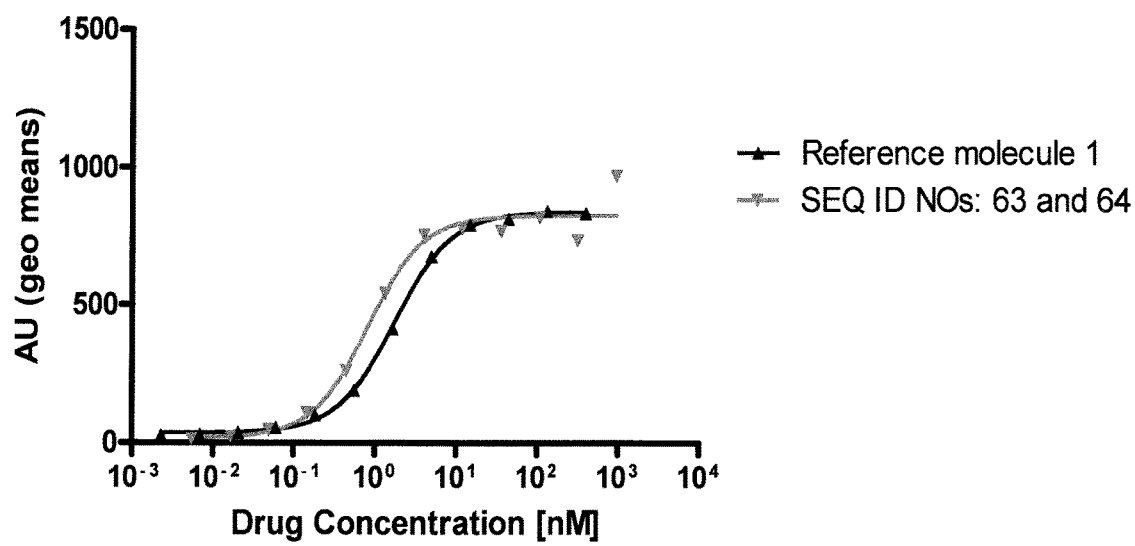
Figure 3B:
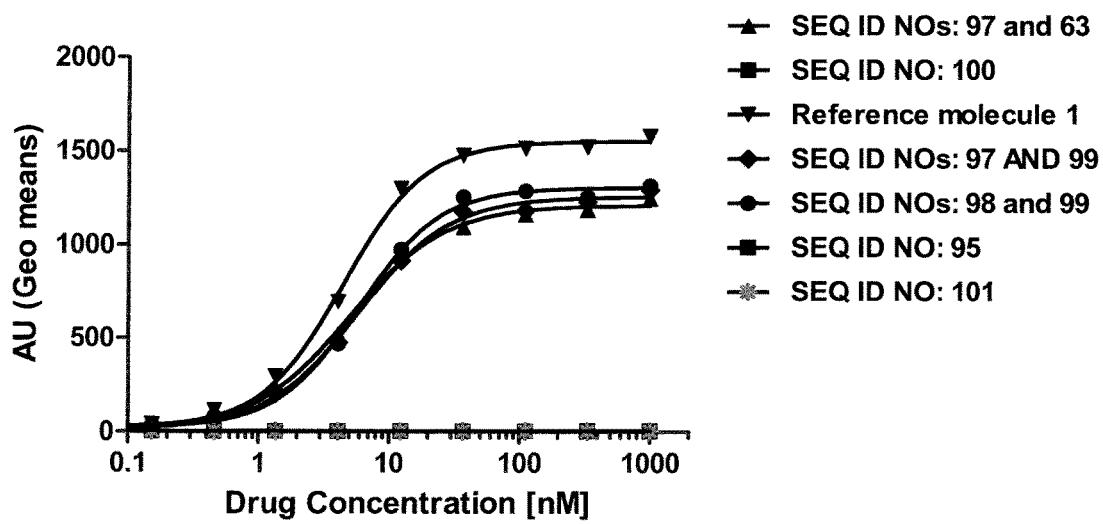
Figure 3C:
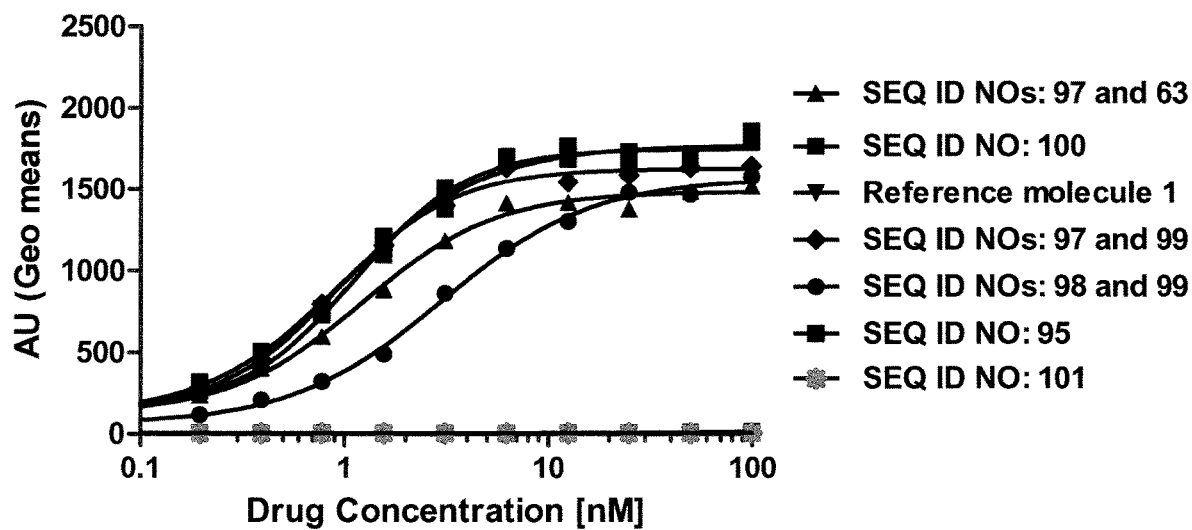

FIG. 3: FIG. 3A depicts a dose dependent binding of both Reference Molecule 1 and the multi-specific polypeptide (which incorporates Reference Molecule 1) to Her2 expressing T47D cancer cells can be observed. Both molecules bind to Her2 expressing T47D cells with similar affinities (FIG. 3A). IC50 values were calculated using a sigmoidal dose response model with the program Prism (GraphPad). Similar EC50 values were obtained with Reference Molecule 1 and the multi-specific polypeptide in this assay (1.7 nM and 0.8 nM, respectively). FIG. 3B and FIG. 3C depict a dose dependent binding of multi-specific polypeptides to SKBR3 and CTLA4 transfected Jurkat cells, respectively. Reference Molecule 1 was used as a positive control in the SKBR3 binding assay while polypeptide of SEQ ID NO: 100 and lipocalin mutein of SEQ ID NO: 95 were used in the CLTA4 Jurkat cell binding assay. 1050 values were calculated as described above and were similar to positive controls. Isotype control antibodies did not lead to measurable binding to the T47D cells, SKBR3 or CTLA-4 Jurkat cells (data not shown).

Figure 4:
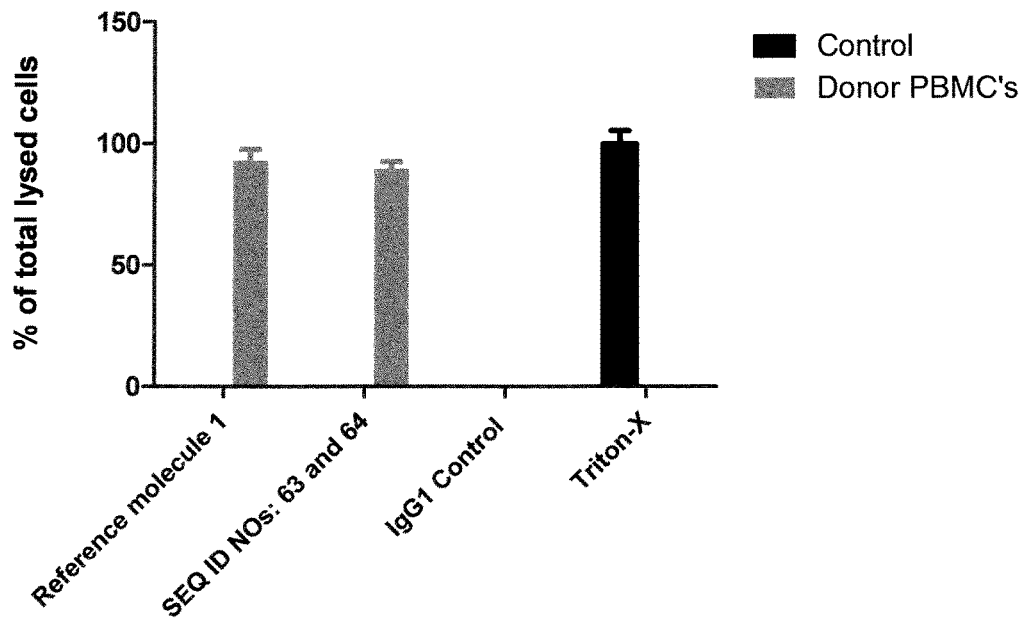
Figure 4:
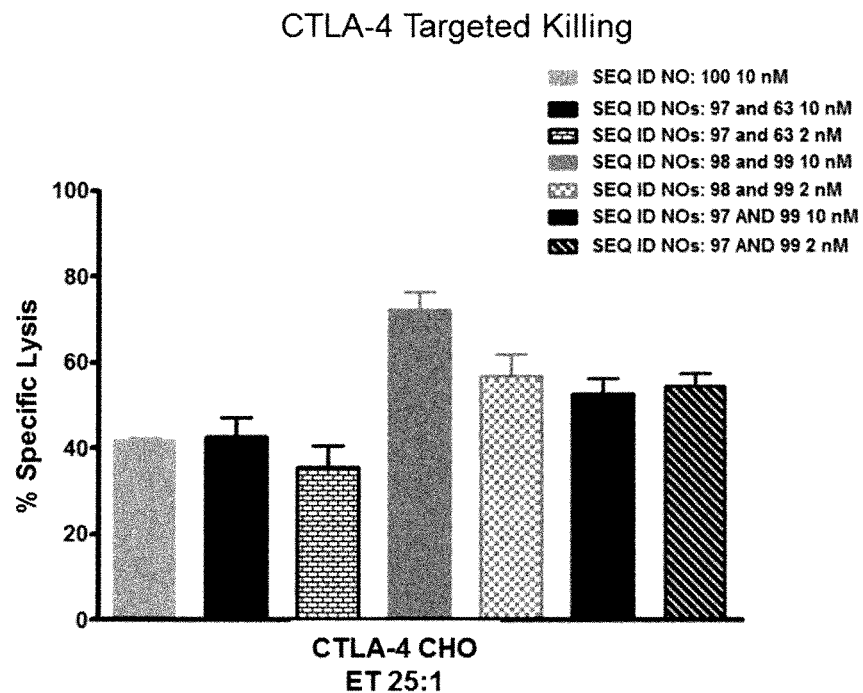

FIG. 4: ADCC assay demonstrating lysis of Her2 expressing SKBR3 cancer cells (FIG. 4A) and CTLA-4 expressing chinese hamster ovary (CHO) cells (FIG. 4 B) by Reference Molecule 1 and multi-specific polypeptides in the presence of donor Peripheral Blood Mononuclear cell (PBMC). Similar SKBR3 specific lysis values were obtained with Reference Molecule 1 and the multi-specific polypeptides in this assay (approximately 55% and 90%, respectively; FIG. 4A). Similar CHO: CTLA-4 specific lysis values were obtained with the multi-specific polypeptides in this assay (approximately 55%; FIG. 4B). Isotype control antibodies did not lead to measurable lysis of cells.

Figure 5:
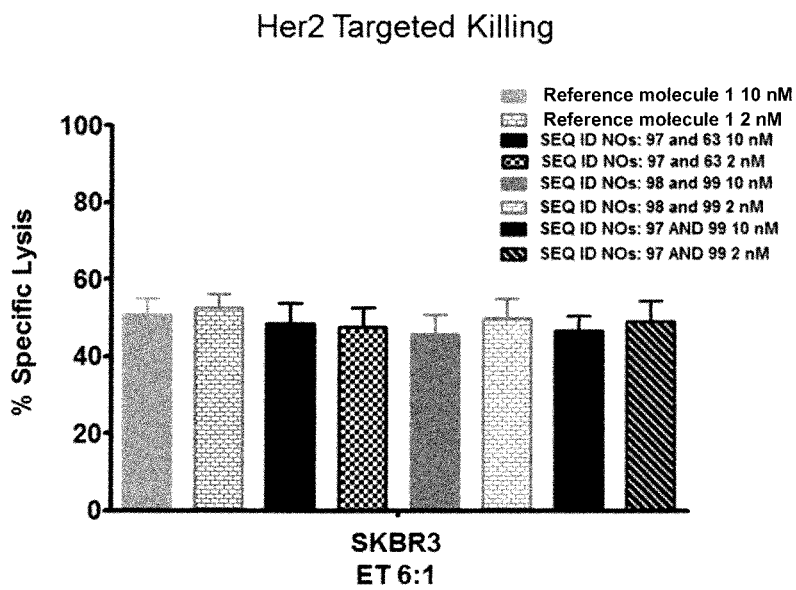
Figure 5:
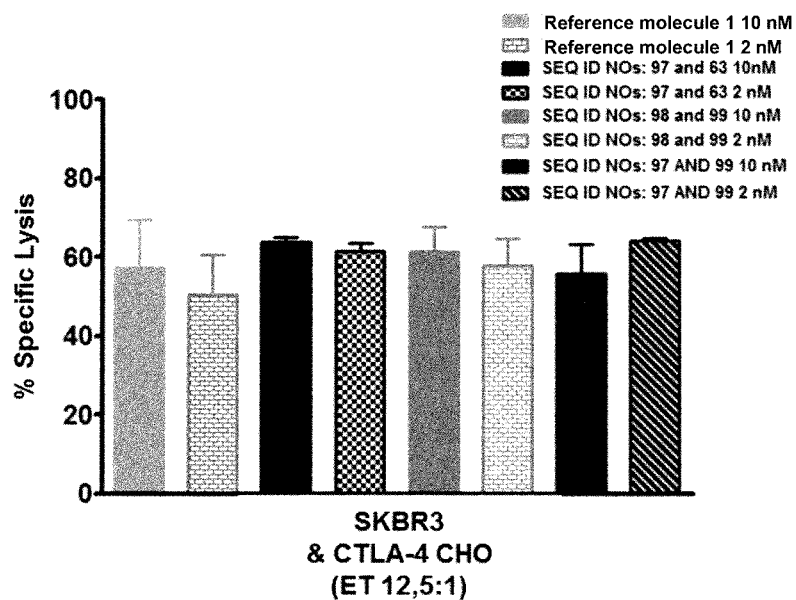
Figure 5:
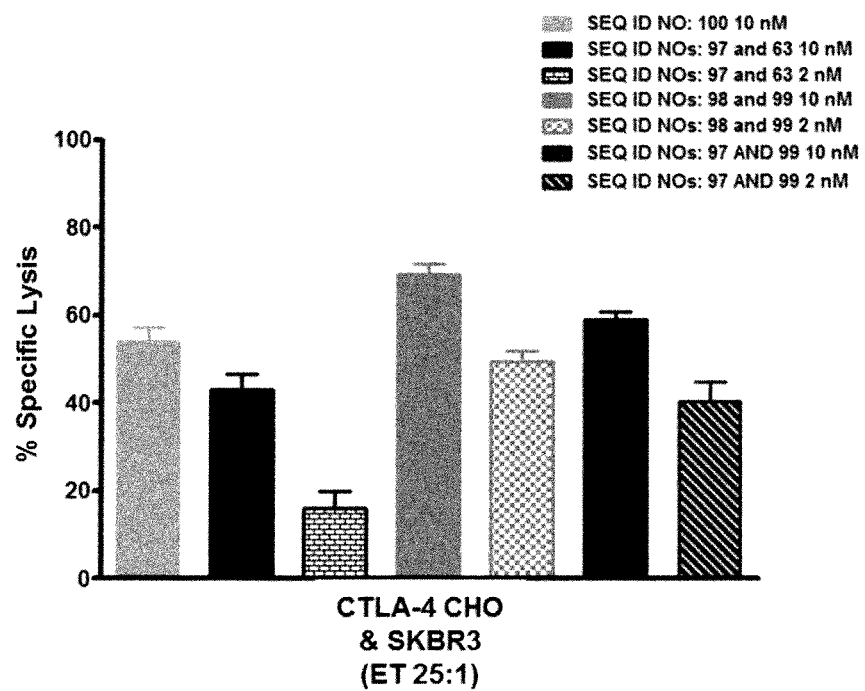

FIG. 5: Bidirectional killing (ADCC) of multi-specific polypeptides in co-culture model. Target dependent killing of SKBR3 was observed for both Reference Molecule 1 and the multi-specific polypeptides in absence (FIG. 5A) or in presence of CHO: CTLA-4 cells (FIG. 5B). Presence of CHO: CTLA-4 cells had no impact on specific lysis. Target dependent killing of CHO: CTLA-4 in presence of SKBR3 cells was observed for the multi-specific polypeptides (FIG. 5C). Presence of Her 2 expressing cells SKBR3 has only a minor impact on specific lysis.

Figure 6:
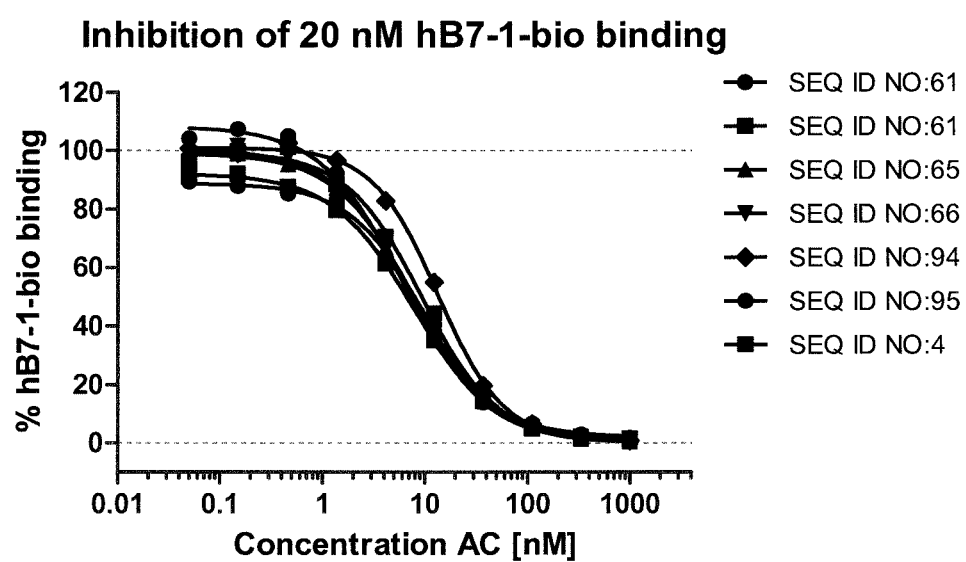

FIG. 6: depicts the results of a cell-based competition assay of lipocalin muteins blocking human B7.1 binding to a human CTLA4-transfected CHO cell line. 1050 values were calculated using a sigmoidal dose response model with the program Prism (GraphPad).

Figure 7:
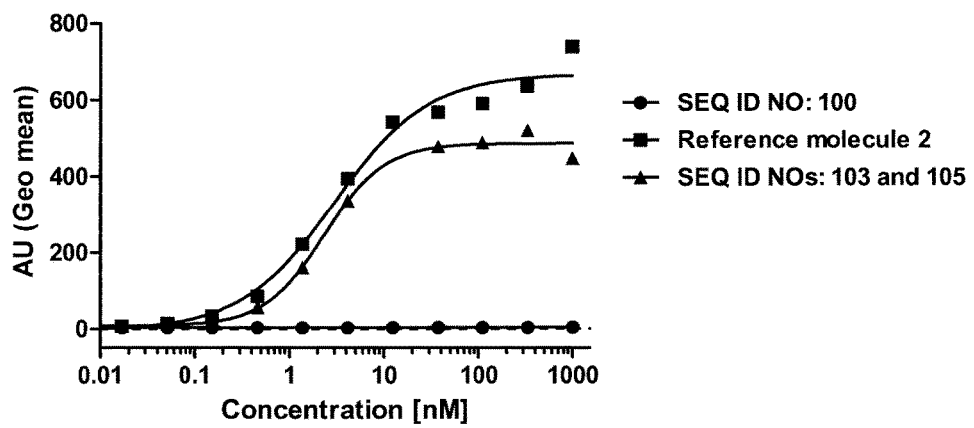
Figure 7:
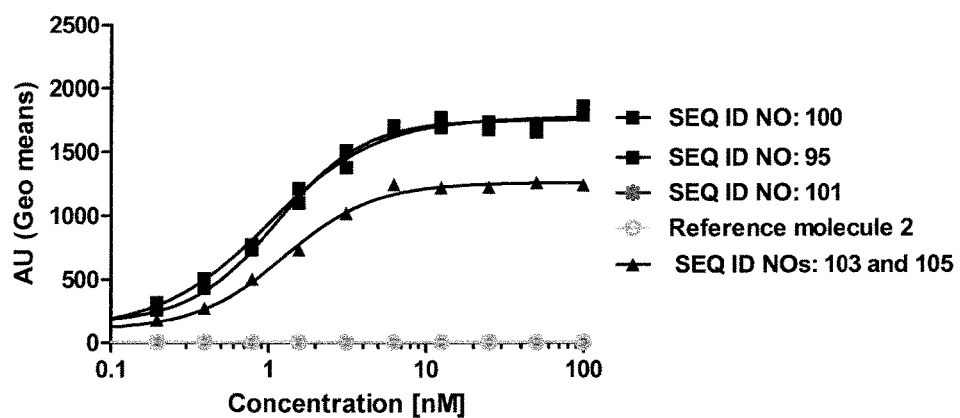

FIG. 7: FIG. 7A and FIG. 7B depict a dose dependent binding of multi-specific polypeptides to A431 cells and CTLA-4 transfected Jurkat cells, respectively. Reference Molecule 2 was used as positive control in the A431 binding assay while polypeptide of SEQ ID NO: 100 and lipocalin mutein of SEQ ID NO: 95 were used as positive control in the CLTA-4 positive Jurkat cell binding assay. EC50 values were calculated as described above and were similar to positive controls. Isotype control antibodies did not lead to measurable binding to the A431 cells or CTLA-4 positive Jurkat cells (data not shown).

Figure 8:
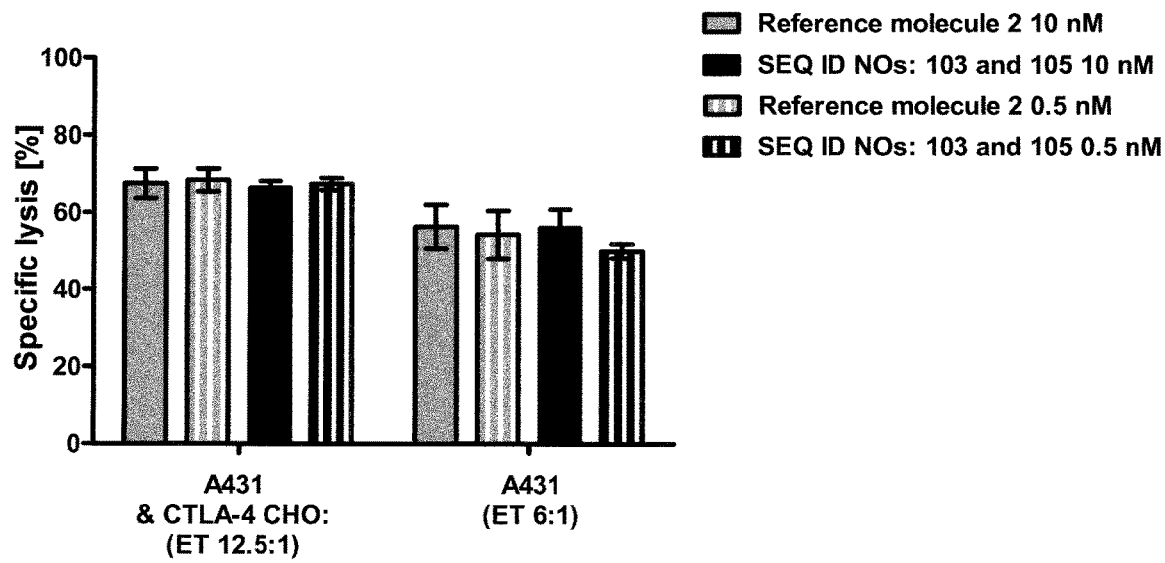
Figure 8:
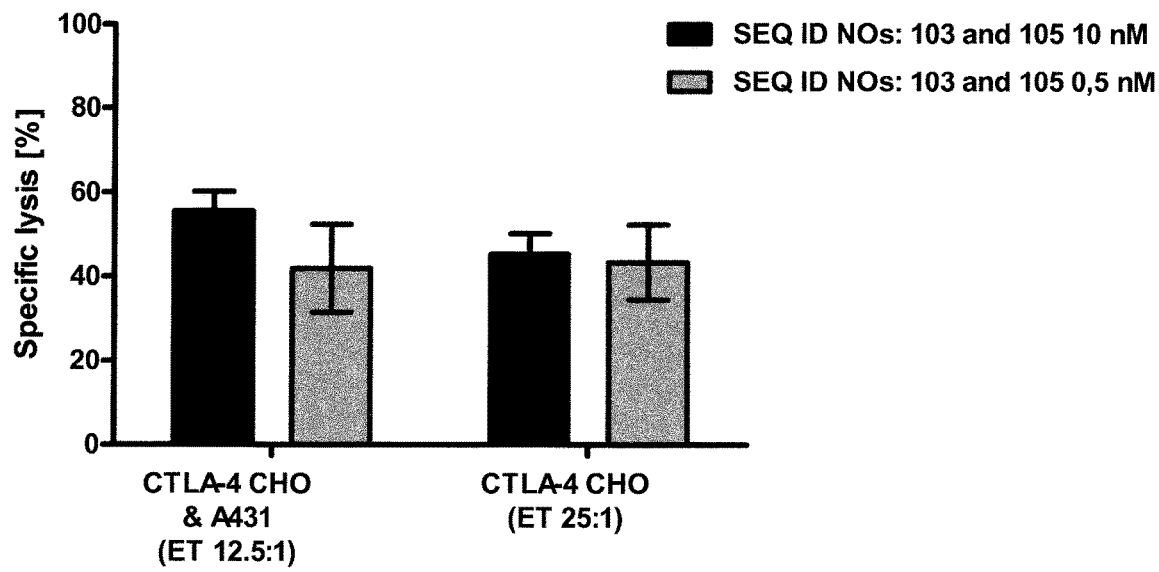

FIG. 8: Bidirectional killing (ADCC) of multi-specific polypeptides in co-culture model. FIG. 8A: Target dependent killing of A431 was observed for both Reference Molecule 2 and the multi-specific polypeptides in absence or in presence of CHO: CTLA-4 cells. Presence of CHO: CTLA-4 cells had no impact on specific lysis. FIG. 8B: Target dependent killing of CHO: CTLA-4 in absence or in presence of A431 cells was observed for the multi-specific polypeptide. Presence of EGFR expressing cells A431 had no impact on specific lysis.

V. DETAILED DESCRIPTION OF THE DISCLOSURE

Immune checkpoints generally refer to a plethora of pathways hardwired into the immune system that are crucial for maintaining self-tolerance and modulating the duration and amplitude of physiological immune responses in peripheral tissues in order to minimize collateral tissue damage, and many of the immune checkpoints are initiated by ligand-receptor interactions.

Tumors co-opt certain immune-checkpoint pathways as a major mechanism of immune resistance, particularly against T cells that are specific for tumor antigens. The ability to evade the immune system has been added to the list of hallmark capabilities acquired by normal cells that drives their transformation into a malignant state.

Anti-tumor immunity is often ineffective due to the tight regulation associated with the maintenance of immune homeostasis. One of the major limitations is a process known as 'T-cell exhaustion', which results from chronic exposure to antigens and is characterized by the up-regulation of inhibitory receptors. These inhibitory receptors serve as inhibitory immune checkpoints in order to prevent uncontrolled immune reactions. These checkpoint proteins help to keep the immune system in check and bring an immune reaction to an end at the appropriate time.

One of the ways in which cancer cells are able to evade the immune system is by hijacking some inhibitory checkpoint proteins; overexpression of these proteins on tumor cells enables a tumor to dampen down the immune response against it. Therefore, manipulations of the inhibitory immune checkpoints may provide therapeutic strategies for autoimmune diseases, tumor growth, infectious diseases and transplantation by enhancing T cell activity.

One of the inhibitory receptors is cytotoxic T-lymphocyte antigen 4 (CTLA-4), also known as CD152. CTLA-4 shares sequence homology and ligands (CD80/B7-1 or CD86/B7-2) with the co-stimulatory molecule CD28, but differs by delivering inhibitory signals to the T cells on which it is expressed as a receptor. Activation of cellular immunity begins when T cells recognize peptide fragments of intracellular proteins that are expressed on the surface of antigen-presenting cells (APCs) bound to specific mixed histocompatibility complex (MHC) molecules. This interaction requires the presence of a co-stimulatory molecule—B7 and this activation results in up-regulation of CTLA-4. The CTLA-4 receptor on T lymphocytes, as a negative regulator of T cell activation, out-competes CD28 for binding to B7 on antigen-presenting cells. CTLA-4 thereby serves as a physiologic "brake" on the activated immune system.

PD-1 is another inhibitory receptor expressed on activated and exhausted T cells, while its ligand, PD-L1, is often found overexpressed in various types of cancer (Gao et al. 2009; Gadiot et al. 2011). PD-1 is with two ligands, PD-L1 (also known as B7-H1; CD274) and PD-L2 (B7-DC; CD273). Blocking interactions between PD-1 and its ligands, PD-L1 and PD-L2, enhances adaptive anti-tumor immune responses by preventing T-cell exhaustion [Hirano et al. 2005]. PD-1 is expressed by activated CD4+ and CD8+ T cells, B cells, monocytes and natural killer T cells [Gao et al. 2009; Gadiot et al. 2011].

Lymphocyte-activation gene 3 (LAG-3) is another recently identified inhibitory receptor that acts to limit effector T-cell function and augment the suppressive activity of T regulatory cells [Woo et al. 2012]. LAG-3 is a CD4-like negative regulatory protein with a high affinity binding to MHC Class II that leads to tolerance of T cell proliferation and homeostasis. Blockade of the LAG-3/Class II interaction enhances anti-tumor immune responses.

In addition, blockade of other inhibitory receptors, such as BTLA (B- and T-lymphocyte attenuator), KIRs (killer immunoglobulin-like receptors), TIM-3 (T cell immunoglobulin and mucin domain-containing protein 3), A2aR (adenosine 2A receptor), B7-H3 or H4 (B7 family members), may also enhance anti-tumor immunity.

Killer inhibitory receptors (KIRs) are a broad category of inhibitory receptors that can be divided into two classes based on structure: killer cell immunoglobulin-like receptors and C-type lectin receptors, which are type II transmembrane receptors (Lanier, L. L. Up on the tightrope: natural killer cell activation and inhibition. *Nature Immunol.* 9, 495-502 (2008)). These receptors were originally described as crucial regulators of the killing activity of Natural Killer (NK) cells, although many are expressed on T cells and antigen-presenting cells (APCs) (Mingari, M. C., Pietra, G. & Moretta, L. Human cytolytic T lymphocytes expressing HLA class-I-specific inhibitory receptors. *Curr. Opin. Immunol.* 17, 312-319 (2005)). Activation of NK cells can provide potent anti-tumor activity. Many of the killer inhibitory receptors are specific for subsets of human leukocyte antigens (HLAs; the human MHC molecules) and possess allele-specificity. However, other killer inhibitory receptors recognize broadly expressed molecules; for example, the C-type lectin receptor KLRG1 recognizes E-cadherin.

TIM-3 has been identified as another important inhibitory receptor expressed by exhausted CD8+ T cells [Sakuishi et al. 2010]. TIM-3 has also been reported as a key regulator of nucleic acid mediated anti-tumor immunity. TIM-3 was shown to be up-regulated on tumor-associated dendritic cells (TADCs) extracted from both mouse and human tumors [Chiba et al. 2012]. It was demonstrated that TIM-3 expression on TADCs (and not on CD8 T cells) was the main limit to the triggering of a nucleic acid mediated antitumor immune response.

BTLA was first identified as an inhibitory receptor on T cells on the basis of the enhanced T cell responses that were observed in Btla-knockout mice (Watanabe, N. et al. BTLA is a lymphocyte inhibitory receptor with similarities to CTLA-4 and PD-1. *Nature Immunol.* 4, 670-679 (2003)). Thus, BTLA may also be a relevant inhibitory receptor for T cells in the tumor microenvironment (Lasaro, M. O. et al. Active immunotherapy combined with blockade of a co-inhibitory pathway achieves regression of large tumor masses in cancer-prone mice. *Mol. Ther.* 19, 1727-1736 (2011).

A2aR, the ligand of which is adenosine, inhibits T cell responses, in part by driving CD4+ T cells to express FOXP3 and hence to develop into TReg cells (Zarek, P. E. et al. A2A receptor signaling promotes peripheral tolerance by inducing T-cell anergy and the generation of adaptive regulatory T cells. *Blood* 111, 251-259 (2008)). Deletion of this receptor results in enhanced and sometimes pathological inflammatory responses to infection (Waickman, A. T. et al.

Enhancement of tumor immunotherapy by deletion of the A(2A) adenosine receptor. *Cancer Immunol. Immunother.* 25 Nov. 2011). This receptor is particularly relevant to tumor immunity because the rate of cell death in tumors from cell turnover is high, and dying cells release adenosine. In addition, A2aR engagement by adenosine drives T cells to become TReg cells, this can produce a self-amplifying loop within the tumor (Deaglio, S. et al. Adenosine generation catalyzed by CD39 and CD73 expressed on regulatory T cells mediates immune suppression. *J. Exp. Med.* 204, 1257-1265 (2007)).

Immunological studies have demonstrated that various immune-checkpoint receptors are expressed coordinately under circumstances of tolerance to self-antigens and chronic infections, as well as in inflammatory settings. In addition to defined lymphocyte inhibitory receptors, numerous B7 family inhibitory ligands—in particular B7-H3 (also known as CD276) and B7-H4 (also known as B7-S1, B7x and VCTN1)—do not yet have defined receptors, but mouse knockout experiments support an immune inhibitory role for these ligands (Yi, K. H. & Chen, L. Fine tuning the immune response through B7-H3 and B7-H4. *Immunol. Rev.* 229, 145-151 (2009)). For example, B7-H3 and B7-H4 are up-regulated on tumor cells or tumor-infiltrating cells (He, C., Qiao, H., Jiang, H. & Sun, X. The inhibitory role of B7-H4 in antitumor immunity: association with cancer progression and survival. *Clin. Dev. Immunol.* 2011, 695834 (2011)).

More recently, Indoleamine (2,3)-dioxygenase (IDO) was also identified as a checkpoint protein involved in generating the immunosuppressive tumor microenvironment that supports tumor growth (Ino K, Tanizaki Y, Kobayashi A, et al. Role of the immune tolerance-inducing molecule indoleamine 2,3-dioxygenase in gynecologic cancers. J Cancer Sci Ther. 2012; S13). IDO is an enzyme with two isoforms (IDO1 and IDO2) that acts at the first step in the metabolic pathway that breaks down the essential amino acid tryptophan. IDO exerts its immunomodulatory effects by shutting down the effector T cells of the immune system (Smith C, Chang M Y, Parker K H, et al. IDO is a nodal pathogenic driver of lung cancer and metastasis development. Cancer Discov. 2012; 2(8):772-735). IDO expression also directly activates the regulatory T cells, a subset of T cells whose major function is to shut down T cell-mediated immunity at the end of an immune reaction.

On the other hand, co-stimulatory checkpoint proteins delivering positive signals such as ICOS (inducible T cell co-stimulator), CD28 or the TNF family members (such as 4-1 BB (CD137), OX40, CD27 or CD40), have been shown to be involved in allergy, autoimmune or inflammatory diseases, since one mechanism for tumor cells to evade the immune system is the absence of co-stimulatory molecules (Lundberg, A., et al., 1993). For activation and clonal expansion, T cells require co-stimulatory signals in addition to the primary signal provided by the T-cell receptor (TCR) which interacts with pep tide-bearing major histocompatibility complex (MHC) molecules (Rudd, C. E., et al., 1994). TCR stimulation in the absence of co-stimulation can result in unresponsiveness and the induction of clonal anergy (Harding, F. A., et al., 1992; Gimmi, C D., et al., 1993; Tan, P. C., et al., 1993).

Meanwhile, in cancer therapy, it is a general aim to treat the afflicted tissues as efficiently and selectively as possible. Tumors can express a high level of certain types of tumor-associated antigens. Tumor-associated antigen is an antigenic substance produced in tumor cells and can be useful in identifying tumor cells. To selectively treat hyper-proliferative diseases such as cancer and ensure a localized immune reaction in the afflicted tissue, inventors of the current disclosure endeavors to develop polypeptides not only capable of modulating the immune checkpoints but also having binding specificity for tumor-associated antigens. Tumor-associated antigens that may be targeted include, but are not limited to, CD20, CD30, CD33, CD38, CD52, VEGF, VEGF receptors (such as VEGFR-1 (Flt-1) and VEGFR-2 (KDR/Flk-1)), EGFR or Her2/neu (Mizukami et al., 2005, Nature Med. 11:992-97; Hatfield et al., 2005, Curr. Cancer Drug Targets 5:229-48; Vallbohmer et al. 2005, J. Clin. Oncol. 23:3536-44; and Ren et al. 2005, Ann. Surg. 242:55-63).

Thus, the current disclosure puts forward a multi-specific polypeptide having the following properties:
(a) binding specificity for an immune checkpoint protein; and
(b) binding specificity for a tumor-associated antigen.

In some embodiments, the multi-specific polypeptide contains at least two binding domains: a first binding domain that comprises a full-length immunoglobulin or an antigen-binding domain thereof specific for a tumor-associated antigen, and a second binding domain that comprises a lipocalin mutein specific for an immune checkpoint protein.

In some embodiments, the multi-specific polypeptide of the disclosure includes bi-specific polypeptide with a first binding domain specific for a tumor-associated antigen, and a second binding domain specific for an immune checkpoint protein.

In some embodiments, the polypeptide also may contain a third or yet additional specific binding moieties. For instance, the multi-specific polypeptide may contain a third binding domain specific for an immune checkpoint protein, which immune checkpoint protein may be the same as or different from the immune checkpoint protein targeted by the second binding domain referred above. In some embodiments, said third binding domain comprises a lipocalin mutein specific for an immune checkpoint protein.

By blocking of one or several of inhibitory immune checkpoints of the disclosure, the multi-specific polypeptide rescues otherwise exhausted anti-tumor T cells, enhances anti-tumor immunity and, thereby, enlists positive responses in cancer patients. In some further embodiments, dual blockade of coordinately expressed immune-checkpoint proteins can produce additive or synergistic anti-tumor activities.

In some embodiments, one binding domain can be linked to one or more other binding domains as essentially described in FIG. 1. For example, one or more lipocalin muteins can be linked, via a peptide bond, to the C-terminus of the immunoglobulin heavy chain domain (VH), the N-terminus of the VH, the C-terminus of the immunoglobulin light chain (VL), and/or the N-terminus of the VL (cf. FIG. 1). In some particular embodiments, a lipocalin mutein binding domain can be fused at its N-terminus and/or its C-terminus to an immunoglobulin binding domain. For example, the lipocalin mutein may be linked via a peptide bond between (i) the N-terminus of the lipocalin and (ii) the C-terminus of a heavy chain constant region (CH) or the C-terminus of a light chain constant region (CL) of the immunoglobulin. In some still further embodiments, the peptide bond may be a Serine Glycine linker, for example, as shown in SEQ ID NO: 87.

In this regard, one binding domain may be fused at its N-terminus and/or its C-terminus to another binding domain. For example, when the first binding domain comprises a full-length immunoglobulin, the second binding domain may be linked via a peptide bond between the N-terminus of the second binding domain and the C-terminus of a heavy chain constant region (CH) of said immunoglobulin. In some further embodiments, the third binding domain may be linked via a peptide bond between the N-terminus of the third binding domain and the C-terminus of a light chain constant region (CL) of the immunoglobulin of the first binding domain. In some still further embodiments, the peptide bond may be a Serine Glycine linker, for example, as shown in SEQ ID NO: 87.

In some embodiments with respect to a multi-specific polypeptide of the disclosure whose first binding domain comprises a full-length immunoglobulin, while the multi-specific polypeptide is simultaneously engaging an immune checkpoint protein and a tumor-associated antigen, the Fc function of the Fc region of the full-length immunoglobulin to Fc receptor-positive cell may be preserved at the same time.

In some embodiments, the multi-specific polypeptide is capable of binding, via its Fc portion, to the Fc receptor of Fc receptor-positive cells. In some further embodiments, the multi-specific polypeptide may activate the Fc receptor-positive cell by binding to the Fc receptor-positive cell, thereby initiating or increasing the expression of cytokines and/or co-stimulatory antigens. Furthermore, the multi-specific polypeptide may transfer at least a second activation signal required for physiological activation of the T cell to the T cell via the co-stimulatory antigens and/or cytokines.

In some embodiments, resulted from the binding of its Fc portion to other cells that express Fc receptors present on the surface of effector cells from the immune system, such as immune cells, hepatocytes, and endothelial cells, the multi-specific polypeptide of the disclosure may possess antibody-dependent cellular cytotoxicity (ADCC) function, a mechanism of cell-mediated immune defense whereby an effector cell of the immune system actively lyses a target cell, whose membrane-surface antigen has been bound by an antibody, and therefore, trigger tumor cell death via ADCC. In some further embodiments, the multi-specific polypeptide is capable of demonstrating ADCC function, for example, when measured in an assay essentially described in Example 3. In some still further embodiments, the multi-specific polypeptide is capable of demonstrating comparable level of ADCC function as the immunoglobulin included in such multi-specific polypeptide, such as Reference Molecule 1, for example, when measured in a SKBR3-cell based assay essentially described in Example 3. In some additional embodiments, the multi-specific polypeptide is capable of demonstrating comparable or superior level of ADCC function as a fusion molecule of the lipocalin mutein included in such multi-specific polypeptide with the Fc region of an antibody (e.g. IgG1), such as the polypeptide of SEQ ID NO: 100, for example, when measured in an assay based on chines hamster ovary (CHO): CTLA-4 cells essentially described in Example 3.

Apart from the Fc-mediated cytotoxicity, the Fc portion may contribute to maintaining the serum levels of the multi-specific polypeptide, critical for its stability and persistence in the body. For example, when the Fc portion binds to Fc receptors on endothelial cells and on phagocytes, the multi-specific polypeptide may become internalized and recycled back to the blood stream, enhancing its half-life within the body. In some further embodiments, the multi-specific polypeptide is capable of binding to Fc-gamma receptor hFcγ RI/CD64 with an affinity measured by a dissociation constant $K_D$ of about 1 nM or lower, such as about 150 pM, when measured in an assay essentially described in Example 6. In some further embodiments, the multi-specific polypeptide is capable of binding to Fc-gamma receptor hFcγ RIIIA/CD16a with an affinity measured by a dissociation constant $K_D$ of about 1 nM or lower, such as about 0.5 μM, when measured in an assay essentially described in Example 6. In some still further embodiments, the multi-specific polypeptide is capable of demonstrating comparable affinity to Fc-gamma receptors hFcγ RI/CD64 and/or hFcγ RIIIA/CD16a as the immunoglobulin included in the multi-specific polypeptide, such as Reference Molecule 1, for example, when measured in an assay essentially described in Example 6. In some still further embodiments, the multi-specific polypeptide is capable of demonstrating comparable affinity to Fc-gamma receptors hFcγ RI/CD64 and/or hFcγ RIIIA/CD16a as the immunoglobulin included in the multi-specific polypeptide, such as Reference Molecule 2, for example, when measured in an assay essentially described in Example 13.

In some embodiments, the multi-specific polypeptide may be able to activate the tumor-specific T cells recognizing a tumor-specific peptide presented on the tumor cells by MHC class I and/or class II via their T cell receptor. Furthermore, the multi-specific polypeptide may be able to reactivate the tumor-specific T cells being in an anergic state. In addition, the multi-specific polypeptide may be able to induce tumor-reactive complement-binding antibodies and, thus, induce a humoral immune reaction.

In some embodiments, with respect to the multi-specific polypeptide, the first binding domain comprises a full-length immunoglobulin or an antigen-binding domain thereof specific for an antigen selected from the group consisting of CD20, CD30, CD33, CD38, CD52, VEGF, VEGF receptors, EGFR or Her2/neu.

The immunoglobulin, for example, may be IgG1 or IgG2 (e.g. IgG2a). In further embodiments, the immunoglobulin is a monoclonal antibody against CD20, CD30, CD33, CD38, CD52, VEGF, VEGF receptors, EGFR or Her2/neu. A few illustrative examples for such immunoglobulins include an antibody comprised within any of the following: trastuzumab (trade names Herclon, Herceptin), panitumumab (trade name Vectibix), cetuximab (trade name Erbitux), obinutuzumab (trade name Gazyva), rituximab (trade name Rituxan), pertuzumab (also called 2C4, trade name Perjeta), alemtuzumab (trade name Campath), bevacizumab (trade name Avastin), tositumomab (combination of which sold under trade name Bexxar), ibritumomab (combination of which sold under the trade name Zevalin), ofatumumab (trade name Arzerra), brentuximab (conjugate of which sold under the trade name Adcetris) and gemtuzumab (conjugate of which sold under the trade name Mylotarg).

In some embodiments, the multi-specific polypeptide of disclosure may be capable of antagonizing one or more inhibitory immune checkpoint proteins, for example, CTLA-4, PD-1, PD-L1, PD-L2, LAG-3, A2aR, a killer immunoglobulin receptor (KIR) (such as alpha-KIR), TIM-3, BTLA, B7-H3, B7-H4 and IDO.

In some other embodiments, the multi-specific polypeptide of disclosure may be capable of agonizing one or more co-stimulatory checkpoint proteins, for example, ICOS (inducible T cell co-stimulator), CD28, the TNF family members (such as 4-1 BB (CD137), OX40, CD27 and CD40.

In some embodiments with respect to the multi-specific polypeptide, the second binding domain comprises a lipocalin mutein specific for an immune checkpoint protein selected from the group consisting of CTLA-4, PD-1, PD-L1, PD-L2, LAG-3, A2aR, a KIR, TIM-3, BTLA, B7-H3, B7-H4, IDO, ICOS (inducible T cell co-stimulator), CD28, the TNF family members (such as 4-1BB (CD137), OX40, CD27 and CD40.

Lipocalins are proteinaceous binding molecules that have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain, having a cylindrical β-pleated sheet supersecondary structural region comprising a plurality of eight β-strands connected pair-wise by a plurality of four loops at one end to define thereby a binding pocket. It is the diversity of the loop regions in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins has naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297, which is incorporated by reference in its entirety herein.

Lipocalins are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signalling, and the synthesis of prostaglandins. The lipocalins have also been implicated in the regulation of the immune response and the mediation of cell homoeostasis (reviewed, for example, in Flower, D. R. (1996) Biochem. J. 318, 1-14 and Flower, D. R. et al. (2000) Biochim. Biophys. Acta 1482, 9-24). The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) Biochim. Biophys. Acta 1482, 337-350).

A lipocalin is defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin muetein is effective to bind an immune checkpoint protein with detectable affinity.

A lipocalin mutein of the disclosure may derive from the group consisting of retinol-binding protein (RBP), bilin-binding protein (BBP), apolipoprotein D (APO D), neutrophil gelatinase associated lipocalin (NGAL), tear lipocalin (TLPC or Tlc), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1).

In some embodiments, the lipocalin mutein as contained in the multi-specific polypeptide has a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin mutein is effective to bind an immune checkpoint protein as given non-natural target with detectable affinity.

In one preferred embodiment, a lipocalin mutein disclosed herein is a mutein of Lipocalin 2 (Lcn 2; also known as human neutrophil gelatinase-associated lipocalin, hNGAL, or as siderocalin). The term "human neutrophil gelatinase-associated lipocalin" or "hNGAL" or "lipocalin 2" or "Lcn2" as used herein refers to the mature hNGAL with the SWISS-PROT/UniProt Data Bank Accession Number P80188 (Isoform 1). The amino acid sequence shown in SWISS-PROT/UniProt Data Bank Accession Number P80188 may be used as a preferred "reference sequence", the amino acid sequence shown in SEQ ID NO: 1 is an alternatively preferred reference sequence. It shows the amino acid sequence of SWISS-PROT/UniProt Data Bank Accession Number P80188 lacking the N-terminal signal sequence, i.e. amino acids 1-20 of the amino acid sequence of SWISS-PROT/UniProt Data Bank Accession Number P80188.

In yet another preferred embodiment, a lipocalin mutein disclosed herein is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence".

Various PCT publications (e.g., WO 99/16873, WO 00/75308, WO 03/029463, WO 03/029471 and WO 2005/19256), which are incorporated by reference in their entirety herein, disclose how muteins of various lipocalins (e.g. Lcn 2 or Tlc) can be constructed to exhibit a high affinity and specificity for a target that is different than a natural ligand of a wild type lipocalin. This can be done, for example, by mutating one or more amino acid positions of at least three of the four loops.

The amino acid sequence of a lipocalin mutein according to the disclosure has a high sequence identity to respective lipocalin when compared to sequence identities with another lipocalin (see also above). In this general context the amino acid sequence of a lipocalin mutein of the combination according to the disclosure is at least substantially similar to the amino acid sequence of the corresponding lipocalin (the wild-type or reference lipocalin). A respective sequence of a lipocalin mutein of the combination according to the disclosure, being substantially similar to the sequences of the corresponding lipocalin, has in some to the wild-type (or reference) lipocalin, one or more amino acid embodiments at least 65%, at least 70%, at least 75%, at least 80%, at least 82%, at least 85%, at least 87%, or at least 90% identity, including at least 95% identity to the sequence of the corresponding lipocalin. In this regard, a lipocalin mutein of the disclosure of course may contain, in comparison substitutions as described herein which renders the lipocalin mutein capable of binding to an immune checkpoint protein. Typically a mutein of a lipocalin includes one or more mutations—relative to the native sequence lipocalin—of amino acids in the four loops at the open end of the ligand binding site of the lipocalin (cf. above). As explained above, these regions are essential in determining the binding specificity of a lipocalin mutein for a desired target. As an illustrative example, a mutein derived from a polypeptide of tear lipocalin, lipocalin 2 or a homologue thereof, may have one, two, three, four or more mutated amino acid residues at any sequence position in the N-terminal region and/or in the three peptide loops BC, DE, and FG arranged at the end of the β-barrel structure that is located opposite to the natural lipocalin binding pocket. As a further illustrative example, a mutein derived from a polypeptide of tear lipocalin or a homologue thereof, may have no mutated amino acid residues in peptide loop DE arranged at the end of the β-barrel structure, compared to wild type sequence of tear lipocalin.

A lipocalin mutein according to the disclosure includes one or more, such as two, three, four, five, six, seven, eight, nine, ten, eleven, twelve, thirteen, fourteen, fifteen, sixteen, seventeen, eighteen, nineteen, twenty, or even more substitutions in comparison to the corresponding native lipocalin, provided that such a lipocalin mutein is capable of binding to an immune checkpoint protein with detectable affinity. For example, a lipocalin mutein can have a substitution at a position corresponding to a distinct position (i.e. at a corresponding position) of the wild-type lipocalin having the wild-type sequence of, for example, tear lipocalin, lipocalin 2, or any other lipocalin disclosed herein.

In some embodiments a lipocalin mutein of the combination according to the disclosure includes at least two amino acid substitutions, including 2, 3, 4 or 5, sometimes even more, amino acid substitutions of a native amino acid by an arginine residue. Accordingly, the nucleic acid of a lipocalin 'reference' scaffold as described herein is subject to mutagenesis with the aim of generating a lipocalin mutein which is capable of binding to an immune checkpoint protein with detectable affinity.

Likewise, a lipocalin mutein of the present disclosure may lack 1, 2, 3, 4 or more amino acids at its N-terminal end and/or 1, 2 or more amino acids at its C-terminal end, in comparison to the respective wild-type lipocalin.

Specifically, in order to determine whether an amino acid residue of the amino acid sequence of a lipocalin mutein different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the lipocalin mutein retains its capability to bind to an immune checkpoint protein with detectable affinity, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gln);
d. Arginine (Arg), Lysine (Lys);
e. Isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met).

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the lipocalin are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, isoleucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of the respective lipocalin also may be substituted, generally with serine, to improve the oxidative stability of the molecule and prevent aberrant crosslinking. Conversely, cysteine bond (s) may be added to the lipocalin to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of a lipocalin as long as these deletions or insertion result in a stable folded/functional mutein.

Modifications of the amino acid sequence of a wild type lipocalin of the disclosure include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the lipocalin mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example, one or more fusion partners, e.g. peptides, proteins or protein domains, or for the formation of non-naturally occurring disulphide linkages.

It is also possible to mutate other amino acid sequence positions to cysteine in order to introduce new reactive groups, for example, one or more fusion partners, e.g. peptides, proteins or protein domains, or for the formation of non-naturally occurring disulphide linkages. If one of the above fusion partners is conjugated to a lipocalin mutein of the disclosure, conjugation to an amino acid side chain can be advantageous. Suitable amino acid side chains may occur naturally in the amino acid sequence of a human lipocalin or may be introduced by mutagenesis. In case a suitable binding site is introduced via mutagenesis, one possibility is the replacement of an amino acid at the appropriate position by a cysteine residue.

With respect to a mutein of human lipocalin 2, exemplary possibilities of such a mutation to introduce a cysteine residue into the amino acid sequence of a lipocalin including human Lipocalin 2 mutein to include the introduction of a cysteine (Cys) residue at, at least, one of the sequence positions that correspond to sequence positions 14, 21, 60, 84, 88, 116, 141, 145, 143, 146 or 158 of the wild type sequence of hNGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No. P80188.

In some embodiments, a lipocalin mutein as comprised in a multi-specific polypeptide disclosed herein, is fused at its N-terminus or its C-terminus to a heterologous amino acid sequence, without affecting the biological activity (binding to its target(s) e.g. an immune checkpoint protein) of the polypeptide, such as, a protein (e.g. an immunoglobulin), a protein domain or a peptide, for instance, a signal sequence and/or an affinity tag.

Affinity tags such as the STREP-TAG® or STREP-TAG® II (also described in Schmidt, T. G. M. et al. (1996) J Mol. Biol. 255, 753-766), the myc-tag, the FLAG-tag, the His6-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for lipocalin muteins of the disclosure as well.

In general, it is possible to label the lipocalin muteins and the polypeptides thereof, as disclosed herein, with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulin) can also be used for conjugation to the lipocalin muteins of the disclosure. The lipocalin muteins of the disclosure and the polypeptides thereof may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the disclosure and the polypeptides thereof may, however, also be conjugated with therapeutically active nucleic acids such as antisense nucleic acid molecules, small interfering RNAs, micro RNAs or ribozymes. Such conjugates can be produced by methods well known in the art.

In addition, in some embodiments, a lipocalin mutein of the disclosure as comprised in a multi-specific polypeptide disclosed herein can be fused to a fusion partner that may confer new characteristics to the lipocalin muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a lipocalin mutein of the disclosure as comprised in a fusion polypeptide disclosed herein with a separate enzyme active site such that both subunits of the resulting polypeptide together act on a given therapeutic target. In some embodiments, the binding domain of the lipocalin mutein may attach to the disease-causing target, allowing the enzyme domain to abolish the biological function of the target.

In another embodiment, the multi-specific polypeptide of the disclosure may be conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold.

In another embodiment, the multi-specific polypeptide is conjugated to a compound that extends the serum half-life of the multi-specific polypeptide. More preferably, the multi-specific polypeptide is conjugated to a compound selected from the group consisting of a polyalkylene glycol molecule, a hydroethylstarch, a CH3 domain of an immunoglobulin, a CH4 domain of an immunoglobulin, an albumin binding peptide, and an albumin binding protein.

In case hNGAL muteins are comprised in the multi-specific polypeptide, at each of eleven sequence positions Ser 14, Asn 21, Glu 60, Val 84, Gln 88, Asn 116, Thr 141, Glu 143, Ala 145, Ser 146 and Ser 158, a Cys residue can be introduced which then can be used for site specific conjugation such as PEGylation.

In another embodiment, the present disclosure also relates to nucleic acid molecules (DNA and RNA) that include nucleotide sequences encoding the lipocalin muteins or multi-specific polypeptides disclosed herein. In yet another embodiment, the disclosure encompasses a host cell containing said nucleic acid molecule. Since the degeneracy of the genetic code permits substitutions of certain codons by other codons specifying the same amino acid, the disclosure is not limited to a specific nucleic acid molecule encoding a multi-specific polypeptide as described herein but encompasses all nucleic acid molecules that include nucleotide sequences encoding a functional polypeptide. In this regard, the present disclosure also relates to nucleotide sequences encoding the lipocalin muteins or the multi-specific polypeptides of the disclosure.

In some embodiments, a nucleic acid molecule encoding a lipocalin mutein disclosed in this application, such as DNA, may be "operably linked" to another nucleic acid molecule encoding an immunoglobulin of the disclosure to allow expression of a multi-specific polypeptide disclosed herein. In this regard, an operable linkage is a linkage in which the sequence elements of one nucleic acid molecule and the sequence elements of another nucleic acid molecule are connected in a way that enables expression of the fusion polypeptide as a single polypeptide.

The disclosure also relates to a method for the production of a lipocalin mutein or a multi-specific polypeptide of the disclosure is produced starting from the nucleic acid coding for the mutein or the polypeptide or any subunit therein by means of genetic engineering methods. In some embodiments, the method can be carried out in vivo, the polypeptide can, for example, be produced in a bacterial or eucaryotic host organism and then isolated from this host organism or its culture. It is also possible to produce a mutein or a fusion polypeptide of the disclosure in vitro, for example by use of an in vitro translation system.

When producing the mutein or the fusion polypeptide in vivo, a nucleic acid encoding such mutein or polypeptide is introduced into a suitable bacterial or eukaryotic host organism by means of recombinant DNA technology (as already outlined above). For this purpose, the host cell is first transformed with a cloning vector that includes a nucleic acid molecule encoding a mutein or a fusion polypeptide as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In one embodiment of the disclosure, the method includes subjecting at least one nucleic acid molecule encoding hNGAL to mutagenesis at nucleotide triplets coding for at least one, sometimes even more, of the sequence positions corresponding to the sequence positions 28, 40-52, 60, 68, 65, 70, 71-81, 87, 89, 96, 98, 100-106, 114, 118, 120, 125-137 and 145 of the linear polypeptide sequence of hNGAL (SEQ ID NO: 1).

In addition, in some embodiments, the naturally occurring disulphide bond between Cys 76 and Cys 175 may be removed in hNGAL muteins of the disclosure. Accordingly, such muteins can be produced in a cell compartment having a reducing redox milieu, for example, in the cytoplasma of Gram-negative bacteria.

The disclosure also includes nucleic acid molecules encoding the lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the lipocalin muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a multi-specific polypeptide as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a mutein or a multi-specific polypeptide as described herein (for example, SEQ ID NOs: 85 and 86), and in particular a cloning vector containing the coding sequence of such a polypeptide can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a mutein or a multi-specific polypeptide of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HeLa cells or CHO cells) or primary mammalian cells.

In some embodiments where a lipocalin mutein of the disclosure, including as comprised in a fusion polypeptide disclosed herein, includes intramolecular disulphide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favours the formation of structural disulphide bonds.

In some embodiments, it is also possible to produce a mutein or a multi-specific polypeptide of the disclosure in the cytosol of a host cell, preferably *E. coli*. In this case, the mutein or the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

In some embodiments, a mutein or a multi-specific polypeptide of the disclosure as described herein may be not necessarily generated or produced only by use of genetic engineering. Rather, such mutein or polypeptide can also be obtained by chemical synthesis such as Merrifield solid phase polypeptide synthesis or by in vitro transcription and translation. It is, for example, possible that promising mutations are identified using molecular modeling and then to synthesize the wanted (designed) mutein or polypeptide in vitro and investigate the binding activity for a target of interest. Methods for the solid phase and/or solution phase synthesis of proteins are well known in the art (see e.g. Bruckdorfer, T. et al. (2004) *Curr. Pharm. Biotechnol.* 5, 29-43).

In another embodiment, a mutein or a fusion polypeptide of the disclosure may be produced by in vitro transcription/translation employing well-established methods known to those skilled in the art.

The skilled worker will appreciate methods useful to prepare muteins or multi-specific polypeptides contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutein gene or a polypeptide gene or its parts by incorporating cleavage sites for certain restriction enzymes. In addition, these mutations can also be incorporated to further improve the affinity of a mutein or a multi-specific polypeptide for its targets (e.g. a tumor-associated antigen and an immune checkpoint protein). Furthermore, mutations can be introduced to modulate certain characteristics of the mutein or the polypeptide such as to improve folding stability, serum stability, protein resistance or water solubility or to reduce aggregation tendency, if necessary. For example, naturally occurring cysteine residues may be mutated to other amino acids to prevent disulphide bridge formation.

In still another aspect, the disclosure encompasses the use of one or more multi-specific polypeptides of the disclosure or of one or more compositions comprising such multi-specific polypeptides for simultaneously binding of a tumor-associated antigen and an immune checkpoint protein in a subject and/or simultaneously inhibiting the binding of a tumor-associated antigen and an immune checkpoint protein to their respective receptor(s) or ligand(s) in a subject.

In still another aspect, the present disclosure features a method of simultaneously binding a tumor-associated antigen and an immune checkpoint protein in a subject, comprising administering to said subject an effective amount of one or more multi-specific polypeptides of the disclosure or of one or more compositions comprising such polypeptides.

In still another aspect, the present disclosure involves a method for simultaneously inhibiting the binding of a tumor-associated antigen and an immune checkpoint protein to their respective receptor(s) or ligand(s) in a subject, comprising administering to said subject an effective amount of one or more multi-specific polypeptides of the disclosure or of one or more compositions comprising such proteins.

In some further embodiments, a multi-specific polypeptide of the disclosure may have a binding affinity for an immune checkpoint protein as good as or superior to that of the lipocalin mutein specific for the immune checkpoint protein as included in such polypeptide.

In a related embodiment, a multi-specific polypeptide of the disclosure may be able to block binding of an immune checkpoint protein to its receptor or ligand with an 1050 value at least as good as or superior to the 1050 value of the lipocalin mutein specific for that immune checkpoint protein as included in such polypeptide.

In some further embodiments, a multi-specific polypeptide of the disclosure may have a binding affinity for a tumor-associated antigen as good as or superior to that of the immunoglobulin specific for that tumor-associated antigen as included in such polypeptide.

In a related embodiment, a multi-specific polypeptide of the disclosure may be able to block binding of a tumor-associated antigen to its receptor or ligand with an 1050 value at least as good as or superior to the 1050 value of the immunoglobulin specific for the tumor-associated antigen as included in such polypeptide.

In some other embodiments, a multi-specific polypeptide of the disclosure may have a binding affinity of a $K_D$ of about 200 nM or less for an immune checkpoint protein, such as 100 nM or less, 10 nM or less, 1 nM or less, 0.5 nM or less, 0.3 nM or less, or 0.2 nM or less.

In some additional embodiments, a multi-specific polypeptide of the disclosure may have binding affinity of a $K_D$ of about 200 nM or less for a tumor-associated antigen, such as 100 nM or less, 10 nM or less, 1 nM or less, 0.5 nM or less, 0.3 nM or less, or 0.2 nM or less.

The disclosure also includes a method of treating cancer, preferably lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, t-cell lymphoma, cutaneous T cell lymphoma (CTCL), and combinations of said cancers, the method comprising administering a pharmaceutical composition containing a multi-specific polypeptide as described herein to a subject in need thereof.

A. Multi-Specific Polypeptide for Her2/Neu Receptor and CTLA-4

In one embodiment, the multi-specific polypeptide of the disclosure comprises a first immunoglobulin binding domain capable of binding to Her2/neu receptor of a human and/or an animal (e.g. non-chimpanzee primate) and a second lipocalin mutein binding domain capable of binding to cytotoxic T lymphocyte associated antigen (CTLA-4) of a human and/or an animal (e.g. non-chimpanzee primate).

In a further embodiment, the immunoglobulin binding domain comprises a full-length immunoglobulin or an antigen-binding domain thereof specific for Her2/neu receptor, and a second binding domain that comprises a lipocalin mutein specific for CTLA-4.

In some still further embodiments, the lipocalin mutein binding domain can be fused at its N-terminus and/or its C-terminus to the immunoglobulin binding domain. For example, one or more lipocalin mutein binding domains can be linked to the immunoglobulin binding domain as essentially described in FIG. 1. In this regard, one or more lipocalin muteins can be linked, via a peptide bond, to the C-terminus of the immunoglobulin heavy chain domain (VH), the N-terminus of the VH, the C-terminus of the immunoglobulin light chain (VL), and/or the N-terminus of the VL (cf. FIG. 1). In some particular embodiments, the lipocalin mutein may be linked via a peptide bond between (i) the N-terminus of the lipocalin and (ii) the C-terminus of a heavy chain constant region (CH) or the C-terminus of a light chain constant region (CL) of the immunoglobulin. In some still further embodiments, the peptide bond may be a Serine Glycine linker, for example, as shown in SEQ ID NO: 87.

In one aspect, the multi-specific polypeptide is an inhibitor of Her2/neu receptor.

In some embodiments, the immunoglobulin is a monoclonal antibody that interferes with the Her2/neu receptor.

In some further embodiments, when contained in the multi-specific polypeptide, the Fc region of Reference Molecule 1 can bind to Fc receptor III (RIII) present on the surface of effector cells from the immune system and trigger tumor cell death via ADCC.

In another aspect, the multi-specific polypeptide is an antagonist of CTLA-4.

B. Lipocalin Mutein Binding Domain of Multi-Specific Polypeptide and Lipocalin Mutein Capable of Binding CTLA-4

In one embodiment, the lipocalin mutein binding domain comprises a lipocalin mutein that is capable of binding CTLA-4 with an affinity measured by a $K_D$ of about 1 nM or lower. In another aspect, the disclosure provides a lipocalin mutein that is capable of binding CTLA-4 with an affinity measured by a $K_D$ of about 1 nM or lower. In some preferred embodiments, the lipocalin mutein has an affinity measured by a $K_D$ of about 0.8 nM or 0.6 nM or lower, i.e., in the picomolar range. In another embodiment, the lipocalin mutein is capable of competing with human CD80/B7.1 for binding to human CTLA-4 in a competition assay preferably with an EC50 value of about 15 nM or lower, such as about 10 nM, about 8 nM or about 6 nM, for example, when measured in an assay essentially described in Example 7.

In some other embodiments, the disclosure provides a CTLA-4-binding lipocalin mutein that is more thermal stable than the lipocalin mutein of SEQ ID NO: 4, for example, when measured as essentially described in Example 9.

In some further embodiments, the lipocalin mutein may include at one or more positions corresponding to position 44, 50, 79, 81, 98, 104, 125, 127, 128, 130 and/or 134 of the linear polypeptide sequence of human Lipocalin 2 (Lcn 2) or hNGAL (SEQ ID NO: 1) a substitution.

In particular, the lipocalin mutein may comprise 1, 2, 3, 4, 5, 6, 7, 8, 9, 10, 11, 12, 13, 14, 15 or even more, such as all, substitution(s) at sequence position(s) corresponding to sequence position 28, 40, 44, 46-47, 49, 50, 60, 70, 71-73, 77, 79, 81, 87, 98, 101-104, 114, 118, 120, 125-128, 130, 132, 134, 137 and/or 145 of the linear polypeptide sequence of hNGAL (SEQ ID NO: 1).

In further particular embodiments, the lipocalin mutein comprises an amino acid sequence selected from the group consisting of SEQ ID NOs: 2-62, 65-84 and 87-96 or of a fragment or variant thereof. In some still further embodiments, the lipocalin mutein has at least 80% identity to the sequence selected from the group consisting of SEQ ID NOs: 2-62, 65-84 and 87-96, such as 85%, 90%, 95% and 99% identity.

In another embodiment, the lipocalin mutein has at least 70% identity to the sequence of a wild-type human lipocalin, including human lipocalin 2 or hNGAL, such as 80%, 85%, 90% and 95% identity.

In some embodiments, the lipocalin mutein has a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin mutein is effective to bind CTLA-4 as given non-natural target with detectable affinity.

In some embodiments, the lipocalin mutein may differs from the sequence of wild type hNGAL (SEQ ID NO: 1) at positions 40, 44, 46, 47, 49, 50, 60, 70, 71, 72, 73, 77, 79, 81, 87, 101, 102, 103, 104, 114, 118, 120, 125, 126, 127, 128, 130, 132, 134, 137 and 145. Hence, in addition to one or more substitutions at positions corresponding to positions 28, 44, 50, 79, 81, 98, 104, 125, 127, 128, 130 and/or 134 of the linear polypeptide sequence of hNGAL (SEQ ID NO: 1), the lipocalin mutein may comprise at one or more positions corresponding to positions 40, 46, 47, 49, 60, 70, 71, 72, 73, 77, 87, 101, 102, 103, 104, 114, 118, 120, 126, 132, 137 and/or 145 of the linear polypeptide sequence of hNGAL (SEQ ID NO: 1) a substitution.

In some further embodiments, the lipocalin mutein may have one or more following acid substitutions in comparison to the sequence of wild type hNGAL (Lcn2). A substitution at sequence position 44 may for example be a substitution Glu 44→Asp, Gln, Ser, Asn, Tyr, His, Thr, Arg, Met or Leu. A substitution at sequence position 50 may for example be a substitution Lys 50→Asn, Gln, Asp, Leu, Pro, Ser or Arg. A substitution at sequence position 79 may for example be a substitution Trp 79→Thr, Pro or Ser. A substitution at sequence position 81 may for example be a substitution Arg 81→Ala. A substitution at sequence position 98 may for example be a substitution Lys 98→Arg. A substitution at sequence position 104 may for example be a substitution Thr 104→Trp, Val, Glu, Leu, Arg, Ile, Met, Gly or Phe. A substitution at sequence position 125 may for example be a substitution Lys 125→Leu, His, Arg, Gln or Tyr. A substitution at sequence position 127 may for example be a substitution Ser 127→Glu, Asn, Gly or Asp. A substitution at sequence position 128 may for example be a substitution Gln 128→Asp, Thr, His, Phe, Gly, Pro, Arg or Ser. A substitution at sequence position 130 may for example be a substitution Arg 130→Ala, Tyr, Phe, Ser or Asp. A substitution at sequence position 134 may for example be a substitution Lys 134→Ala or Ser.

Moreover, a substitution at sequence position Ala 40 may for example be a substitution Ala 40→Arg or Tyr. A substitution at sequence position 46 may for example be a substitution Lys 46→Gln or Arg. A substitution at sequence position 47 may for example be a substitution Asp 47→His or Tyr. A substitution at sequence position 49 may for example be a substitution Gln 49→Met. A substitution at sequence position 60 may for example be a substitution Glu 60→Gly. A substitution at sequence position 70 may for example be a substitution Leu 70→Ile. A substitution at sequence position 71 may for example be a substitution Phe 71→Ser or Leu. A substitution at sequence position 72 may for example be a substitution Arg 72→Ser, Pro or Asp. A substitution at sequence position 73 may for example be a substitution Lys 73→His or Thr. A substitution at sequence position 77 may for example be a substitution Asp 77→Glu, Val or Leu. A substitution at sequence position 101 may for example be a substitution Pro 101→Gly or Arg. A substitution at sequence position 102 may for example be a substitution Gly 102→Asp or Met. A substitution at sequence position 103 may for example be a substitution Leu 103→Lys or Asp. A substitution at sequence position 114 may for example be a substitution Asn 114→Asp. A substitution at sequence position 118 may for example be a substitution His 118→Tyr. A substitution at sequence position 120 may for example be a substitution Met 120→Val. A substitution at sequence position 126 may for example be a substitution Val 126→Ala. A substitution at sequence position 132 may for example be a substitution Tyr 132→Ser, Phe or His. A substitution at sequence position 137 may for example be a substitution Leu 137→Ile. A substitution at sequence position 145 may for example be a substitution Thr 145→Ala.

In some further embodiments, the hNGAL mutein may comprise, compared to the sequence of the hNGAL wild type amino acid sequence, one or more amino acid replacements selected from the group consisting of: L(42)→W, Y(78)→H, I(80)→T, F or V, Q(88)→R, P(89)→A or T, N(96)→D, Y(106)→H, K(124)→E or Q, N(129)→D, E(131)→G and I(135)→V.

In one embodiment, the lipocalin mutein may include one of the following amino acid replacements:

(a) Glu 44→Asp; Lys 50→Asn; Trp 79→Thr; Arg 81→Ala; Lys 125→Leu; Ser 127→Glu; Gln 128→Asp; Arg 130→Ala; Lys 134→Ala;

(b) Glu 44→Asp; Lys 50→Asp; Trp 79→Pro; Arg 81→Ala; Thr 104→Trp; Lys 125→His; Ser 127→Asp; Gln 128→Thr; Arg 130→Tyr; Lys 134→Ser;

(c) Glu 44→Gln; Lys 50→Leu; Trp 79→Pro; Arg 81→Ala; Thr 104→Val; Lys 125→His; Ser 127→Asp; Gln 128→Thr; Arg 130→Tyr; Lys 134→Ser;

(d) Glu 44→Asp; Lys 50→Pro; Trp 79→Pro; Arg 81→Ala; Thr 104→Trp; Lys 125→His; Ser 127→Asp; Gln 128→Ser; Arg 130→Tyr; Lys 134→Ser;

(e) Glu 44→Ser; Lys 50→Arg; Trp 79→Thr; Arg 81→Ala; Thr 104→Trp; Lys 125→His; Ser 127→Asp; Gln 128→Thr; Arg 130→Tyr; Lys 134→Ser;

(f) Glu 44→Ser; Lys 50→Pro; Trp 79→Ser; Arg 81→Ala; Thr 104→Glu; Lys 125→Tyr; Gln 128→Asp; Arg 130→Asp; Lys 134→Ser; or (g) Glu 44→Leu; Lys 50→Pro; Trp 79→Pro; Arg 81→Ala; Lys 98→Arg; Lys 125→His; Ser 127→Asp; Gln 128→Thr; Arg 130→Tyr; Lys 134→Ser.

In addition to the above mutations, the hNGAL mutein may further comprise one or more of the amino acid replacements selected from the group consisting of: Glu 28→His or Gln, Cys 87→Ser, and Thr 145→Ala or Thr. A further mutation that can be present in an hNGAL mutein is having an Ala residue at the sequence position corresponding to sequence position 81 and/or sequence position 125, or sequence position 134 of hNGAL. Moreover, the sequence position 114 in hNGAL may have an influence on the thermal stability of the mutein. Replacing the residue naturally present at position 114 of hNGAL can increase the melting temperature of the mutein significantly. In one embodiment, a charged amino acid may be introduced at sequence position 114 of the hNGAL mutein, compared to the hNGAL wild type sequence. The charged amino acid can be a positively or a negatively charged amino acid. In one preferred embodiments, the charged amino acid is a negatively charged amino acid. This negatively charged amino acid may be Asp or Glu. However, it is also possible to introduce an artificial amino acid that provides a negative charge, for example.

In yet other embodiments, the hNGAL mutein may comprise (in addition or alternatively to the above-mentioned mutations at any of positions 28, 87, 145) an amino acid replacement at one or more of the sequence positions that correspond to sequence positions 55, 65, 88, 114, 116, 118, 120 of the wild type sequence of hNGAL, which are outside the 4 loops compared to the sequence of the hNGAL wild type amino acid. For example, compared to the hNGAL wild type amino acid sequence, the hNGAL mutein may have at least one of the amino acid substitutions selected from I(55)→V, N(65)→D or Q, Q(88)→R, N(114)→D, N(116)→S, H(118)→Y, M(120)→T or V.

In some further embodiments, with respect to the hNGAL mutein, a Ser, Leu, Val, His, He or Thr residue can be present at sequence position 71 compared to the wild type sequence of the mature hNGAL and a hydrophilic amino acid, for example Thr or Ser, or a Pro residue can be present at sequence position 72 compared to the wild type sequence of the mature hNGAL. Other examples of possible amino acid substitutions in the 4 loop regions that form the binding site, compared to the wild type sequence of the mature hNGAL, are the replacement of the Lys residue at position 50 by a Glu, Gln or Asp residue, the replacement of the Lys residue at position 46 by Gln or Arg residue, the replacement of Trp at position 79 by a Thr or a Pro residue, the replacement of Gly at position 102 by an Asp or a Met residue, the replacement of Ala at position 125 by a Leu or Gln residue and the replacement of Arg at position 130 by an Ala or Thr residue, to name only a few illustrative examples in case hNGAL is used as scaffold for the generation of muteins as part of the mutI-specific polypeptides disclosed herein.

The numbering is preferably in relation to the linear polypeptide sequence of SEQ ID NO: 1. Accordingly, given the teaching of the disclosure as described above, a skilled artisan can readily determine which amino acids in a lipocalin mutein correspond to those described in the preferred reference sequence of hNGAL (SEQ ID NO: 1) so as to mutate said amino acids in said lipocalin mutein.

Noteworthy, the amino acid substitutes in a lipocalin mutein contemplates that the corresponding amino acid in the reference sequence (e.g. SEQ ID NO: 1) can be exchanged by a corresponding conservative amino acid. In particular, conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In some embodiments, the amino acid sequence of a lipocalin mutein specific for CTLA-4 disclosed herein has a high sequence identity to mature hNGAL (SWISS-PROT Data Bank Accession Number P80188) when compared to sequence identities with other lipocalins. In this general context, the amino acid sequence of a hNGAL mutein of the disclosure is at least substantially similar to the amino acid sequence of mature hNGAL, with the proviso that possibly there are gaps (as defined above) in an alignment that are the result of additions or deletions of amino acids. A respective sequence of a lipocalin mutein specific for CTLA-4 of the disclosure, being substantially similar to the sequences of mature hNGAL, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of mature hNGAL, with the proviso that the altered position or sequence is retained and that one or more gaps are possible.

Numerous possible applications for the CTLA-4 binding muteins of the disclosure exist in medicine. For example, the disclosure relates to a lipocalin mutein as defined above for the treatment of a disease or disorder associated with an altered, e.g. increased or reduced, level of CTLA-4.

In yet another aspect the disclosure relates to the use of a CTLA-4 binding mutein in diagnosis. For example, the disclosure also relates to a mutein as defined above for the diagnosis of a disease or disorder associated with an altered, e.g. increased or reduced, level of CTLA-4.

In principle, a CTLA-4 binding mutein of the disclosure can be used in any therapeutic application in which binding of CTLA-4 to a physiological ligand, such as B7-1 or B7-2 is involved. Examples of such therapeutic applications include, but are not limited to, the prevention and/or treatment of cancer or the prevention and/treatment of an infectious disease. In such application, an anti-CTLA-4 lipocalin mutein is administered to a mammal, for example, a human, a dog, an ape, a rat, a mouse, in an amount of that is effective in treating said cancer or that infectious disease.

The infectious diseases may be caused by exposure to a particular toxin or pathogen. Similar to its application to tumors as discussed below, CTLA-4 blockade that is mediated by a CTLA-4 binding lipocalin mutein, and surrogate therapeutic endpoint can be used alone, or as an adjuvant, in combination with vaccines, to stimulate the secondary or memory immune response to pathogens, toxins, and self-antigens. CTLA-4 blockade has been shown to be effective in the acute phase of infections of *Nippostrongylus brasiliensis* (McCoy, K. et al. (1997) 186 (2); 183-187) and *Leishmania donovani* (Murphy, M. et al. (1998) J. Immunol. 161: 4153-4160). Examples of pathogens for which this therapeutic approach may be particularly useful include pathogens for which there is currently no effective vaccine, or pathogens for which conventional vaccines are of limited effectiveness. These include, but are not limited to HIV, Hepatitis (A, B, & C), Influenza, Herpes, *Giardia*, Malaria, *Leishmania, Staphylococcus aureus*, and *Pseudomonas aeruginosa*. CTLA-4 blockade is particularly useful in boosting immunity against established infections by agents such as HIV that present altered antigens over the course of the infections. These epitopes are recognized as foreign at the time of administration of the CTLA-4 binding compound/mutein of the disclosure, thus provoking a strong T cell response that is not dampened by negative signals through CTLA-4. Some examples of pathogenic viruses causing infections treatable by using CTLA-4 binding lipocalin muteins of the disclosure include hepatitis (A, B, or C), herpes virus (e. g., VZV, HSV-1, HAV-6, HSV-11, and CMV, Epstein Barr virus), adenovirus, influenza virus, flaviviruses, echovirus, rhinovirus, coxsackie virus, cornovirus, respiratorysyncytial virus, mumps virus, rotavirus, measles virus, rubella virus, parvovirus, vaccina virus, HTLV virus, dengue virus, papillomavirus, molluscum virus, poliovirus, rabies virus, JC virus and arboviral encephalitis virus, to name only a few. Some examples of pathogenic bacteria causing infections treatable by CTLA-4 binding lipocalin muteins include *chlamydia*, rickettsial bacteria, mycobacteria, staphylococci, streptococci, pneumonococci, meningococci and conococci, *klebsiella, proteus, serratia, pseudomonas, legionella*, diphtheria, *salmo-*

*nella*, bacilli, cholera, tetanus, botulism, anthrax, plague, leptospirosis, and Lyme disease bacteria. Some examples of pathogenic fungi causing infections treatable by CTLA-4 binding lipocalin muteins include *Candida* (*albicans, krusei, glabrata, tropicalis*, etc.) *Cryptococcus neoformans, Aspergillus* (*fumigatus, niger* etc.), Gefaus Mucorales (*Mucor, Absidia*, Rhizophus), *Sporothrix schenkii, Blastomyces dermatitidis, Paracoccidioides brasiliensis, Coccidioidesimmitis* and *Histoplasma capsulatum*. Some examples of pathogenic parasites causing infections treatable by CTLA-4 binding muteins include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In addition, the current disclosure provides a method of treating a tumor or cancer, the method comprising administering a pharmaceutical composition as described herein containing a lipocalin mutein of the disclosure to a subject in need thereof. Likewise, the disclosure relates to a CTLA-4 binding lipocalin mutein for use in treating a tumor or cancer. Similarly, the disclosure concerns the use of a mutein of the disclosure for the preparation of a pharmaceutical composition for treating a tumor or cancer. The cancer or tumor to be treated is not particularly limited, and specific examples may include lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, t-cell lymphoma, cutaneous T cell lymphoma (CTCL), and combinations of said cancers.

When applied for the treatment of cancer, the CTLA-4 binding compound or mutein can be administered to a mammal in combination with another pharmaceutically active agent. Examples of such agents include, but are not limited to, a chemotherapeutic or anti-tumor agent, a cancer vaccine, an immunomodulatory agent, an anti-angiogenesis agent, an anti-vascular agent, a signal transduction inhibitor, an antiproliferative agent, an apoptosis inducer, a chemokine, a cytokine and an inhibitor of a survival pathway.

In one preferred embodiment, the CTLA-4 binding lipocalin mutein is administered in combination with an anti-angiogenesis agent. Examples of suitable anti-angiogenesis are a MMP-2 (matrix-metalloproteinase 2) inhibitor, an MMP-9 (matrix-metalloproteinase 9) inhibitor, and a COX-II (cyclooxygenase II) inhibitor, to name only a few.

In another preferred embodiment, the CTLA-4 binding lipocalin mutein is administered in combination with a chemotherapeutic agent. The chemotherapeutic agent may be a mitotic inhibitor, alkylating agent, anti-metabolite, intercalating antibiotic, growth factor inhibitor, cell cycle inhibitor, enzyme, topoisomerase inhibitor, biological response modifier, anti-hormone, angiogenesis inhibitor, or an anti-androgen.

In yet another presently preferred embodiment, the CTLA-4 binding lipocalin mutein is administered in combination with a signal transduction inhibitor. Examples of suitable signal transduction inhibitors include, but are not limited to, an EGFR (epidermal growth factor receptor) inhibitor, VEGF (vascular endothelial growth factor) inhibitor, and an erbB2 receptor inhibitor.

In yet another preferred embodiment, the CTLA-4 binding lipocalin mutein is administered in combination with a cytokine. Illustrative examples of suitable cytokines for use in the present disclosure include Interleukin-2 (IL-2), Interferon-gamma (IFN-g), granulocyte/macrophage colony-stimulating factor (GM-CSF), Interferon-12 (IL-12), Interferon-18 (IL-18), and SL cytokine precursor (FLT-3L).

It is also encompassed in the present disclosure to administer to a mammal an amount of a CTLA-4 binding lipocalin mutein in combination with radiation therapy. The amount of the lipocalin mutein in combination with the radiation therapy is effective in inhibiting abnormal cell growth or treating the hyperproliferative disorder in the mammal.

In another therapeutic application, a CTLA-4 binding mutein is employed for the treatment or prevention of T cell mediated disease or tumor types expressing CTLA-4 in a mammal. For this purpose, a fusion or conjugate of an anti-CTLA-4 lipocalin mutein as described herein with a toxin can be used. The amount of said fusion or conjugate is chosen such that it is effective in treating said T cell mediated disease or tumor.

Examples of T cell mediated diseases that can be treated in this manner include graft versus host disease, transplant rejection or auto-immune diseases such as multiple sklerosis, lupus erythematosus, myasthenia gravis, rheumatoid arthritis or diabetes mellitus. For the same purpose, polyvalent formulations of CTLA-4 binding muteins that cross-link cell surface CTLA-4 and act as a CTLA-4 agonist might be used instead of a conjugate or fusion of a anti-CTLA-4 lipocalin mutein with a toxin (see, e. g., Krummel and Allison, 1996, J. Exp. Med. 183, 2533-2540, cf. also International patent application WO 01/14424). A polyvalent formulation of CTLA-4 binding muteins that acts as an agonist can be prepared by covalently crosslinking two or more of the muteins using respective cross-linking reagents. Alternatively, CTLA-4 binding muteins can be cross-linked to each other by non-covalent interactions. For this purpose, they can for example, be conjugated to or fused to an oligomerization module such as a leucine zipper, a jun/fos oligomerization module or an immunoglobulin domain. Non-covalent oligomerization and thus formation of a preparation of polyvalent CTLA-4 muteins then occurs via this oligomerization module. In accordance with this approach, a polyvalent CTLA-4 cross-linking lipocalin mutein will transduce a negative signal similar to the signal elicited by the natural ligand and inhibit, reduce or prevent activation, expansion or effector activities of the CTLA-4 expressing T cell. Accordingly, a pharmaceutical composition wherein the at least two CTLA-4 binding muteins are (cross)-linked to each other to form a multimer, for example, a dimer, trimer or higher oligomer is also encompassed in the present disclosure. As mentioned above, a dimeric fusion protein in which two CTLA-4 binding molecules (which can be formed either by two different CTLA-4 binding muteins or two molecules of the same CTLA-4 binding mutein) are fused to each other can be used in such a pharmaceutical composition.

In still another aspect, the present application features a diagnostic or analytical kit comprising a lipocalin mutein of the disclosure.

The subject in need of such a treatment may be a mammal, such as a human, a dog, a mouse, a rat, a pig, an ape such as cynomolgous monkeys to name only a few illustrative examples, with human being preferred.

In still another aspect, the present application features a method for in vivo imaging in a subject, including administering to said subject a lipocalin mutein of the disclosure or a pharmaceutical composition comprising a lipocalin mutein of the disclosure. The subject may be defined as above.

C. Uses and Exemplary Examples of Multi-Specific Polypeptide for Her2/Neu Receptor and CTLA-4

In some embodiments, a multi-specific polypeptide according to the disclosure binds CTLA-4 with a $K_D$ of 100 μM or less, including about 5 μM or less, about 500 nM, 200 nM or less, 100 nM or less, 10 nM or less, 1 nM or less, 0.5 nM or less, 0.3 nM or less, or 0.2 nM or less. The multi-specific polypeptide may specifically bind one or more continuous, discontinuous or conformation epitope(s) of the mature, folded bioactive form of CTLA-4.

In some preferred embodiments, a multi-specific polypeptide of the disclosure binds to CTLA-4 with an affinity by a $K_D$ of about 1 nM or lower, in some cases, about 0.8 or 0.6, 0.5, 0.4, 0.3 nM and below. Thus, the multi-specific polypeptide may be in the picomolar range which is an outstanding property of a binding molecule.

In some embodiments, a multi-specific polypeptide according to the disclosure binds Her2/neu with a $K_D$ of 100 μM or less, including about 5 μM or less, about 500 nM, 200 nM or less, 100 nM or less, 10 nM or less, 1 nM or less, 0.5 nM or less, 0.3 nM or less, or 0.2 nM or less. The multi-specific polypeptide may specifically bind one or more continuous, discontinuous or conformation epitope(s) of the mature, folded bioactive form of Her2/neu.

In some preferred embodiments, a multi-specific polypeptide of the disclosure binds to Her2/neu with an affinity by a $K_D$ of about 1 nM or lower, in some cases, about 0.8 or 0.6, 0.5, 0.4, 0.3 nM and below. Thus, the multi-specific polypeptide may be in the picomolar range which is an outstanding property of a binding molecule.

The binding affinity of a polypeptide to a selected target (e.g. CTLA-4 or Her2/neu), can be measured (and thereby $K_D$ values of a polypeptide-target complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art.

It is also noted that the complex formation between the respective polypeptide and its target is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective polypeptide and its target) may vary within a certain experimental range, depending on the method and experimental setup that is used for determining the affinity of a particular polypeptide for a given target. This means that there may be a slight deviation in the measured $K_D$ values or a tolerance range depending, for example, on whether the $K_D$ value was determined by surface plasmon resonance (Biacore), by competition ELISA, or by "direct ELISA."

In some further embodiments, the multi-specific polypeptide may have a binding affinity for CTLA-4 as good as or superior to that of the lipocalin mutein specific for CTLA-4 as included in such polypeptide of the disclosure, such as lipocalin muteins selected from the group consisting of SEQ ID NOs: 2-62, 65-84 and 87-96.

In a related embodiment, the multi-specific polypeptide may be able to block binding of CTLA-4 to its ligand with an 1050 value at least as good as or superior to the 1050 value of the lipocalin mutein specific for CTLA-4 as included in such polypeptide of the disclosure, such as lipocalin muteins selected from the group consisting of SEQ ID NOs: 2-62, 65-84 and 87-96, for example, when said lipocalin mutein and the polypeptide are measured in an assay essentially as described in Example 1.

In another aspect, the multi-specific polypeptide may be able to block binding of CTLA-4 to its ligand with an 1050 value of at least about 16 nM or even lower, such as about 12 nM, about 10 nM or about 5 nM, for example, when the polypeptide is measured in an assay essentially as described in Example 1.

In a related embodiment, a multi-specific polypeptide of the disclosure may be able to block binding of Her2/neu to its ligand with an EC50 value at least comparable or superior to the EC50 value of the immunoglobulin specific for Her2/neu as included in such polypeptide of the disclosure, such as Reference Molecule 1, for example, when said immunoglobulin and the polypeptide are measured in a Her2-positive assay essentially as described in Example 2.

In another aspect, the multi-specific polypeptide may be able to block binding of Her2/neu to its ligand with an EC50 value of at least about 0.8 nM or even lower, such as about 0.6 nM, about 0.3 nM or about 0.1 nM, for example, when the polypeptide is measured in an assay based on T47D cancer cells essentially as described in Example 2.

In an additional aspect, the multi-specific polypeptide may be able to block binding of Her2/neu to its ligand with an EC50 value of at least about 6 nM or even lower, such as about 5 nM, for example, when the polypeptide is measured in an assay based on SKBR3 cells essentially as described in Example 2.

In an another embodiment, a multi-specific polypeptide of the disclosure may be able to block binding of CTLA-4 to its ligand with an EC50 value at least as good as or superior to the EC50 value of a fusion molecule of the lipocalin mutein specific for CTLA-4 as included in such multi-specific polypeptide with the Fc region of an antibody (e.g. IgG1), such as the polypeptide of SEQ ID NO: 100, for example, when said fusion molecule and the multi-specific polypeptide are measured in a CTLA-4-positive assay essentially as described in Example 2.

In an additional aspect, the multi-specific polypeptide may be able to block binding of CTLA-4 to its ligand with an EC50 value of at least about 1.5 nM or even lower, such as about 1.33 nM or about 1.2 nM, for example, when the polypeptide is measured in an assay based on Jurkat cells essentially as described in Example 2.

In a further embodiment, a multi-specific polypeptide of the disclosure may be able to demonstrate ADCC function, when the multi-specific polypeptide is measured in an assay essentially as described in Example 3.

In some still further embodiments, the multi-specific polypeptide may be able to demonstrate comparable level of ADCC function as the immunoglobulin interfering with the Her2/neu receptor as included in such polypeptide, such as Reference Molecule 1, for example, when the polypeptide and the immunoglobulin are measured in a SKBR3-cell based assay essentially described in Example 3.

In some additional embodiments, the multi-specific polypeptide may be able to demonstrate comparable level of ADCC function as the immunoglobulin interfering with the Her2/neu receptor included in such polypeptide, such as Reference Molecule 1, for example, when the polypeptide and the immunoglobulin are measured in a SKBR3-cell based assay in the absence of CHO: CTLA-4 cells essentially described in Example 4 (e.g. see FIG. 5A).

In some other embodiments, the multi-specific polypeptide may be able to demonstrate comparable or superior level of ADCC function compared to a fusion molecule of the lipocalin mutein specific for CTLA-4 as included in such polypeptide with the Fc region of an antibody (e.g. IgG1), such as the polypeptide of SEQ ID NO: 100, for example, when said fusion molecule and the multi-specific polypeptide are measured in a CHO: CTLA-4-cell based assay essentially described in Example 3.

In some particular embodiments, the multi-specific polypeptide may be able to demonstrate bidirectional ADCC function to cells with both Her2 positive and CTLA-4 positive), for example, when said multi-specific polypeptides are measured in an assay essentially described in Example 4 where both SKBR3 cells and CHO: CTLA-4 cells are present. In some other embodiments, the multi-specific polypeptide may be able to demonstrate comparable or superior level of ADCC function compared to the immunoglobulin interfering with the Her2/neu receptor as included in such polypeptide and the lipocalin mutein specific for CTLA-4 as included in such polypeptide, for example, when said multi-specific polypeptide, the immunoglobulin and the lipocalin mutein are measured in an assay essentially described in Example 4 where both SKBR3 cells and CHO: CTLA-4 cells are present.

In still another aspect, the disclosure features the use of one or more multi-specific polypeptides of the disclosure specific for CTLA-4 and Her2/neu or of one or more compositions comprising such polypeptides for simultaneously binding of CTLA-4 and Her2/neu in a subject and/or simultaneously inhibiting the binding of CTLA-4 and Her2/neu to their respective ligands in a subject.

In some embodiments, the multi-specific polypeptides of the disclosure specific for both CTLA-4 and Her2/neu may be capable of simultaneously binding of CTLA-4 and Her2/neu, for example, when said multi-specific polypeptide is measured in an assay essentially described in Example 5. In some further embodiments, the multi-specific polypeptides of the disclosure specific for both CTLA-4 and Her2/neu may be able to demonstrate comparable or superior binding of CTLA-4 and Her2/neu compared to the immunoglobulin interfering with the HER2/neu receptor as included in such polypeptide and the lipocalin mutein specific for CTLA-4 as included in such polypeptide, respectively, for example, when said multi-specific polypeptide, the immunoglobulin and the lipocalin mutein are measured in an assay essentially described in Example 5.

In still another aspect, the present disclosure features a method of simultaneously binding CTLA-4 and Her2/neu in a subject, comprising administering to said subject an effective amount of one or more multi-specific polypeptides of the disclosure specific for CTLA-4 and Her2/neu or of one or more compositions comprising such polypeptides.

In still another aspect, the present disclosure involves a method for simultaneously inhibiting the binding of CTLA-4 and Her2/neu to their respective ligands in a subject, comprising administering to said subject an effective amount of one or more multi-specific polypeptides of the disclosure or of one or more compositions comprising such proteins.

In a specific embodiment, the multi-specific polypeptide of the disclosure comprises the amino acids shown in SEQ ID NOs: 63 and 64, whereby SEQ ID NO: 63 is the light chain of Reference Molecule 1 and SEQ ID NO: 64 is the heavy chain of Reference Molecule 1 fused to CTLA-4 specific lipocalin mutein (SEQ ID NO: 4) via a Serine Glycine linker. In another specific embodiment, the multi-specific polypeptide of the disclosure comprises the amino acids shown in SEQ ID NOs: 63 and 97, whereby SEQ ID NO: 63 is the light chain of Reference Molecule 1 and SEQ ID NO: 97 is the heavy chain of Reference Molecule 1 fused to CTLA-4 specific lipocalin mutein (SEQ ID NO: 95) via a Serine Glycine linker. In an additional embodiment, the multi-specific polypeptide of the disclosure comprises the amino acids shown in SEQ ID NOs: 98 and 99, whereby SEQ ID NO: 98 is the heavy chain of Reference Molecule 1 and SEQ ID NO: 99 is the light chain of Reference Molecule 1 fused to CTLA-4 specific lipocalin mutein (SEQ ID NO: 95) via a Serine Glycine linker. In a further embodiment, the multi-specific polypeptide of the disclosure comprises the amino acids shown in SEQ ID NOs: 97 and 99, whereby SEQ ID NO: 97 is the heavy chain of Reference Molecule 1 fused to CTLA-4 specific lipocalin mutein (SEQ ID NO: 95) via a Serine Glycine linker, and SEQ ID NO: 99 is the light chain of Reference Molecule 1 fused to CTLA-4 specific lipocalin mutein (SEQ ID NO: 95) via a Serine Glycine linker.

D. Uses and Exemplary Examples of Multi-Specific Polypeptide for EGFR Receptor and CTLA-4

In some embodiments, a multi-specific polypeptide of the disclosure binds to CTLA-4 with an affinity by a $K_D$ of about 1 nM or lower, in some cases, about 0.8 or 0.6, 0.5, 0.4, 0.3 nM and below. Thus, the multi-specific polypeptide may be in the picomolar range which is an outstanding property of a binding molecule.

In some embodiments, a multi-specific polypeptide of the disclosure binds to EGFR with an affinity by a $K_D$ of about 1 nM or lower, in some cases, about 0.8 or 0.6, 0.5, and below. Thus, the multi-specific polypeptide may be in the picomolar range which is an outstanding property of a binding molecule.

The binding affinity of a polypeptide to a selected target (e.g. CTLA-4 or EGFR), can be measured (and thereby $K_D$ values of a polypeptide-target complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art.

It is also noted that the complex formation between the respective polypeptide and its target is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective polypeptide and its target) may vary within a certain experimental range, depending on the method and experimental setup that is used for determining the affinity of a particular polypeptide for a given target. This means that there may be a slight deviation in the measured $K_D$ values or a tolerance range depending, for example, on whether the $K_D$ value was determined by surface plasmon resonance (Biacore), by competition ELISA, or by "direct ELISA."

In some further embodiments, the multi-specific polypeptide may have a binding affinity for CTLA-4 as good as or superior to that of the lipocalin mutein specific for CTLA-4 as included in such polypeptide of the disclosure, such as lipocalin muteins selected from the group consisting of SEQ ID NOs: 2-62, 65-84 and 87-96.

In a related embodiment, a multi-specific polypeptide of the disclosure may be able to block binding of EGFR to its ligand with an EC50 value at least comparable or superior to the EC50 value of the immunoglobulin specific for EGFR included in such polypeptide of the disclosure, such as Reference Molecule 2, for example, when said immunoglobulin and the polypeptide are measured in a EGFR-positive assay essentially as described in Example 10.

In another aspect, the multi-specific polypeptide may be able to block binding of EGFR to its ligand with an EC50 value of at least about 0.8 nM or even lower, such as about 0.6 nM, about 0.3 nM or about 0.2 nM, for example, when the polypeptide is measured in an assay based on A431 cancer cells essentially as described in Example 10.

In an another embodiment, a multi-specific polypeptide of the disclosure may be able to block binding of CTLA-4 to its ligand with an EC50 value at least as good as or superior to the EC50 value of a fusion molecule of the lipocalin mutein specific for CTLA-4 as included in such multi-specific polypeptide with the Fc region of an antibody (e.g. IgG1), such as the polypeptide of SEQ ID NO: 100, for example, when said fusion molecule and the multi-specific polypeptide are measured in a CTLA-4-positive assay essentially as described in Example 10.

In an additional aspect, the multi-specific polypeptide may be able to block binding of CTLA-4 to its ligand with an EC50 value of at least about 1.5 nM or even lower, such as about 1.2 nM, for example, when the polypeptide is measured in an assay based on Jurkat cells essentially as described in Example 10.

In a further embodiment, a multi-specific polypeptide of the disclosure may be able to demonstrate ADCC function, when the multi-specific polypeptide is measured in an assay essentially as described in Example 11.

In some still further embodiments, the multi-specific polypeptide may be able to demonstrate comparable level of ADCC function as the immunoglobulin interfering with the EGFR receptor as included in such polypeptide, such as Reference Molecule 2, for example, when the polypeptide and the immunoglobulin are measured in an A431-cell based assay essentially described in Example 11.

In some other embodiments, the multi-specific polypeptide may be able to demonstrate comparable or superior level of ADCC function compared to a fusion molecule of the lipocalin mutein specific for CTLA-4 as included in such polypeptide with the Fc region of an antibody (e.g. IgG1), such as the polypeptide of SEQ ID NO: 100, for example, when said fusion molecule and the multi-specific polypeptide are measured in a CHO: CTLA-4-cell based assay essentially described in Example 11.

In still another aspect, the disclosure features the use of one or more multi-specific polypeptides of the disclosure specific for CTLA-4 and EGFR or of one or more compositions comprising such polypeptides for simultaneously binding of CTLA-4 and EGFR in a subject and/or simultaneously inhibiting the binding of CTLA-4 and EGFR to their respective ligands in a subject.

In some embodiments, the multi-specific polypeptides of the disclosure specific for both CTLA-4 and Her2/neu may be capable of simultaneously binding of CTLA-4 and Her2/neu, for example, when said multi-specific polypeptide is measured in an assay essentially described in Example 12. In some further embodiments, the multi-specific polypeptides of the disclosure specific for both CTLA-4 and EGFR may be able to demonstrate comparable or superior binding of CTLA-4 and EGFR compared to the immunoglobulin interfering with the EGFR receptor as included in such polypeptide and the lipocalin mutein specific for CTLA-4 as included in such polypeptide, respectively, for example, when said multi-specific polypeptide, the immunoglobulin and the lipocalin mutein are measured in an assay essentially described in Example 12.

In still another aspect, the present disclosure features a method of simultaneously binding CTLA-4 and EGFR in a subject, comprising administering to said subject an effective amount of one or more multi-specific polypeptides of the disclosure specific for CTLA-4 and EGFR or of one or more compositions comprising such polypeptides.

In still another aspect, the present disclosure involves a method for simultaneously inhibiting the binding of CTLA-4 and EGFR to their respective ligands in a subject, comprising administering to said subject an effective amount of one or more multi-specific polypeptides of the disclosure or of one or more compositions comprising such proteins.

In a specific embodiment, the multi-specific polypeptide of the disclosure comprises the amino acids shown in SEQ ID NOs: 103 and 105, whereby SEQ ID NO: 103 is the light chain of Reference Molecule 2 and SEQ ID NO: 105 is the heavy chain of Reference Molecule 2 fused to CTLA-4 specific lipocalin mutein (SEQ ID NO: 95) via a Serine Glycine linker.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

VI. EXAMPLES

Example 1

Cell-Based Assay to Assess Inhibition of B7.1 Binding to CTLA-4 by Lipocalin Mutein and Multi-Specific Polypeptide on Human CTLA-4-Transfected CHO Cells FACS competition studies measuring the inhibition of human B7.1 Fc-bio binding to human CTLA-4 expressing CHO cell lines were used to assess the efficacy of a CTLA-4 specific lipocalin mutein (SEQ ID NO: 4) and a multi-specific polypeptide (comprising the amino acids shown in SEQ ID NOs: 63 and 64) of the lipocalin mutein and Reference Molecule 1. Different concentrations of lipocalin mutein or multi-specific polypeptide were mixed with recombinant biotinylated human B7.1 (Ancell) at 20 nM final concentration and added to human CTLA-4 transfected CHO-K1 cells, which were generated according to the description in example 16 of PCT publication WO 2006/056464. Human CTLA-4 expressing Cells were pre-incubated in ice cold PBS (2% FCS) at a density of $2\times10^5$ for 60 minutes prior to addition of 20 nM B7.1 Fc-bio and varying concentrations of the CTLA-4 specific lipocalin mutein or the multi-specific polypeptide. Cells were incubated on ice for 2 hours. Cells were washed twice in ice cold PBS prior to incubation with streptavidin-PE (on ice for 30 min.). Cells were washed twice in ice cold PBS, re-suspended in PBS and analyzed using a Guava Flow cytometer. Typically, 10,000 events were recorded, a gate was set around the viable cells, and results are expressed as geometric mean of the fluorescence intensity (MFI).

In the assay, the lipocalin mutein of SEQ ID NO: 4 displayed an 1050 value of 23 nM while the multi-specific polypeptide exhibited an 1050 value of 16 nM (see FIG. 2).

Example 2

Cell-Based Assay to Assess Binding Affinity of Reference Molecule 1, Fc-Fusion Molecule and Multi-Specific Polypeptide FACS studies measuring the binding of Reference Molecule 1 and a multi-specific polypeptide (comprising the amino acids shown in SEQ ID NOs: 63 and 64) to Her2-positive T47D cancer cells were performed. T47D cancer cells were pre-incubated in ice cold PBS (2% FCS) at a density of $2\times10^5$ for 60 minutes prior to addition of varying concentrations of Reference Molecule 1 or multi-specific polypeptide. Cells were incubated on ice for 2 hours. Cells were washed twice in ice cold PBS prior to incubation with anti-human IgG PE secondary antibody (on ice for 30 minutes). Cells were washed twice in ice cold PBS, re-suspended in PBS and analyzed using a Guava Flow cytometer. Typically, 10,000 events were recorded, a gate was set around the viable cells, and results are expressed as geometric mean of the fluorescence intensity (MFI).

In the assay, Reference Molecule 1 displayed an EC50 value of 1.7 nM while the multi-specific polypeptide exhibited an EC50 value of 0.8 nM (see FIG. 3A).

Further FACS experiments were carried out to assess binding of multi-specific polypeptides (comprising the amino acids shown in SEQ ID NOs: (63 and 97), SEQ ID NOs: (98 and 99) or SEQ ID NOs: (97 and 99), respectively) to Her2-positive SKBR3 cells under conditions as outlined above (with the exception that cells were seeded at a density of $1\times10^5$ (expressing around 1000 times more Her2 than the T47D cells), and the anti-human IgG secondary antibody was labelled with Alexa 488 instead of PE). In the assay, all multi-specific polypeptides displayed similar binding to Her2 when compared to Reference Molecule 1 (see FIG. 3B) as summarized in Table 1 below.

TABLE 1

|  | Reference Molecule 1 | SEQ ID NOs: 63 and 97 | SEQ ID NOs: 98 and 99 | SEQ ID NOs: 97 and 99 |
| --- | --- | --- | --- | --- |
| EC50 [nM] | 4.478 | 4.988 | 5.886 | 5.847 |

FACS studies measuring the binding of said multi-specific polypeptide molecules (comprising the amino acids shown in SEQ ID NOs: (63 and 97), SEQ ID NOs: (98 and 99) or SEQ ID NOs: (97 and 99), respectively) and a positive control molecule—a polypeptide of SEQ ID NO: 100 (comprising a fusion of human IgG1 Fc fused to lipocalin mutein SEQ ID: 95)—to CTLA-4 positive Jurkat cells were performed. Following overnight incubation with Doxycyclin, CTLA-4 positive Jurkat cells were pre-incubated in ice cold PBS (2% FCS) at a density of $1\times10^5$ for 60 minutes prior to addition of varying concentrations of test article. Cells were incubated on ice for 1 hour. Cells were washed twice in ice cold PBS prior to incubation with rabbit anti-lipocalin antibody (on ice for 30 minutes). Cells were washed twice in ice cold PBS, re-suspended in PBS and incubated with goat anti-rabbit-PE (on ice for 30 minutes). Cells were washed twice in ice cold PBS, re-suspended in PBS and analyzed using a Guava Flow cytometer. Typically, 10,000 events were recorded, a gate was set around the viable cells, and results are expressed as geometric mean of the fluorescence intensity (MFI).

In the assay, all multi-specific polypeptides displayed similar binding to CTLA-4 when compared to the positive control polypeptide of SEQ ID NO: 100 (see FIG. 3C) as summarized in Table 2 below.

TABLE 2

|  | SEQ ID NO: 100 | SEQ ID NOs: 63 and 97 | SEQ ID NOs: 98 and 99 | SEQ ID NOs: 97 and 99 |
| --- | --- | --- | --- | --- |
| EC50 [nM] | 1.56 | 1.33 | 1.495 | 1.182 |

Example 3

Cell-Based Assay to Assess ADCC Function of Reference Molecule 1, Fc-Fusion Molecule and Multi-Specific Polypeptides Human PBMC were isolated from whole blood (consenting healthy volunteer donors) by centrifugation through a Biocoll (Biochrom, Berlin, Germany) density gradient (1.077 g/ml). The breast cancer cell line SKBR3 (HTB-30 obtained from American Tissue Culture Collection/ATCC), which is Her2 positive, was maintained in McCoy's 5A (Gibco) supplemented with 10% FBS (Gibco) at 37° C. in a 5% CO2 atmosphere. The human CTLA-4 expressing CHO were maintained in DMEM A (Gibco) supplemented with 10% FBS (Gibco) and with Zeocin 200 µg/ml (In Vitrogen) at 37° C. in a 5% CO2.

A fluorometric cytotoxicity assay with calcein-acetoxymethyl (Calcein AM) was used to measure the lysis of drug-mediated ADCC function.

The SKBR3 or chines hamster ovary (CHO): CTLA-4 target cells were plated on 96 well culture plates and allowed to adhere overnight. Cells were then labeled with Calcein AM (10 µM, from Invitrogen) for 1 hour and washed. Labelled target cells were pre-incubated for 30 minutes with test article (2, 10, 200 nM) or isotype control antibodies (IgG1 or IgG1 Fc) before adding PBMC at different effector: target (E:T) ratios (e.g. 25:1, 12.5:1 and 6:1).

After 4 hr incubation at 37° C., the release of Calcein into culture medium was measured by a Tecan M1000 instrument at a wavelength of 495/515 nM. The percentages of specific lysis were calculated according to the formula: (experimental release−spontaneous release)/(maximal release−spontaneous release)×100, where experimental release represents the mean fluorescence for target cells incubated in the presence of effector cells and of test article, and spontaneous release represents the mean fluorescence for target cells incubated without effector cells, and maximal release represents the mean fluorescence for target cells incubated with Triton X-100. Triplicate wells were set up for each E:T ratio. Results were expressed at mean±SD of triplicate wells at each E:T ratio.

A target dependent killing of SKBR3 cells could be observed for both Reference Molecule 1 and a multi-specific polypeptide (comprising the amino acids shown in SEQ ID NOs: 63 and 64), as measured by Calcein AM release assay. Both molecules showed comparable levels of specific cell lysis on SKBR3 cells at equal concentrations (approximately 93% and 90%, respectively, see FIG. 4A). As shown in FIG. 4A, the percentage of specific lysis obtained with Reference Molecule 1 and multi-specific polypeptide was approximately 90% when E:T ratio of 1:50 was used in this assay. Isotype control antibodies did not lead to specific or significant lysis of SKBR3 cells. The test articles did not lead to significant lysis of target negative cells (data not shown).

A target dependent killing of CHO: CTLA4 cells was observed for the positive control polypeptide (SEQ ID NO: 100) and for the multi-specific polypeptides (comprising the amino acids shown in SEQ ID NOs: (63 and 64); (97 and 63), (98 and 99), or (97 and 99), respectively), as measured by Calcein AM release assay. The test articles showed comparable levels of specific cell lysis on CHO: CTLA-4 cells at equal concentrations approximately ranging from 45% to 65% when E:T ratio of 25:1 was used in this assay, see FIG. 4B). Isotype control antibodies did not lead to specific or significant lysis of CHO: CTLA-4 cells. The test articles did not lead to significant lysis of target negative cells (data not shown).

Example 4

ADCC Function and Bidirectional Killing (ADCC) of Multi-Specific Polypeptide in Co-Culture Model A fluorometric cytotoxicity assay with calcein-acetoxymethyl (Calcein AM) was used to measure the lysis of drug-mediated ADCC function.

The CHO: CTLA-4 cells were plated on 96 well culture plates and allowed to adhere overnight.

To investigate killing of Her2 positive cells by multi-specific polypeptides, SKBR3 cells were labeled with Calcein AM (10 µM, from Invitrogen) for 1 hour and washed. Labelled target cells were added to wells pre-coated or not with CHO: CTLA 4 wells and pre-incubated for 30 minutes with test article (2 or 10 nM) before adding PBMC at different E:T ratios (e.g. 25:1, 12.5:1 and 6:1).

To investigate killing of CTLA-4 positive cells by multi-specific polypeptides, CHO: CTLA-4 cells were then labeled with Calcein AM (10 µM, from Invitrogen) for 1 hour and washed. Labelled target cells were pre-incubated for 30 minutes with test article (2 or 10 nM) or isotype control antibodies (IgG1 or IgG1 Fc) in presence or absence of SKBR3 cells before adding PBMC at different E:T ratios (e.g. 25:1 and 12.5:1).

After 4 hr incubation at 37° C., the release of Calcein into culture medium was measured by a Tecan M1000 instrument at a wavelength of 495/515 nM. The percentages of specific lysis were calculated according to the formula: (experimental release−spontaneous release)/(maximal release−spontaneous release)×100, where experimental release represents the mean fluorescence for target cells incubated in the presence of effector cells and test articles, and spontaneous release represents the mean fluorescence for target cells incubated with effector cells, and maximal release represents the mean fluorescence for target cells incubated with Triton X-100. Triplicate wells were set up for each E:T ratio. Results were expressed at mean±SD of triplicate wells at each E:T ratio.

In this setting, a target dependent killing of SKBR3 could be observed for both Reference Molecule 1 and multi-specific polypeptides (comprising the amino acids shown in SEQ ID NOs: (63 and 64); (97 and 63), (98 and 99), or (97 and 99), respectively) in absence (FIG. 5A) or in presence of CHO: CTLA-4 cells (FIG. 5B). All molecules showed comparable levels of specific cell lysis on SKBR3 cells at equal concentrations when E:T ratio of 1:6 (FIG. 5A) or 12.5:1 (FIG. 5B) was used for this assay (approximately 55%, in FIG. 5A and approximately ranging from 55% to 65% in FIG. 5B). Presence of CHO: CTLA-4 cells had no impact on specific lysis.

A target dependent killing of CHO: CTLA-4 in presence of SKBR3 cells could be observed for the multi-specific polypeptides (comprising the amino acids shown in SEQ ID NOs: (63 and 64), (97 and 63), (98 and 99), or (97 and 99), respectively). The test molecules showed similar levels of specific cell lysis on CHO: CTLA-4 cells at 10 nM (approximately ranging from 45% to 65%, see FIG. 5C) when E:T ratio of 25:1 was used. A slight decrease was observed with multi-specific polypeptide of SEQ ID NOs: 97 and 63 at 2 nM (approximately ranging from 20% to 55% for all test molecules, see FIG. 5C). The specific lysis in presence of SKBR3 cells was as effective as in absence of SKBR3 cells (compared to FIG. 4B). Isotype control antibodies did not lead to specific or significant lysis of CHO: CTLA 4 cells. The test articles did not lead to significant lysis of target negative cells (data not shown).

Example 5

Affinity of Reference Molecule 1, Lipocalin Mutein and Multi-Specific Polypeptide to Human Her2 and CTLA-4

Binding affinities of multi-specific polypeptides (comprising the amino acids shown in SEQ ID NOs: (63 and 97), (98 and 99) or (97 and 99), respectively), Reference Molecule 1, lipocalin mutein of SEQ ID NO: 95 and positive control polypeptide of SEQ ID NO: 100 to the respective targets, human Her2 (Sino Biological, 10004-H08H) and human CTLA-4 (Sino Biological, 11159-H08H), were determined by Surface Plasmon Resonance (SPR) using a Biacore T200 instrument (GE Healthcare). In the SPR affinity assay, biotinylated ligand (multi-specific polypeptides, Reference Molecule 1, lipocalin mutein or polypeptide) was captured on a sensor chip CAP using the Biotin CAPture Kit (GE Healthcare): sensor Chip CAP is pre-immobilized with a ssDNA oligo. Undiluted Biotin CAPture Reagent (streptavidin conjugated with the complementary ss-DNA oligo)

was applied at a flow rate of 2 μL/min for 300 s. Subsequently, 10 μg/mL of biotinylated ligand was applied for 300 s at a flow rate of 5 μL/min. Multi-specific polypeptides, Reference Molecule 1, lipocalin mutein of SEQ ID NO: 95 and polypeptide of SEQ ID NO: 100 were biotinylated by incubation with EZ-LINK™ NHS-PEG4-Biotin (5-fold molar excess (Thermo Scientific)) during two hours at room temperature. The excess of non-reacted biotin reagent was removed by loading the reaction mixture onto a Spin Desalting Plate (Thermo Scientific). The reference channel was loaded with Biotin CAPture Reagent only.

To determine the affinity, three dilutions of hHer2 (100, 33 and 11 nM) or of hCTLA-4 with (100, 25 and 6 nM) were prepared in running buffer (10 mM HEPES, 150 mM NaCl, 0.05% v/v Surfactant P20, 3 mM EDTA, pH 7.4 (GE Healthcare)) and applied to the prepared chip surface. Applying a flow rate of 30 μL/min, the sample contact time was 180 s and dissociation time was 4500 s for hHer2 or 900 s for hCTLA-4. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Prior to the protein measurements three regeneration cycles were performed for conditioning purposes. Data were evaluated with Biacore T200 Evaluation software (V 1.0). Double referencing was used and the 1:1 Binding model was used to fit the raw data.

The results are summarized in Table 3. The data shows that the multi-specific polypeptides bind hHer2 with sub-nanomolar affinity comparable to Reference Molecule 1. Apparent binding affinities/avidities as determined using dimeric hCTLA-4 as analyte were in the range of 2-7 nM. Apparent affinities were increased three- to fourfold for multi-specific polypeptides when compared to lipocalin mutein of SEQ ID NO: 95, mainly due to an increased On-Rate in connection with the bivalency of the multi-specific polypeptides.

TABLE 3

|  | hHer2 $K_D$ [nM] | hCTLA-4 (dimeric) Avidity [nM] |
|---|---|---|
| SEQ ID NOs: 97 and 63 | 0.16 | 1.8 |
| SEQ ID NOs: 98 and 99 | 0.16 | 2.4 |
| SEQ ID NOs: 97 and 99 | 0.15 | 2.0 |
| Reference Molecule 1 | 0.23 | n.a. |
| SEQ ID NO: 100 | n.a. | 2.3 |
| SEQ ID NO: 95 | n.a. | 7.2 |

Example 6

Affinity of Reference Molecule 1 and Multi-Specific Polypeptides to Fc-Gamma Receptors hFcγ RI/CD64 and hFcγ RIIIA/CD16a To measure the binding affinities of Reference Molecule 1 and multi-specific polypeptides (comprising the amino acids shown in SEQ ID NOs: (63 and 64), (97 and 63), (98 and 99) or (97 and 99), respectively) to Fc-gamma receptors hFcγ RI/CD64 (R&D Systems) and hFcγ RIIIA/CD16a (R&D Systems), a Surface Plasmon Resonance (SPR) based assay as described in Example 5 was employed. Ligand (Reference Molecule 1 and mult-specific polypeptides) biotinylation, reagent and ligand capture and chip surface regeneration were performed as described in Example 5. Assay temperature and running buffer were identical to Example 5. In the SPR affinity assay, biotinylated Reference Molecule 1 or multi-specific polypeptide was captured on a sensor chip CAP using the Biotin CAPture Kit (GE Healthcare): Sensor Chip CAP is pre-immobilized with a ssDNA oligo. Undiluted Biotin CAPture Reagent (streptavidin conjugated with the complementary ss-DNA oligo) was applied at a flow rate of 2 μL/min for 300 s. Subsequently, 10 μg/mL of biotinylated multi-specific polypeptide or Reference Molecule 1 was applied for 300 s at a flow rate of 5 μL/min. Reference Molecule 1 and the multi-specific polypeptide were biotinylated by incubating with EZ-LINK™ NHS-PEG4-Biotin (5-fold molar excess (Thermo Scientific)) during two hours at room temperature. The excess of non-reacted biotin reagent was removed by loading the reaction mixture onto a Spin Desalting Plate (Thermo Scientific). The reference channel was loaded with Biotin CAPture Reagent only.

To determine the affinity, three dilutions of hFcγ RI/CD64 (at 40, 8 and 1.6 or at 100, 25 and 6 nM) or four to five dilutions of hFcγ RIIIA/CD16a (at 200, 40, 8 and 1.6 nM or at 1000, 333, 111, 37 and 12 nM) were prepared in running buffer (10 mM HEPES, 150 mM NaCl, 0.05% v/v Surfactant P20, 3 mM EDTA, pH 7.4 (GE Healthcare)) and applied to the chip surface. Applying a flow rate of 30 μL/min, the sample contact time was 180 s and dissociation time was 1800/2700 s for hFcγ RI/CD64 or 300 s hFcγ RIIIA/CD16a. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Prior to the protein measurements three regeneration cycles were performed for conditioning purposes. Data were evaluated with Biacore T200 Evaluation software (V 1.0). Double referencing was used. For hFcγ RI/CD64 the 1:1 Binding model was used to fit the raw data. For hFcγ RIIIA/CD16a the Steady State Affinity model was used to fit the raw data.

The resulting binding affinities for Reference Molecule 1 and multi-specific polypeptide of SEQ ID NOs: 63 and 64 are summarized in Table 4. The data shows that the multi-specific polypeptide bound hFcγ RI/CD64 with an association rate constant of $k_a$=7.5×105 M$^{-1}$s$^{-1}$ and a dissociation rate constant of $k_d$=1.1×10$^{-4}$ s$^{-1}$, resulting in a dissociation constant of $K_D$=139 pM and bound hFcγ RIIIA/CD16a with a dissociation constant of $K_D$=0.2 μM fitted as steady state affinity. Reference Molecule 1 bound hFcγ RI/CD64 with a dissociation constant of $K_D$=135 pM, derived from the following rate constants: $k_a$=8.9×10$^5$ M$^{-1}$s$^{-1}$, $k_d$=1.2×10$^{-4}$ s$^{-1}$, and bound hFcγ RIIIA/CD16a with a steady state dissociation constant of $K_D$=0.3 μM.

TABLE 4

|  | hFcγ RIIIA/CD16a $K_D$ [μM] (steady state affinity fit) | hFcγ RI/CD64 | | |
|---|---|---|---|---|
|  |  | $k_a$ [M$^{-1}$s$^{-1}$] | $k_d$ [s$^{-1}$] | $K_D$ [pM] ($k_d/k_a$) |
| Multi-specific Polypeptide (SEQ ID NOs: 63 and 64) | 0.2 | 7.5 × 10$^5$ | 1.1 × 10$^{-4}$ | 139 |
| Reference Molecule 1 | 0.3 | 8.9 × 10$^5$ | 1.2 × 10$^{-4}$ | 135 |

Table 5 summarizes the determined binding affinities of multi-specific polypeptides of SEQ ID NOs: (97 and 63), (98 and 99) or (97 and 99), respectively, to hFcγRI/CD64 and hFcγRIII/CD16a in comparison to Reference Molecule 1. Multi-specific polypeptides and Reference Molecule 1 bind hFcγRI/CD64 with comparable affinities in the range of 0.1 nM. The determined steady state binding affinities for multi-specific polypeptides and Reference Molecule 1 to hFcγRIII/CD16a are as well comparable and in a range of 0.3-0.4 µM.

TABLE 5

|  | hFcγ RI/CD64 KD [nM] | hFcγ RIIIA/CD16a KD [µM] |
|---|---|---|
| Reference Molecule 1 | 0.10 | 0.29 |
| Multi-specific Polypeptide (SEQ ID NOs: 97 and 63) | 0.08 | 0.31 |
| Multi-specific Polypeptide (SEQ ID NOs: 98 and 99) | 0.09 | 0.41 |
| Multi-specific Polypeptide (SEQ ID NOs: 97 and 99) | 0.10 | 0.37 |

Example 7

Lipocalin Muteins Blocking Binding of B7.1 on Human CTLA-4-Transfected CHO Cells in FACS Different concentrations of lipocalin muteins (SEQ ID NO: 4, SEQ ID NO: 61, SEQ ID NO: 62, SEQ ID NO: 65, SEQ ID NO: 66, SEQ ID NO: 94 and SEQ ID NO: 95) as well as wild type Lcn2 (SEQ ID NO: 101) and isotype control antibodies (IgG1 or IgG1 Fc) were mixed with recombinant biotinylated human CD80/B7.1 (Ancell) at 20 nM final concentration and added to 100 000 of the CTLA-4 transfected CHO-K1 cells which were generated according to the description in Example 16 of PCT/EP 2005/012640. Samples were incubated at 4° C. for 1 h, washed twice in PBS containing 2% FCS, and detection of bound CD80/B7.1 was accomplished by incubation with streptavidin-phycoerythrin for 30 min at 4° C. Mean fluorescence intensities were determined by flow cytometry and fitted to a sigmoidal dose response model using Prism (GraphPad) as depicted in FIG. 6 to determine EC50 values for lipocalin muteins which are summarized in Table 6. Wild type Lcn2 (SEQ ID NO: 101) or isotype control antibodies did not lead to measurable inhibition of CD80/B7.1 binding to the CTLA-4 expressing CHO cells (data not shown).

TABLE 6

| lipocalin mutein | EC50 [nM] |
|---|---|
| SEQ ID NO: 62 | 6 |
| SEQ ID NO: 61 | 9.3 |
| SEQ ID NO: 65 | 7.8 |
| SEQ ID NO: 66 | 7.4 |
| SEQ ID NO: 94 | 13.4 |
| SEQ ID NO: 95 | 9.7 |
| SEQ ID NO: 4 | 7.6 |

Example 8

Affinity of Lipocalin Muteins to hCTLA-4

Surface Plasmon Resonance (SPR) using a Biacore T200 instrument (GE Healthcare) was performed to determine binding affinities of lipocalin muteins (SEQ ID NO: 4, SEQ ID NO: 61, SEQ ID NO: 62, SEQ ID NO: 65, SEQ ID NO: 66, SEQ ID NO: 94 and SEQ ID NO: 95) to human CTLA-4. Anti-human IgG-Fc antibody from human antibody capture kit (GE Healthcare, BR-1008-39) was immobilized on a CM5 sensor chip using standard amine coupling chemistry and the immobilization buffer included the kit (10 mM sodium acetate pH 5.0), resulting in a ligand density of about 7000 resonance units (RU). The reference channel was treated accordingly.

Human CTLA-4-Fc (Chimerigen, CHI-HF-210A4-M001) at a concentration of 5 µg/mL was captured on this surface for 180 s at a flow rate of 10 µl/min in HBS-EP+ buffer (GE Healthcare; BR100669; 1:10 diluted). No human CTLA-4-Fc was applied to the reference channel. Subsequently, the lipocalin muteins were applied in an appropriate dilution series in HBS-EP+ buffer at a flow rate of 30 µl/min. Regeneration of the derivatized chip surface was achieved by a combination of first basic (2.5 mM NaOH) and then acidic (10 mM glycine, pH 1.5) buffer, each for 8 and 16 s, respectively.

Prior to the protein measurements three regeneration cycles were performed for conditioning purposes. Data were evaluated with Biacore T200 Evaluation software (V 1.0). Double referencing was used and the 1:1 Binding model was used to fit the raw data.

Table 7 shows the fitted association and dissociation rate constants ka and kd and the resulting affinities. All assayed lipocalin muteins bind captured human CTLA-4-Fc with affinities in the range of 0.4-2 nM.

TABLE 7

| lipocalin mutein | $k_a$ [$M^{-1} * s^{-1}$] | $k_d$ [$s^{-1}$] | $K_D$ [nM] |
|---|---|---|---|
| SEQ ID NO: 4 | 6.4E+05 | 2.2E−04 | 0.35 |
| SEQ ID NO: 62 | 7.5E+05 | 2.7E−04 | 0.36 |
| SEQ ID NO: 65 | 7.1E+05 | 4.4E−04 | 0.62 |
| SEQ ID NO: 61 | 7.7E+05 | 7.2E−04 | 0.94 |
| SEQ ID NO: 66 | 7.5E+05 | 1.3E−03 | 1.8 |
| SEQ ID NO: 94 | 3.4E+05 | 6.1E−04 | 1.8 |
| SEQ ID NO: 95 | 8.6E+05 | 1.2E−03 | 1.4 |

Example 9

Characterization of Thermal Stability of Lipocalin Muteins and Multi-Specific Polypeptides To determine melting temperatures as a general indicator for overall stability, lipocalin muteins (SEQ ID NO: 4, SEQ ID NO: 61, SEQ ID NO: 62, SEQ ID NO: 65, SEQ ID NO: 66, SEQ ID NO: 94 and SEQ ID NO: 95), multi-specific polypeptides (comprising the amino acids shown in SEQ ID NOs: (97 and 63), (98 and 99) or (97 and 99), respectively), Reference Molecule 1 and polypeptide of SEQ ID NO: 100 at a protein concentration of 1 mg/ml in PBS (Gibco) were scanned (25-100° C.) at 1 K/min using a capillary nanoDSC instrument (CSC 6300, TA Instruments). Melting temperatures (Tm) were calculated from the transitions observed in the scans using the integrated Nano Analyze software.

Table 8 summarizes Tms fitted based on the detected transitions and onset of melting observed in the scans.

TABLE 8

| Sample | Tm [° C.] | Onset of melting [° C.] |
|---|---|---|
| SEQ ID NO: 4 | 55 | 45 |
| SEQ ID NO: 65 | 69 | 61 |

TABLE 8-continued

| Sample | Tm [° C.] | Onset of melting [° C.] |
|---|---|---|
| SEQ ID NO: 66 | 65 | 58 |
| SEQ ID NO: 94 | 67 | 61 |
| SEQ ID NO: 95 | 66 | 58 |
| SEQ ID NO: 62 | 62; 70 | 52 |
| SEQ ID NO: 61 | 57 | 50 |
| SEQ ID NOs: 63 & 97 | 69; 80 | 63 |
| SEQ ID NOs: 98 & 99 | 68; 80 | 56 |
| SEQ ID NOs: 100 | 68; 78; 83 | 59 |
| SEQ ID NOs: 97 & 99 | 67; 80; 86 | 59 |
| Reference Molecule 1 | 71; 81 | 65 |

Example 10

Cell-Based Assay to Assess Binding Affinity of Reference Molecule 2, Fc-Fusion Molecule and Multi-Specific Polypeptide FACS studies measuring the binding of Reference Molecule 2 (comprising the amino acids shown in SEQ ID NOs: 103 and 104) and a multi-specific polypeptide (comprising the amino acids shown in SEQ ID NOs: 103 and 105) to EGFR positive A431 cancer cells were performed. A431 cancer cells were pre-incubated in ice cold PBS (2% FCS) at a density of $1 \times 10^5$ for 60 minutes prior to addition of varying concentrations of Reference Molecule 2 or multi-specific polypeptide. Cells were incubated on ice for 1 hr. Cells were washed twice in ice cold PBS prior to incubation with anti-human IgG secondary antibody was labelled with Alexa 488 (on ice for 30 minutes). Cells were washed twice in ice cold PBS, re-suspended in PBS and analyzed using a Guava Flow cytometer. Typically, 10,000 events were recorded, a gate was set around the viable cells, and results are expressed as geometric mean of the fluorescence intensity (AU Geomean).

In the assay, Reference Molecule 2 displayed an EC50 value of 0.6 nM while the multi-specific polypeptide exhibited an EC50 value of 0.2 nM (see FIG. 7A).

Further FACS experiments were carried out to assess binding of the multi-specific polypeptide molecule and a positive control molecule—a polypeptide of SEQ ID NO: 100 (comprising a fusion of human IgG1 Fc fused to lipocalin mutein SEQ ID: 95) to CTLA-4 positive Jurkat cells, using parameters described in Example 2.

In the assay, the multi-specific polypeptide displayed similar binding to CTLA-4 (EC50: 1.2 nM) when compared to the positive control polypeptide of SEQ ID NO: 100 (EC50: 1.1 nM) (see FIG. 7B).

Example 11

ADCC Function and Bidirectional Killing (ADCC) of Multi-Specific Polypeptide in Co-Culture Model Human PBMC and the human CTLA-4 expressing CHO were obtained and cultured as described in Example 3. The human epidermoid carcinoma A431 (DSMZ) which is EGFR positive was maintained in DMEM A (Gibco) supplemented with 10% FBS (Gibco) at 37° C. in a 5% CO2.

A fluorimetric cytotoxicity assay with calcein-acetoxymethyl (Calcein AM) was used to measure the lysis of drug-mediated ADCC function.

The CHO: CTLA-4 cells were plated on 96 well culture plates and allowed to adhere overnight.

To investigate killing of EGFR positive cells by multi-specific polypeptide, A431 cells were labeled with Calcein AM (10 μM, from Invitrogen) for 1 hour and washed. Labelled target cells were added to wells pre-coated or not with CHO: CTLA-4 wells and pre-incubated for 30 minutes with test article (0.5 or 10 nM) before adding PBMC at different E:T ratios (e.g. 25:1, 12.5:1 and 6:1).

To investigate killing of CTLA-4 positive cells by multi-specific polypeptides, CHO: CTLA-4 cells were then labeled with Calcein AM (10 μM, from Invitrogen) for 1 hour and washed. Labelled target cells were pre-incubated for 30 minutes with test article (2 or 10 nM) or isotype control antibodies in presence or absence of A431 cells before adding PBMC at different E:T ratios (e.g. 25:1 and 12.5:1).

After 4 hr incubation at 37° C., the release of Calcein into culture medium was measured by a Tecan M1000 instrument at a wavelength of 495/515 nm. The percentages of specific lysis were calculated according to the formula: (experimental release–spontaneous release)/(maximal release–spontaneous release)×100, where experimental release represents the mean fluorescence for target cells incubated in the presence of effector cells and test articles, and spontaneous release represents the mean fluorescence for target cells incubated with effector cells, and maximal release represents the mean fluorescence for target cells incubated with Triton X-100. Triplicate wells were set up for each E:T ratio. Results were expressed at mean±SD of triplicate wells at each E:T ratio.

In this setting, a target dependent killing of A431 could be observed for both Reference Molecule 2 and multi-specific polypeptide (comprising the amino acids shown in SEQ ID NOs (103 and 105) in presence or in absence of CHO: CTLA-4 cells (FIG. 8A). All molecules showed comparable levels of specific cell lysis on A431 cells at equal concentrations when E:T ratio of 1:6 or 12.5:1 was used for this assay (approximately ranging from 55% to 65% in FIG. 8A). Presence of CHO: CTLA-4 cells had no impact on specific lysis.

A target dependent killing of CHO: CTLA-4 in presence or in absence of A431 cells could be observed for the multi-specific polypeptide (comprising the amino acids shown in SEQ ID NOs 103 and 105). The test molecules showed similar levels of specific cell lysis on CHO: CTLA-4 cells at 10 nM or 0.5 nM (approximately ranging from 45% to 58%, see FIG. 8B) when E:T ratio of 25:1 was used. The specific lysis in presence of A431 cells was as effective as in absence of A431 cells. Isotype control antibodies did not lead to specific or significant lysis of CHO: CTLA 4 cells. The test articles did not lead to significant lysis of target negative cells (data not shown).

Example 12

Affinity of Reference Molecule 2, Lipocalin Mutein and Multi-Specific Polypeptide to Human EGFR and CTLA-4

Binding affinities of multi-specific polypeptide (comprising the amino acids shown in SEQ ID NOs: 103 and 105), Reference Molecule 2, lipocalin mutein of SEQ ID NO: 95 and positive control polypeptide of SEQ ID NO: 100 to the respective targets, human EGFR (Sino Biological 1001-

H08B) and human CTLA-4 (Sino Biological, 11159-H08H), were determined by Surface Plasmon Resonance as described in Example 5.

To determine the affinity, three dilutions of hEGFR and of hCTLA-4 with (100, 25 and 6 nM) were prepared in running buffer (10 mM HEPES, 150 mM NaCl, 0.05% v/v Surfactant P20, 3 mM EDTA, pH 7.4 (GE Healthcare)) and applied as described in example 5. Dissociation time was 900 s for hCTLA-4 and hEGFR.

The results are summarized in Table 9. The data shows that the multi-specific polypeptide (comprising the amino acids shown in SEQ ID NOs: 103 and 105) binds hEGFR with sub-nanomolar affinity comparable to Reference Molecule 2. Apparent binding affinities/avidities as determined using dimeric hCTLA-4 as analyte were in the range of 2-7 nM. The apparent affinity of the multi-specific polypeptide was increased fourfold when compared to lipocalin mutein of SEQ ID NO: 95, mainly due to an increased On-Rate in connection with the bivalency of the multi-specific polypeptides.

TABLE 9

| | hEGFR $K_D$ [nM] | hCTLA-4 (dimeric) Avidity [nM] |
|---|---|---|
| Reference Molecule 2 | 0.54 | n.a. |
| SEQ ID NOs: 103 and 105 | 0.45 | 1.7 |
| SEQ ID NO: 95 | n.a. | 7.2 |

Example 13

Affinity of Reference Molecule 2 and Multi-Specific Polypeptide to Fc-Gamma Receptors hFcγ RI/CD64 and hFcγ RIIIA/CD16a Binding affinities of Reference Molecule 2 and multi-specific polypeptide (comprising the amino acids shown in SEQ ID NOs: 103 and 105) to Fc-gamma receptors hFcγRI/CD64 and hFcγRIIIA/CD16a was performed as described in Example 6.

The resulting binding affinities for Reference Molecule 2 and multi-specific polypeptide (comprised of SEQ ID NOs: 103 and 105) are summarized in Table 10. The data shows that the Reference Molecule 2 bound hFcγ RI/CD64 with an association rate constant of $k_a=1.8\times10^6$ $M^{-1}s^{-1}$ and a dissociation rate constant of $k_d=1.4\times10^{-4}$ $s^{-1}$, resulting in a dissociation constant of $K_D=78$ pM and bound hFcγ RIIIA/CD16a fitted with a dissociation constant of $K_D=172$ nM fitted as steady state affinity. The multi-specific polypeptide bound hFcγRI/CD64 with a dissociation constant of $K_D=66$ pM, derived from the following rate constants: $k_a=2.4\times10^5$ $M^{-1}s^{-1}$, $k_d=1.6\times10^{-4}$ $s^{-1}$, and bound hFcγ RIIIA/CD16a with a steady state dissociation constant of $K_D=181$ nM.

TABLE 10

| | hFcγ RIIIA/CD16a $K_D$ [μM] (steady state affinity fit) | hFcγ RI/CD64 | | |
|---|---|---|---|---|
| | | $k_a$ [$M^{-1}s^{-1}$] | $k_d$ [$s^{-1}$] | $K_D$ [pM] ($k_d/k_a$) |
| SEQ ID NOs: 103 and 105 | 0.2 | 2.4 × 10$^6$ | 1.6 × 10$^{-4}$ | 66 |
| Reference Molecule 2 | 0.2 | 1.8 × 10$^6$ | 1.4 × 10$^{-4}$ | 78 |

Example 14

Characterization of Thermal Stability of Multi-Specific Polypeptide

Determination of melting temperature of the multi-specific polypeptide (comprising the amino acids shown in SEQ ID NOs: 103 and 105), lipocalin mutein of SEQ ID NO: 95 and Reference Molecule 2 was performed as described in Example 9. For the multi-specific polypeptide, an additional transition was found at 68° C. which is likely to correspond to the lipocalin mutein fused therein.

Table 11 shows Tms fitted based on the detected transitions and onset of melting observed in the scans from a representative experiment.

TABLE 11

| Sample | Tm [° C.] | Onset of melting [° C.] |
|---|---|---|
| Reference Molecule 2 | 72; 74, 84 | 65 |
| SEQ ID NO: 95 | 66 | 58 |
| SEQ ID NOs: 103 and 105 | 68; 71; 74; 84 | 62 |

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

The invention claimed is:

1. A fusion protein comprising at least two binding domains, wherein a first binding domain comprises a full-length immunoglobulin, wherein a second binding domain comprises a mutein of human neutrophil gelatinase-associated lipocalin (hNGAL)
   wherein said first binding domain has binding specificity for Her2/neu, and said second binding domain has binding specificity for CTLA-4;
   wherein the fusion protein comprises said second binding domain fused to C-terminus of each heavy chain and each light chain of the first binding domain; and
   wherein the fusion protein comprises the amino acid sequences of SEQ ID NOs: 97 and 99.

2. The fusion protein of claim 1, wherein the fusion protein activates CTLA-4.

3. The fusion protein of claim 1, wherein the Fc function of the Fc region of the full-length immunoglobulin to Fc receptor-positive cell is preserved.

4. A nucleic acid molecule comprising a nucleotide sequence encoding the fusion protein of claim 1, wherein the nucleic acid molecule is comprised in a vector or in a phagemid vector, or a host cell containing said nucleic acid molecule.

5. A pharmaceutical composition comprising the fusion protein of claim 1 and a pharmaceutically acceptable excipient.

6. A diagnostic or analytical kit comprising the fusion protein of claim 1.

* * * * *